United States Patent
Glezer et al.

(10) Patent No.: US 9,731,297 B2
(45) Date of Patent: Aug. 15, 2017

(54) ASSAY CARTRIDGES AND METHODS OF USING THE SAME

(75) Inventors: Eli N. Glezer, Del Mar, CA (US); Stephen Higgins, Gaithersburg, MD (US); Sandor Kovacs, Middletown, DE (US); Sudeep Kumar, Gaithersburg, MD (US); Kenneth Page, Germantown, MD (US); Kristian Roth, Germantown, MD (US); George Sigal, Rockville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

(21) Appl. No.: 13/343,834

(22) Filed: Jan. 5, 2012

(65) Prior Publication Data

US 2012/0178091 A1   Jul. 12, 2012

Related U.S. Application Data

(60) Provisional application No. 61/460,708, filed on Jan. 6, 2011.

(51) Int. Cl.
| | | |
|---|---|---|
| C12M 1/40 | (2006.01) | |
| C12Q 1/68 | (2006.01) | |
| B01L 7/00 | (2006.01) | |
| B01L 3/00 | (2006.01) | |

(52) U.S. Cl.
CPC ............ *B01L 7/525* (2013.01); *B01L 3/5027* (2013.01); *B01L 2200/027* (2013.01); *B01L 2200/0605* (2013.01); *B01L 2200/0621* (2013.01); *B01L 2200/0631* (2013.01); *B01L 2200/10* (2013.01); *B01L 2200/146* (2013.01); *B01L 2200/16* (2013.01); *B01L 2300/0645* (2013.01); *B01L 2300/087* (2013.01); *B01L 2300/0816* (2013.01); *B01L 2300/0864* (2013.01); *B01L 2300/0867* (2013.01); *B01L 2300/0883* (2013.01); *B01L 2400/0487* (2013.01); *B01L 2400/0688* (2013.01); *B01L 2400/0694* (2013.01); *C12Q 1/686* (2013.01)

(58) Field of Classification Search
None
See application file for complete search history.

(56) References Cited

U.S. PATENT DOCUMENTS

| | | |
|---|---|---|
| 3,918,435 A | 11/1975 | Beall et al. |
| 4,498,780 A | 2/1985 | Banno et al. |
| 4,586,604 A | 5/1986 | Alter |
| 4,803,998 A | 2/1989 | Kezes et al. |
| 4,813,432 A | 3/1989 | Sanit-Amand |
| 4,849,330 A | 7/1989 | Humphries et al. |
| 4,978,504 A | 12/1990 | Nason |
| 5,030,310 A | 7/1991 | Wogoman et al. |
| 5,066,372 A | 11/1991 | Weetall |
| 5,187,096 A | 2/1993 | Giaever et al. |
| 5,218,312 A | 6/1993 | Moro |
| 5,264,103 A | 11/1993 | Yoshioka et al. |
| 5,266,266 A | 11/1993 | Nason |
| 5,389,215 A | 2/1995 | Horiuchi et al. |
| 5,425,921 A | 6/1995 | Coakley et al. |
| 5,429,735 A | 7/1995 | Johnson et al. |
| 5,437,999 A | 8/1995 | Diebold et al. |
| 5,459,068 A | 10/1995 | Madara |
| 5,527,670 A | 6/1996 | Stanley |
| 5,547,555 A | 8/1996 | Schwartz et al. |
| 5,589,136 A | 12/1996 | Northrup et al. |
| 5,632,957 A | 5/1997 | Heller et al. |
| 5,648,213 A | 7/1997 | Reddy et al. |
| 5,670,322 A | 9/1997 | Eggers et al. |
| 5,776,672 A | 7/1998 | Hashimoto et al. |
| 5,849,486 A | 12/1998 | Heller et al. |
| 5,866,434 A | 2/1999 | Massey et al. |
| 5,968,745 A | 10/1999 | Thorp et al. |
| 5,972,694 A | 10/1999 | Mathus |
| 6,066,448 A | 5/2000 | Wohlstadter et al. |
| 6,071,395 A | 6/2000 | Lange |
| 6,083,763 A | 7/2000 | Balch |
| 6,090,545 A | 7/2000 | Wohlstadter et al. |
| 6,127,127 A | 10/2000 | Eckhardt et al. |
| 6,140,045 A | 10/2000 | Wohlstadter et al. |

(Continued)

FOREIGN PATENT DOCUMENTS

| | | |
|---|---|---|
| EP | 0 420 450 A1 | 4/1991 |
| EP | 1572318 B1 * | 3/2012 |

(Continued)

OTHER PUBLICATIONS

International Search Report and Written Opinion dated Aug. 29, 2012 received from the Korean Intellectual Property Office from related International Application No. PCT/US2012/020278.
International Search Report and Written Opinion dated Jul. 8, 2011 from related International Application No. PCT/US2010/058913.
Mendoza L.G. et al., "High-Throughput Microarray-Based Enzyme-Linked Immunosorbent Assay (ELISA)", *BioTechniques* 27(4):778-788 (1999).
Popovich N., "Mediated Electrochemical Detection of Nucleic Acids for Drug Discovery and Clinical Diagnostics", *IVD Technology*, 7(3):36-42 (2001).
Moody M.D. et al., "Array-Based ELISAs for High-Throughput Analysis of Human Cytokines", *BioTechniques* 31(1):186-194 (2001).

(Continued)

*Primary Examiner* — David Thomas
(74) *Attorney, Agent, or Firm* — Scully, Scott, Murphy & Presser, P.C.

(57) ABSTRACT

Assay cartridges are described that have purification, reaction, and detection zones and other fluidic components which can include sample chambers, waste chambers, conduits, vents, reagent chambers, reconstitution chambers and the like. The assay cartridges are used to conduct multiplexed nucleic acid measurements. Also described are kits including such cartridges, methods of using the same, and a reader configured to analyze an assay conducted using an assay cartridge.

55 Claims, 33 Drawing Sheets

(56) References Cited

U.S. PATENT DOCUMENTS

| | | | |
|---|---|---|---|
| 6,207,369 B1 | 3/2001 | Wohlstadter et al. | |
| 6,238,869 B1 | 5/2001 | Kris et al. | |
| 6,251,685 B1 | 6/2001 | Dorsel et al. | |
| 6,258,326 B1 | 7/2001 | Modlin | |
| 6,264,814 B1 | 7/2001 | Lange | |
| 6,376,233 B1 | 4/2002 | Wolf et al. | |
| 6,413,783 B1 | 7/2002 | Wohlstadter et al. | |
| 6,553,318 B2 | 4/2003 | Mansky | |
| 6,645,432 B1 | 11/2003 | Anderson et al. | |
| 6,689,258 B1 | 2/2004 | Lansford et al. | |
| 6,801,041 B2 | 10/2004 | Karinka et al. | |
| 7,419,821 B2 | 9/2008 | Davies et al. | |
| 7,497,997 B2 | 3/2009 | Glezer et al. | |
| 7,842,246 B2 | 11/2010 | Wohlstadter et al. | |
| 8,012,745 B2 | 9/2011 | Glezer et al. | |
| 2001/0006417 A1 | 7/2001 | Modlin et al. | |
| 2001/0029048 A1 | 10/2001 | Ding et al. | |
| 2002/0014415 A1 | 2/2002 | Nakayama et al. | |
| 2002/0025573 A1 | 2/2002 | Maher et al. | |
| 2003/0170881 A1 | 9/2003 | Davies et al. | |
| 2004/0072158 A1 | 4/2004 | Henkens et al. | |
| 2004/0259237 A1* | 12/2004 | Kellogg et al. | 435/287.1 |
| 2006/0110292 A1 | 5/2006 | Deverse et al. | |
| 2006/0153745 A1* | 7/2006 | Ermakov | 422/130 |
| 2007/0264629 A1 | 11/2007 | Holmes et al. | |
| 2007/0292941 A1* | 12/2007 | Handique et al. | 435/288.7 |
| 2008/0153152 A1* | 6/2008 | Wakabayashi et al. | 435/287.2 |
| 2009/0065357 A1* | 3/2009 | Glezer et al. | 204/403.15 |
| 2010/0063268 A1* | 3/2010 | Kanehara et al. | 536/55.3 |
| 2010/0267063 A1 | 10/2010 | Billadeau et al. | |
| 2011/0059870 A1 | 3/2011 | Wohlstadter et al. | |
| 2011/0201099 A1 | 8/2011 | Anderson et al. | |
| 2011/0203924 A1 | 8/2011 | Wohlstadter et al. | |

FOREIGN PATENT DOCUMENTS

| | | |
|---|---|---|
| JP | 2006-517652 A | 7/2006 |
| JP | 2007-120399 A | 5/2007 |
| JP | 2009-517075 A | 4/2009 |
| WO | WO 94/19683 | 9/1994 |
| WO | WO 98/20974 | 5/1998 |
| WO | WO 98/36266 | 8/1998 |
| WO | WO 2009/049268 A1 | 4/2009 |
| WO | WO 2009/149115 A1 | 12/2009 |
| WO | WO 2010088514 A1 * | 8/2010 |
| WO | WO 2010144683 A2 * | 12/2010 |

OTHER PUBLICATIONS

Umek R. et al., "Electronic Detection of Nucleic Acids-A Versatile Platform for Molecular Diagnostics", *J. Molecular Diagnostics* 3(2):74-84 (2001).

Supplementary European Search Report dated Jun. 15, 2011 from related European Patent Application 03810078.8.

Japanese Notice of Reasons for Refusal dated Aug. 18, 2015 received from Application No. 2013-548528, together with an English-language translation.

Japanese Notice of Reason for Refusal dated Apr. 5, 2016 received from Application No. 2013-548528, together with an English-language translation.

\* cited by examiner

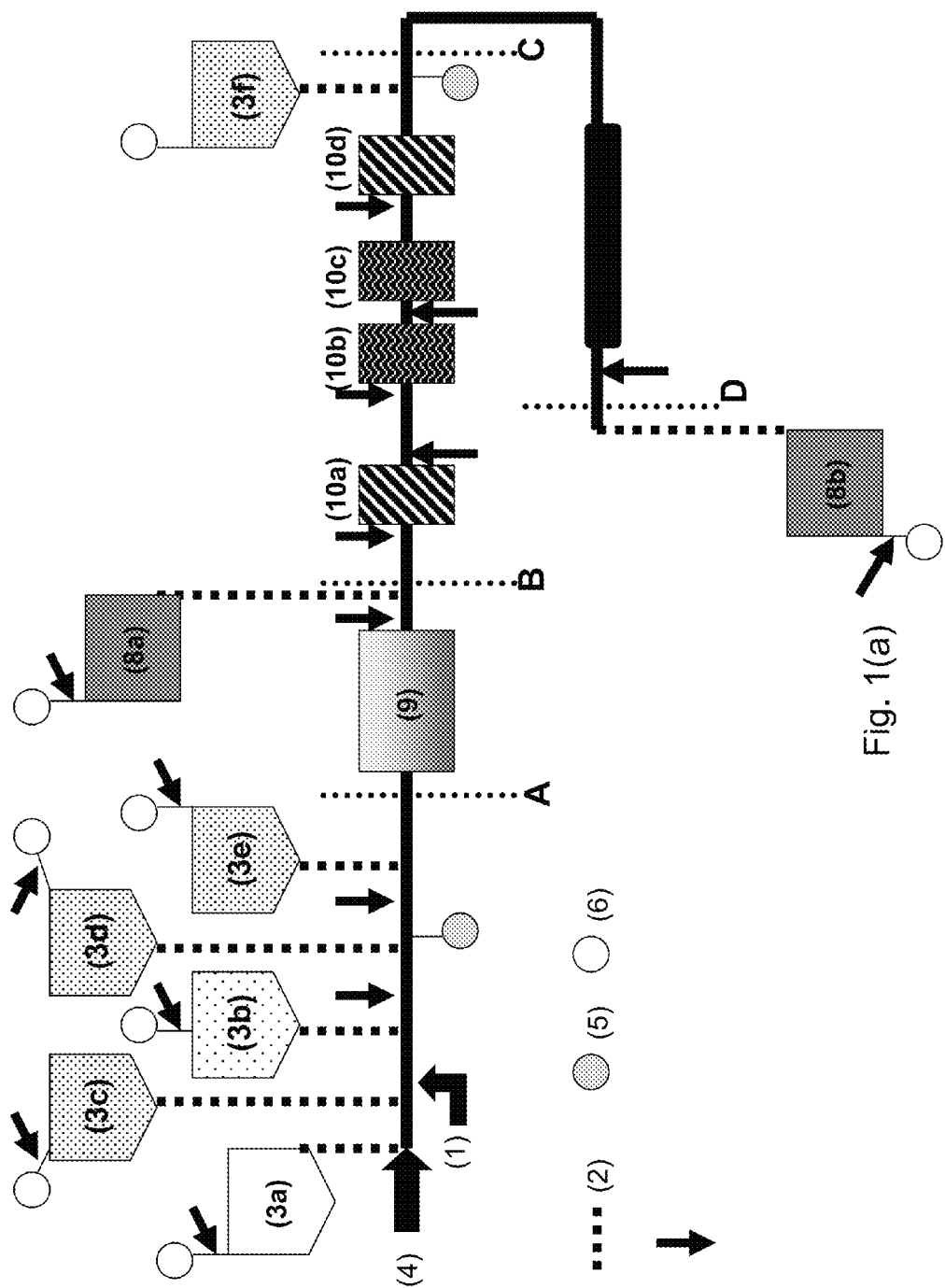

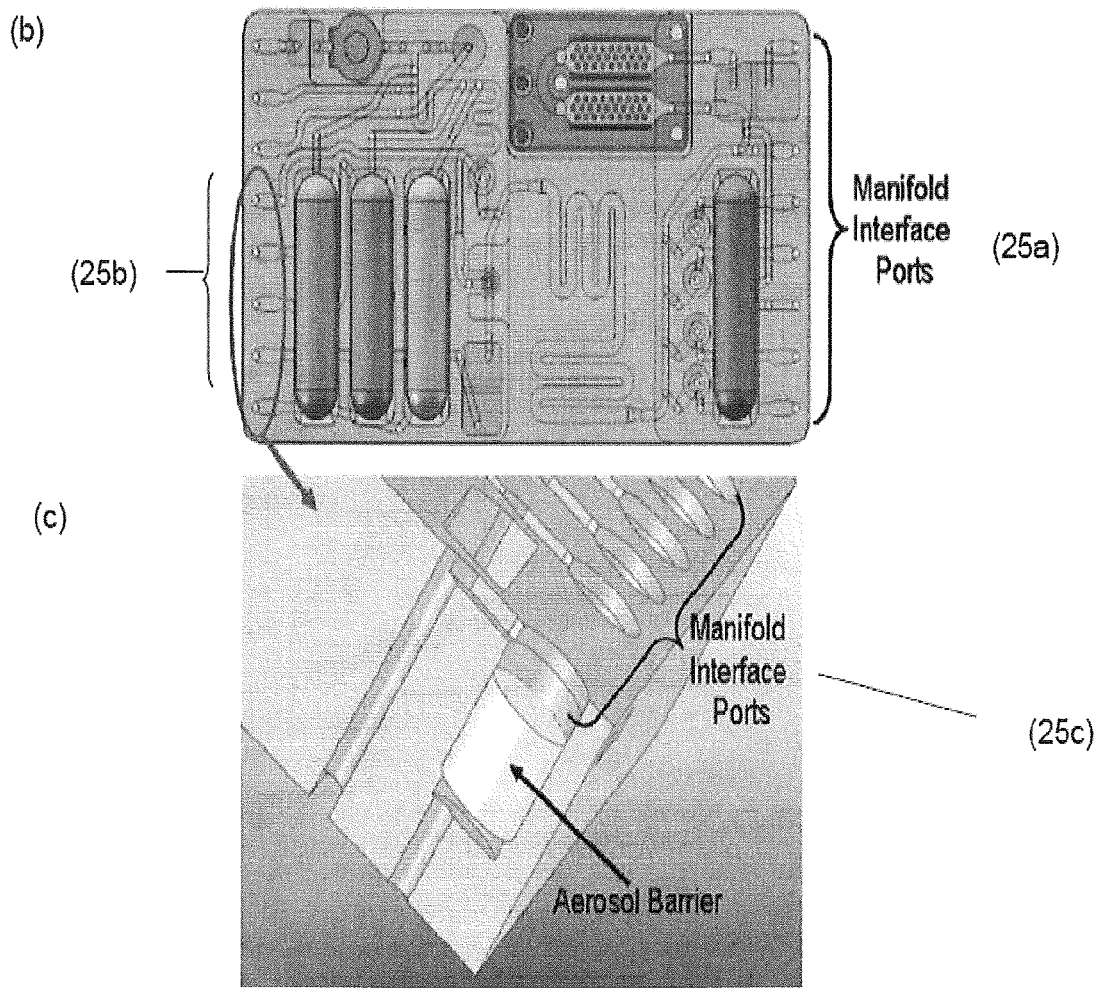
Fig. 2(b-c)

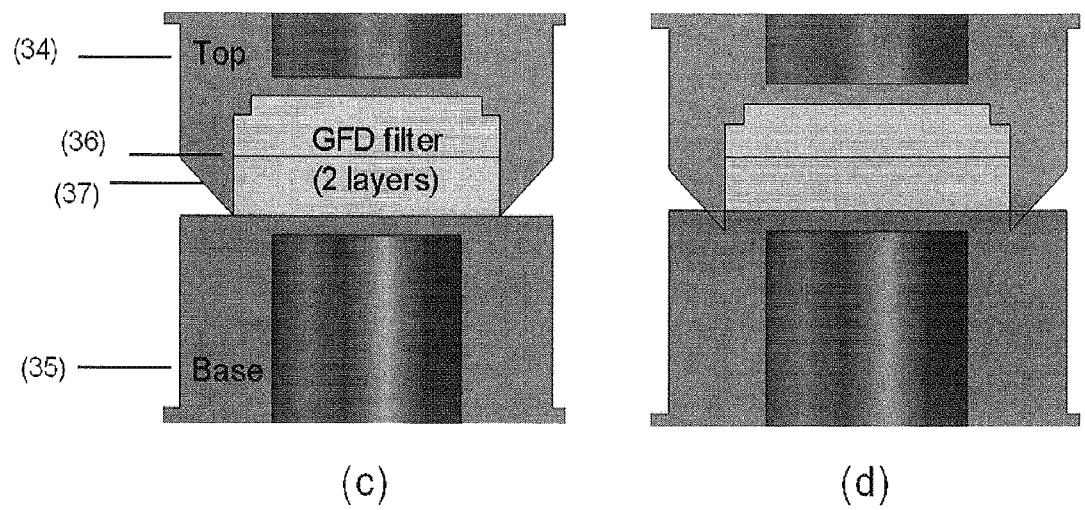
Fig. 3(c-d)

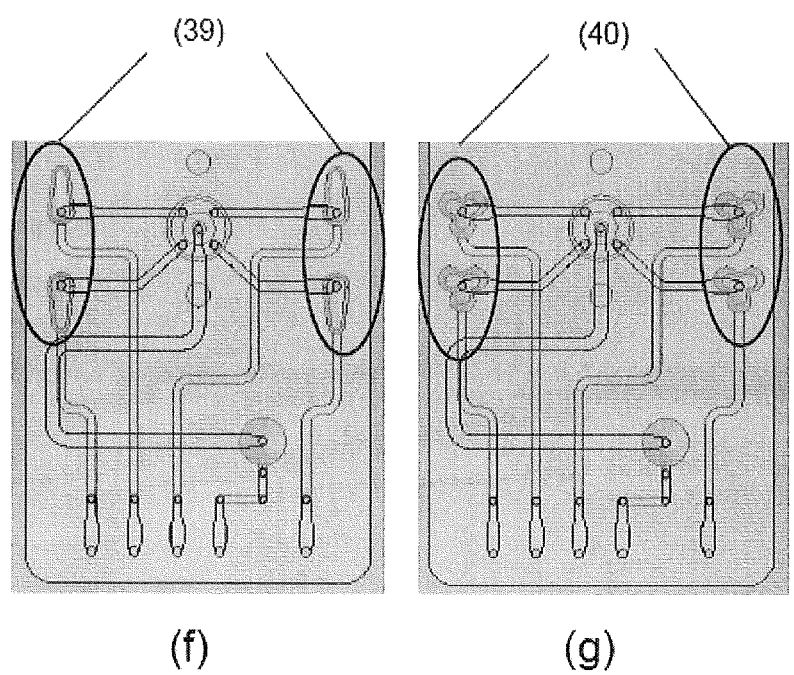
Fig. 3(f-g)

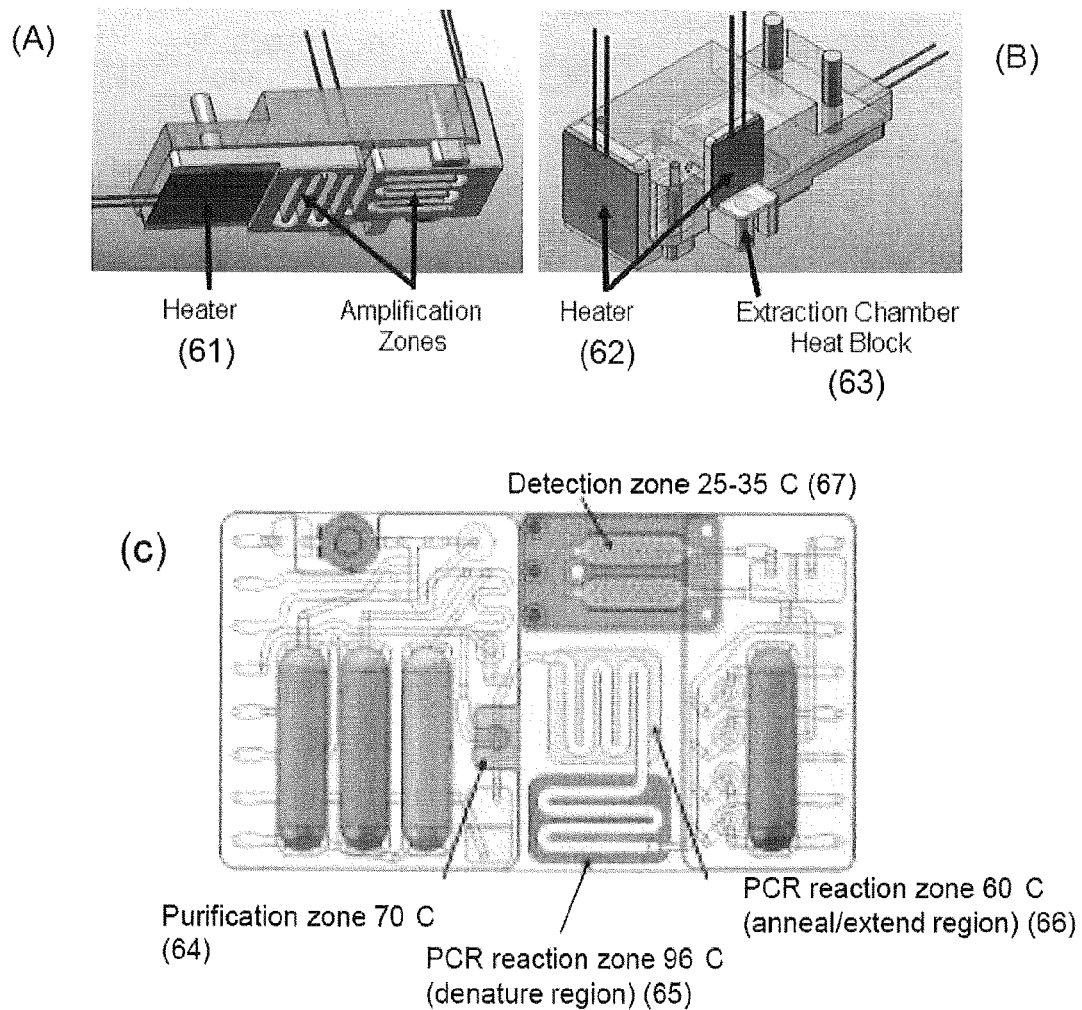
Fig. 6(a-c)

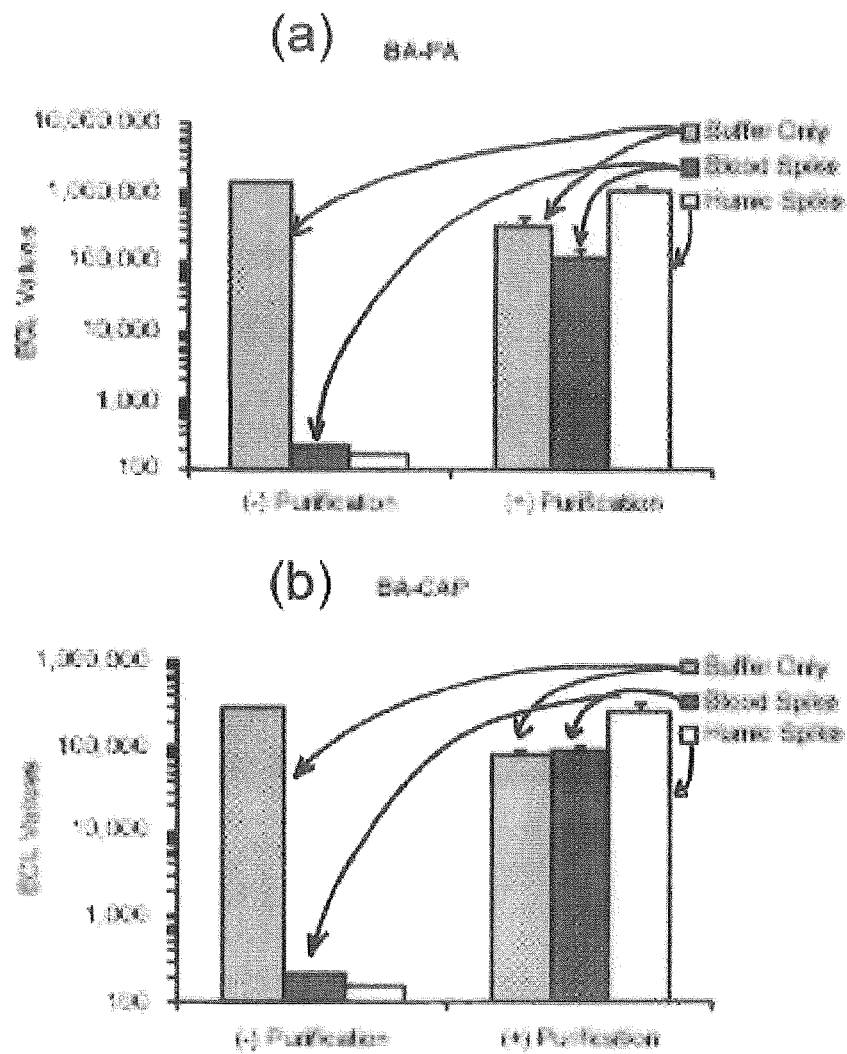
Fig. 12(a-b)

| CT Value | | | | | | |
|---|---|---|---|---|---|---|
| B. anthracis | Extraction Method | | | | | |
| # of Bacteria | MSD | MSD | MSD | Qiagen | Qiagen | Qiagen |
| 1 x 10 4 | 31.22 | 30.33 | 30.94 | 30.75 | 31.21 | 30.93 |
| 5 x 10 3 | 32.05 | 31.55 | 31.85 | 32.01 | 31.75 | 31.98 |
| 1 x 10 3 | 34.62 | 33.56 | 32.87 | 35.47 | 33.35 | 34.34 |
| 1 x 10 2 | ND | 34.14 | ND | ND | ND | ND |
| NSC | ND | ** (Neg.) | | ND | ND | |

** CT 34.29 with uncertain call. Determined to be negative based on curve.

Fig. 13

| Organism | Target | Amplicon Size (BP) | Primers | Sequence | SEQ ID N . | Fina Conc. (uM) |
|---|---|---|---|---|---|---|
| Bacillus anthracis (BA) | Protective antigen (PA) pX01 | 153 | R v rs | TTCAAgTTgTACTggACCgATTCTC | 19 | 5 |
| | | | Forward | TCCATCATTgTCACggTCTgg | 20 | 5 |
| | Capsule B (CAPB4-New) pX02 | 86 | Reverse | CAgATAATgCATCgCTTgCTTTAg | 21 | 5 |
| | | | Forward | ggATgAgCATTCAACATACCACg | 22 | 5 |
| Brucella species | Outer membrane protein 2a (omp2a) | 90 | Reverse | CCAggCgTACCggTTATCTC | 23 | 5 |
| | | | Forward | AgACCCTTTTgAggTCTACTCCCTTA | 24 | 5 |
| | Outer membrane protein 2b (omp2b) | 159 | Reverse | ATgAACATCAAgAgCCTTCTCCTT | 25 | 5 |
| | | | Forward | ggTgCCCggAATgTAgAAgTAg | 26 | 5 |
| Francisella tularensis (FT) | Tul4 | 103 | R v rs | CAgCATACAATAATAACCCACAAgg | 27 | 5 |
| | | | Forward | TCAgCATACTTAgTAATTgggAAgC | 28 | 5 |
| | fopA | 139 | Reverse | CTggTTTAACATggTTCTTTggTg | 29 | 5 |
| | | | Forward | CCAgCAggTAAAACATACTTAgACTCA | 30 | 5 |
| Orthopox Species | Hemagglutinin (HA) | 130 | Reverse | gATgATgCAACTCTATCATgTA | 31 | 5 |
| | | | Forward | gTATAATTATCAAAATACAAgACgTC | 32 | 5 |
| | DNA Polymerase (E9L) | 177 | Reverse | gAACATTTTTggCAgAgAgAgCC | 33 | 5 |
| | | | Forward | CAACTCTTAgCCgAAgCgTATgAg | 34 | 5 |
| Yersinia pestis (YP) | Pesticin Immunity Protein (PIM) | 131 | Reverse | AgTggCCTTgCAgAAAAAA | 35 | 5 |
| | | | Forward | gTAAACTCggTTTgCTTgAAg | 36 | 5 |
| | F1 Antigen (caf1) | 94 | Reverse | gTgAgAgTAggATCATATACCCgTTAgA | 37 | 5 |
| | | | Forward | ATCCTAgACTgAATgAgAACCggA | 38 | 5 |
| Venezuelan Equine Enc halitis (VEE) | NSP4 | 92 | Reverse | CTTggCAAACCTCTggCAgC | 39 | 5 |
| | | | Forward | ATACCCACTCggTTCCAgCg | 40 | 5 |
| | 5'UTR | 112 | Reverse | gAgCTTCCCgCAgTTTgA | 41 | 5 |
| | | | Forward | TgggTCCACCTCCgTTT | 42 | 5 |
| Ebola (EV) | Glycoprotein Zaire | 171 | Reverse | gCTggTgAATgggCTgAAAA | 43 | 5 |
| | | | Forward | CACCCTCTTTATggAAggCAAA | 44 | 5 |
| | Glycoprotein Zaire (Liz Fritz) | 105 | Reverse | TgCCTTATCCgACTCgCAAT | 45 | 5 |
| | | | Forward | TgCTCACgTTCCgTAACTACCA | 46 | 5 |
| Marburg (MV) | Nucleoprotein Musoki/Ci67 | 100 | Reverse | GCGAACAATATCAACAACTACG | 47 | 5 |
| | | | Forward | TCggCAATAgCTTgAATTTCCT | 48 | 5 |
| | VP40 Musoki/Ci67 | 165 | Reverse | CAgTTCCAgCAATTACAACACATACA | 49 | 5 |
| | | | Forward | GGAAGGAGTATCCCAATCTCAGC | 50 | 5 |

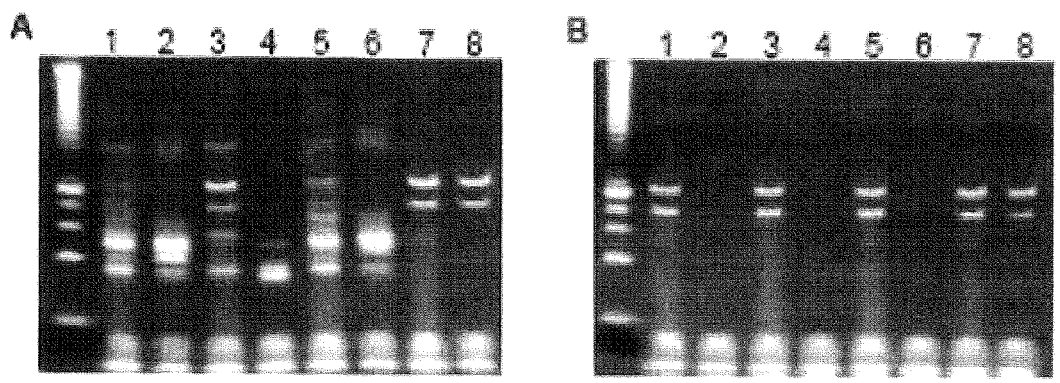
Fig. 15(a-b)
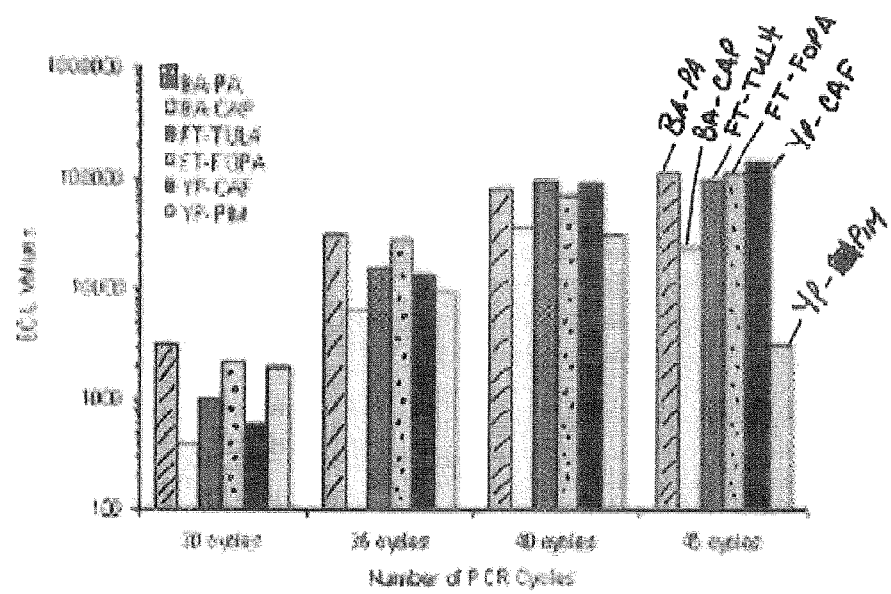
Fig. 15(c)

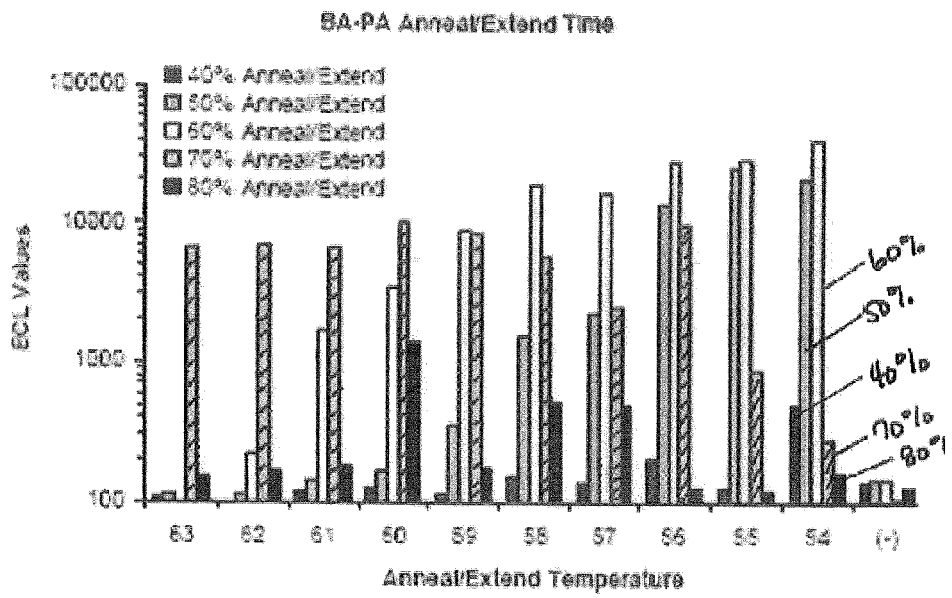
Fig. 16(a)
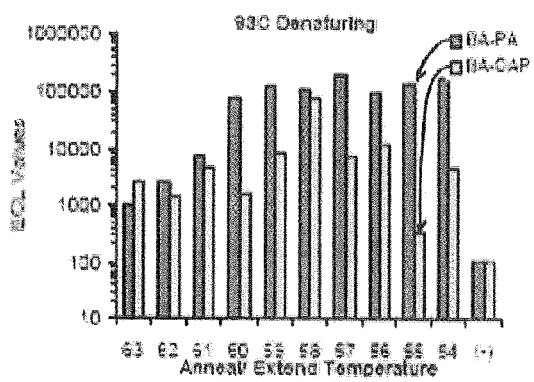 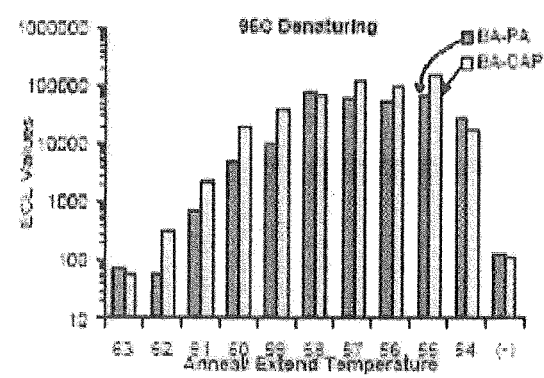
Fig. 16(b)                    Fig. 16(c)

| | Per Cycle Amplification Efficiency | | |
|---|---|---|---|
| | Flow Cell Prototype | | Robocycler |
| Target | Polycarbonate | TOPAS | Polypropylene |
| BA-PA | 1.78 | 1.73 | 1.70 |
| BA-CAP | 1.78 | 1.73 | 1.83 |
| FT-TUL4 | 1.97 | 1.89 | 1.68 |
| FT-FOPA | 1.86 | 1.85 | 1.62 |
| YP-PIM | 1.66 | 1.67 | 1.79 |
| YP-CAF | 1.85 | 1.68 | 1.84 |
| BR-OMP2a | 1.67 | 1.67 | 1.83 |
| BR-OMP2b | ND | ND | ND |
| OP-HEM | 1.99 | 1.70 | 2.00 |
| OP-DNA | 1.58 | 1.61 | 1.55 |
| VEE-NSP4 | 1.57 | 1.59 | 1.51 |
| VEE-5'UTR | 1.86 | 1.75 | 1.80 |
| EV-Zaire | 1.83 | 1.82 | 1.81 |
| EV-LF | 1.60 | 1.68 | 1.65 |
| MV-NP | 1.62 | 1.66 | 1.66 |
| MV-VP40 | 1.97 | 1.87 | 1.95 |

Fig. 18

| Organism | Target | Capture Sequence | Detection Sequence |
|---|---|---|---|
| Bacillus anthracis (BA) | PA | TGAGTTCGAAGATTTTTG (SEQ ID NO: 51) | TTTTAATTCTGGCAATTGT (SEQ ID NO: 53) |
| | CAP | GCAGAGGCTCTTGGG (SEQ ID NO: 52) | ATTGATGAGGAAACA (SEQ ID NO: 54) |
| Francisella tularensis | TUL4 | TATGCCAACTATTGA (SEQ ID NO: 55) | GAGACCATAACGCCA (SEQ ID NO: 57) |
| | FOPA | GAGACCATAACGCCA (SEQ ID NO: 56) | TAATCTTGGGTGTTT (SEQ ID NO: 58) |
| Yersinia pestis | PIM | TGGAATTGGGCTCCTTA (SEQ ID NO: 59) | TGCATGGAATCATAGATG (SEQ ID NO: 61) |
| | CAF | ACCAAGCACTCATAACAA (SEQ ID NO: 60) | CCCGAAGCCGTTGAA (SEQ ID NO: 62) |
| Brucella spp. | OMP2B | GGAGCCTGCCATTGT (SEQ ID NO: 63) | TTGTATCATGGCACT (SEQ ID NO: 65) |
| | OMP2A | CATGGCACTTAGAAC (SEQ ID NO: 64) | CACTTAGAACCTTCT (SEQ ID NO: 66) |
| Orthopox | HEM | GTTGTCTGTTTCCCA (SEQ ID NO: 67) | TAGATGCCATGAGAC (SEQ ID NO: 69) |
| | POL | TTTTGCAAGATGTCT (SEQ ID NO: 68) | GTATTAATTCTAGG (SEQ ID NO: 70) |
| Venezuelan Equine Encephalitis | NSP4 | GTCGAAGGCGCTCCC (SEQ ID NO: 71) | GTCGAAGGCGCTCCC (SEQ ID NO: 73) |
| | 5'UTR | GACGCTTACGGCGCT (SEQ ID NO: 72) | TACCGGAGAGGTGGC (SEQ ID NO: 74) |
| Ebola Virus | GP | GATTTCAAGATTGTAGCAG (SEQ ID NO: 75) | GACACTCACTCCCGTC (SEQ ID NO: 77) |
| | LF | ACCATCAGCTAACAGAG (SEQ ID NO: 76) | CTTCACAAAGTGTTTGAAC (SEQ ID NO: 78) |
| Marburg Mirus | NP | TGTAGTTTTACTTCCGCA (SEQ ID NO: 79) | GGCCATATCAAAATTTATTTT (SEQ ID NO: 81) |
| | VP40 | GATGTTCATGTGTCGCCT (SEQ ID NO: 80) | GTTGTAATTGCTGGAACT (SEQ ID NO: 82) |

Fig. 20(a)

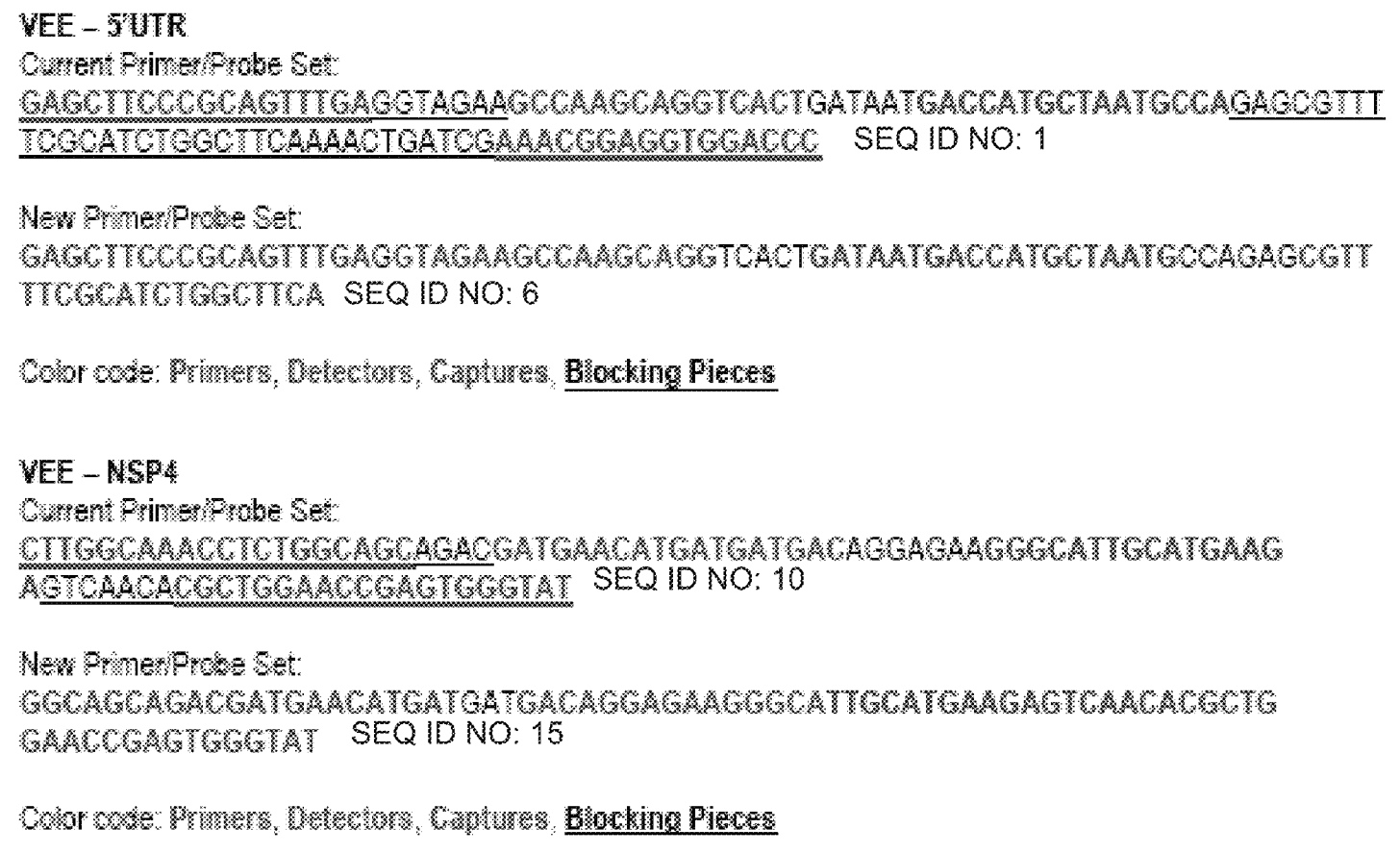

VEE – 5'UTR
Current Primer/Probe Set:
GAGCTTCCCGCAGTTTGAGGTAGAAGCCAAGCAGG (a) 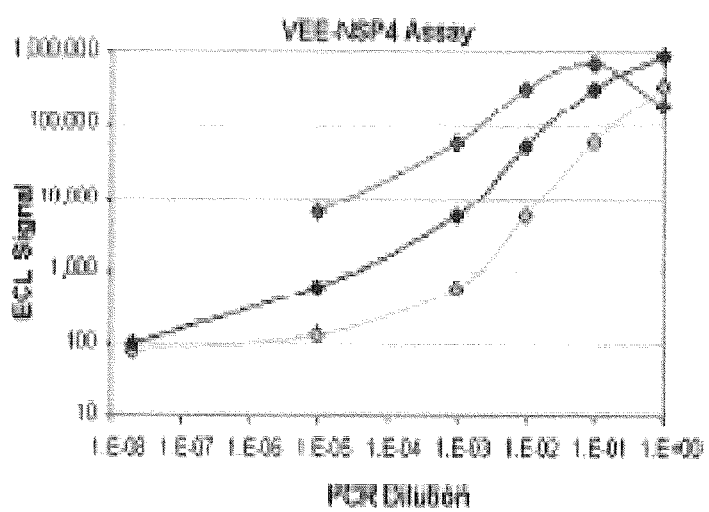
(b) 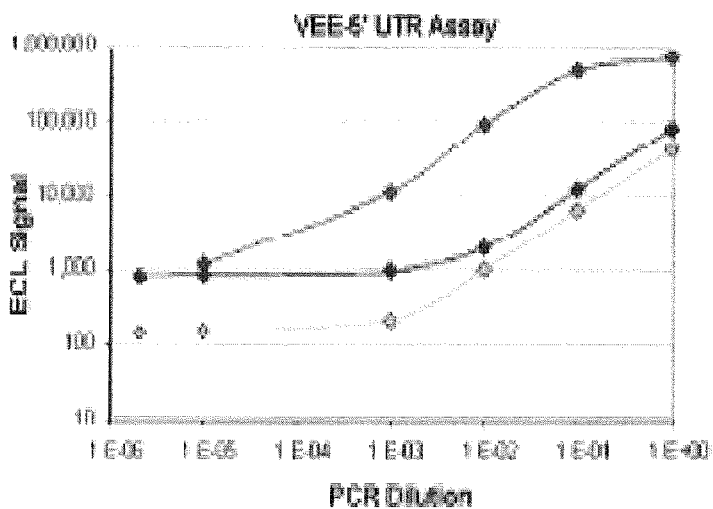
Fig. 21(a-b)

| Spot | ECL Signals - Synthetic Target Tested | | | | | | | | |
|---|---|---|---|---|---|---|---|---|---|
| | NSB | BA-PA | BA-CAP | FT-Tul4 | FT-FopA | YP-CAF | YP-PIM | Br-OMP2A | BR-OMP2B |
| BA-PA | 156 | 50,286 | 223 | 142 | 140 | 110 | 136 | 122 | 127 |
| BA-CAP | 168 | 119 | 54,675 | 427 | 157 | 105 | 181 | 130 | 136 |
| FT-Tul4 | 134 | 90 | 1,026 | 51,233 | 142 | 75 | 95 | 161 | 94 |
| FT-FopA | 155 | 132 | 123 | 169 | 47,294 | 98 | 105 | 104 | 125 |
| YP-CAF | 159 | 149 | 141 | 126 | 111 | 30,975 | 205 | 158 | 139 |
| YP-PIM | 264 | 227 | 243 | 215 | 192 | 218 | 69,230 | 264 | 209 |
| Br-OMP2A | 234 | 187 | 178 | 183 | 164 | 133 | 191 | 57,515 | 270 |
| BR-OMP2B | 206 | 169 | 165 | 153 | 166 | 153 | 161 | 262 | 47,583 |
| Orth-Hemagl | 169 | 150 | 125 | 1,005 | 127 | 107 | 122 | 117 | 108 |
| Orth-DNA Pol | 171 | 148 | 145 | 139 | 129 | 118 | 156 | 131 | 134 |
| VEE-NSP4 | 155 | 116 | 115 | 115 | 109 | 96 | 117 | 131 | 114 |
| VEE-5'UTR | 397 | 373 | 358 | 328 | 316 | 303 | 293 | 289 | 228 |
| Ebola | 146 | 132 | 115 | 125 | 124 | 101 | 128 | 110 | 110 |
| Ebola-LF | 151 | 137 | 124 | 121 | 110 | 114 | 132 | 121 | 107 |
| Marburg-NP | 141 | 95 | 115 | 127 | 115 | 96 | 107 | 121 | 110 |
| Marburg-VP40 | 180 | 131 | 168 | 161 | 146 | 127 | 142 | 159 | 139 |
| DL, molec/mL | | 1.7E+07 | 1.6E+08 | 1.3E+08 | 3.6E+07 | 8.3E+07 | 7.2E+07 | 6.6E+07 | 5.8E+08 |
| Conc, molec/mL | | 1.0E+10 | 1.0E+11 | 8.0E+10 | 2.0E+10 | 3.0E+10 | 5.0E+10 | 4.0E+10 | 3.0E+11 |
| Spot | Cross-Reactivity - Synthetic Target Tested | | | | | | | | |
| | NSB | BA-PA | BA-CAP | FT-Tul4 | FT-FopA | YP-CAF | YP-PIM | Br-OMP2A | BR-OMP2B |
| BA-PA | | 99.7% | 0.1% | 0.0% | 0.0% | -0.1% | 0.0% | -0.1% | -0.1% |
| BA-CAP | | -0.1% | 99.7% | 0.5% | 0.0% | -0.2% | 0.0% | -0.1% | -0.1% |
| FT-Tul4 | | -0.1% | 1.6% | 99.7% | 0.0% | -0.2% | -0.1% | 0.0% | -0.1% |
| FT-FopA | | 0.0% | -0.1% | 0.0% | 99.7% | -0.2% | -0.1% | -0.1% | -0.1% |
| YP-CAF | | 0.0% | 0.0% | -0.1% | -0.1% | 99.5% | 0.1% | 0.0% | 0.0% |
| YP-PIM | | -0.1% | 0.0% | -0.1% | -0.2% | -0.1% | 99.6% | 0.0% | -0.1% |
| Br-OMP2A | | -0.1% | -0.1% | -0.1% | -0.1% | -0.3% | -0.1% | 99.6% | 0.1% |
| BR-OMP2B | | -0.1% | -0.1% | -0.1% | -0.1% | -0.2% | -0.1% | 0.1% | 99.6% |
| Orth-Hemagl | | 0.0% | -0.1% | 1.6% | -0.1% | -0.2% | -0.1% | -0.1% | -0.1% |
| Orth-DNA Pol | | 0.0% | 0.0% | -0.1% | -0.1% | -0.2% | 0.0% | -0.1% | -0.1% |
| VEE-NSP4 | | -0.1% | -0.1% | -0.1% | -0.1% | -0.2% | -0.1% | 0.0% | -0.1% |
| VEE-5'UTR | | 0.0% | -0.1% | -0.1% | -0.2% | -0.3% | -0.2% | -0.2% | -0.4% |
| Ebola | | 0.0% | -0.1% | 0.0% | 0.0% | -0.1% | 0.0% | -0.1% | -0.1% |
| Ebola-LF | | 0.0% | 0.0% | -0.1% | -0.1% | -0.1% | 0.0% | -0.1% | -0.1% |
| Marburg-NP | | -0.1% | 0.0% | 0.0% | -0.1% | -0.1% | 0.0% | 0.0% | -0.1% |
| Marburg-VP40 | | -0.1% | 0.0% | 0.0% | -0.1% | -0.2% | -0.1% | 0.0% | -0.1% |

Fig. 22(a)

| Spot | ECL Signals - Synthetic Target Tested | | | | | | | | |
|---|---|---|---|---|---|---|---|---|---|
| | NSB | Orth-Hemagl | Orth-DNA | VEE-NSP4 | VEE-5'UTR | Ebola | Ebola-LF | Marburg-NP | Marburg-VP40 |
| BA-PA | 156 | 133 | 137 | 114 | 138 | 136 | 150 | 138 | 148 |
| BA-CAP | 168 | 129 | 139 | 148 | 147 | 179 | 161 | 174 | 184 |
| FT-Tul4 | 134 | 428 | 143 | 136 | 120 | 106 | 147 | 147 | 132 |
| FT-FopA | 155 | 99 | 124 | 133 | 141 | 110 | 140 | 171 | 166 |
| YP-CAF | 159 | 170 | 120 | 135 | 140 | 155 | 147 | 143 | 155 |
| YP-PIM | 264 | 244 | 237 | 243 | 220 | 243 | 279 | 239 | 234 |
| Br-OMP2A | 234 | 358 | 187 | 285 | 223 | 240 | 251 | 231 | 217 |
| BR-OMP2B | 206 | 172 | 193 | 188 | 224 | 196 | 211 | 199 | 211 |
| Orth-Hemagl | 169 | 38,348 | 185 | 167 | 155 | 233 | 158 | 143 | 151 |
| Orth-DNA Pol | 171 | 152 | 38,862 | 204 | 169 | 3,554 | 222 | 191 | 171 |
| VEE-NSP4 | 155 | 145 | 136 | 72,275 | 1,200 | 152 | 150 | 210 | 150 |
| VEE-5'UTR | 397 | 407 | 388 | 1,061 | 91,903 | 365 | 379 | 376 | 320 |
| Ebola | 146 | 145 | 656 | 133 | 136 | 71,923 | 247 | 167 | 182 |
| Ebola-LF | 151 | 150 | 166 | 160 | 129 | 180 | 65,970 | 255 | 163 |
| Marburg-NP | 141 | 127 | 117 | 188 | 118 | 138 | 153 | 90,657 | 190 |
| Marburg-VP40 | 180 | 166 | 185 | 201 | 226 | 216 | 226 | 266 | 38,195 |
| DL, molec/mL | | 3.4E+07 | 2.2E+07 | 1.8E+08 | 4.1E+08 | 7.0E+07 | 2.2E+07 | 2.3E+07 | 1.4E+08 |
| Conc, molec/mL | | 1.5E+10 | 1.0E+10 | 1.5E+11 | 3.0E+11 | 6.0E+10 | 1.7E+10 | 2.5E+10 | 6.0E+10 |
| Spot | Cross-Reactivity - Synthetic Target Tested | | | | | | | | |
| | NSB | Orth-Hemagl | Orth-DNA | VEE-NSP4 | VEE-5'UTR | Ebola | Ebola-LF | Marburg-NP | Marburg-VP40 |
| BA-PA | | -0.1% | 0.0% | -0.1% | 0.0% | 0.0% | 0.0% | 0.0% | 0.0% |
| BA-CAP | | -0.1% | -0.1% | 0.0% | 0.0% | 0.0% | 0.0% | 0.0% | 0.0% |
| FT-Tul4 | | 0.8% | 0.0% | 0.0% | 0.0% | 0.0% | 0.0% | 0.0% | 0.0% |
| FT-FopA | | -0.1% | -0.1% | 0.0% | 0.0% | -0.1% | 0.0% | 0.0% | 0.0% |
| YP-CAF | | 0.0% | -0.1% | 0.0% | 0.0% | 0.0% | 0.0% | 0.0% | 0.0% |
| YP-PIM | | -0.1% | -0.1% | 0.0% | 0.0% | 0.0% | 0.0% | 0.0% | -0.1% |
| Br-OMP2A | | 0.3% | -0.1% | 0.1% | 0.0% | 0.0% | 0.0% | 0.0% | 0.0% |
| BR-OMP2B | | -0.1% | 0.0% | 0.0% | 0.0% | 0.0% | 0.0% | 0.0% | 0.0% |
| Orth-Hemagl | | 99.6% | 0.0% | 0.0% | 0.0% | 0.1% | 0.0% | 0.0% | 0.0% |
| Orth-DNA Pol | | 0.0% | 99.6% | 0.0% | 0.0% | 4.7% | 0.1% | 0.0% | 0.0% |
| VEE-NSP4 | | 0.0% | 0.0% | 99.8% | 1.1% | 0.0% | 0.0% | 0.1% | 0.0% |
| VEE-5'UTR | | 0.0% | 0.0% | 0.9% | 99.6% | 0.0% | 0.0% | 0.0% | -0.2% |
| Ebola | | 0.0% | 1.3% | 0.0% | 0.0% | 99.8% | 0.2% | 0.0% | 0.1% |
| Ebola-LF | | 0.0% | 0.0% | 0.0% | 0.0% | 0.0% | 99.8% | 0.1% | 0.0% |
| Marburg-NP | | 0.0% | -0.1% | 0.1% | 0.0% | 0.0% | 0.0% | 99.8% | 0.1% |
| Marburg-VP40 | | 0.0% | 0.0% | 0.0% | 0.0% | 0.1% | 0.1% | 0.1% | 99.5% |

Fig. 22(b)

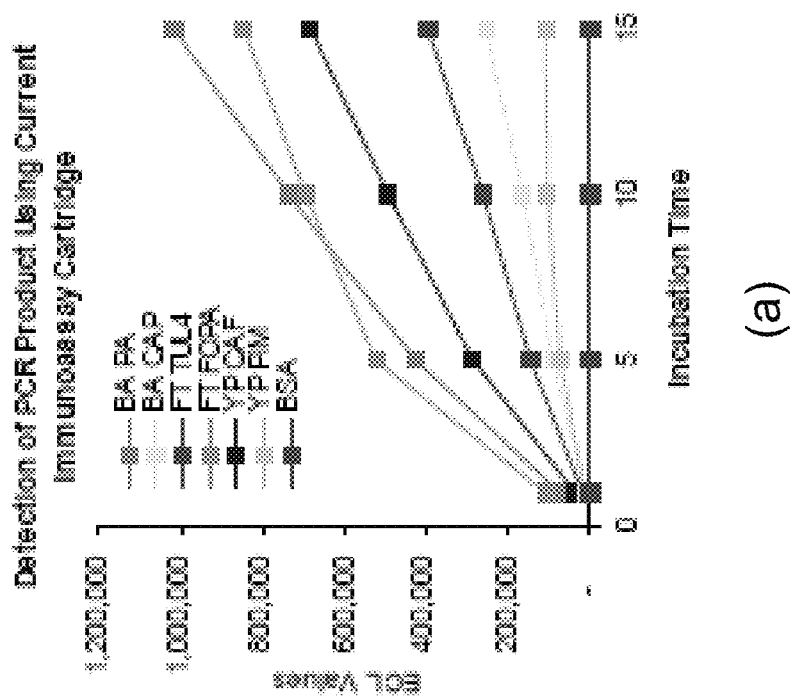
Fig. 23(a-b)

```
                       SEQUENCE LISTING

<160> NUMBER OF SEQ ID NOS: 82

<210> SEQ ID NO 1
<211> LENGTH: 111
<212> TYPE: DNA
<213> ORGANISM: Artificial Sequence
<220> FEATURE:
<223> OTHER INFORMATION: primer

<400> SEQUENCE: 1
gagcttcccg cagtttgagg tagaagccaa gcaggtcact gataatgacc atgctaatgc      60
cagagcgttt tcgcatctgg cttcaaaact gatcgaaacg gaggtggacc c              111

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
gagcttcccg cagtttgaaa acggaggtgg accc                                  34

<210> SEQ ID NO 3
<211> LENGTH: 15
<212> TYPE: DNA
<213> ORGANISM: Artificial Sequence
<220> FEATURE:
<223> OTHER INFORMATION: primer

<400> SEQUENCE: 3
gccaagcagg tcact                                                       15

<210> SEQ ID NO 4
<211> LENGTH: 16
<212> TYPE: DNA
<213> ORGANISM: Artificial Sequence
<220> FEATURE:
<223> OTHER INFORMATION: primer

<400> SEQUENCE: 4
gaccatgcta atgcca                                                      16

<210> SEQ ID NO 5
<211> LENGTH: 74
<212> TYPE: DNA
<213> ORGANISM: Artificial Sequence
<220> FEATURE:
<223> OTHER INFORMATION: primer

<400> SEQUENCE: 5
gagcttcccg cagtttgagg tagaagagcg ttttcgcatc tggcttcaaa actgatcgaa      60
acggaggtgg accc                                                        74
```

```
<210> SEQ ID NO 6
<211> LENGTH: 85
<212> TYPE: DNA
<213> ORGANISM: Artificial Sequence
<220> FEATURE:
<223> OTHER INFORMATION: primer

<400> SEQUENCE: 6
gagcttcccg cagtttgagg tagaagccaa gcaggtcact gataatgacc atgctaatgc    60
cagagcgttt tcgcatctgg cttca                                          85

<210> SEQ ID NO 7
<211> LENGTH: 38
<212> TYPE: DNA
<213> ORGANISM: Artificial Sequence
<220> FEATURE:
<223> OTHER INFORMATION: primer

<400> SEQUENCE: 7
gagcttcccg cagtttgacg ttttcgcatc tggcttca                            38

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
gtagaagcca agcagg                                                    16

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gataatgacc atgctaatg                                                 19

<210> SEQ ID NO 10
<211> LENGTH: 92
<212> TYPE: DNA
<213> ORGANISM: Artificial Sequence
<220> FEATURE:
<223> OTHER INFORMATION: primer

<400> SEQUENCE: 10
cttggcaaac ctctggcagc agacgatgaa catgatgatg acaggagaag ggcattgcat    60
gaagagtcaa cacgctggaa ccgagtgggt at                                  92

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11
cttggcaaac ctctggcagc cgctggaacc gagtgggtat                          40

<210> SEQ ID NO 12
```

<211> LENGTH: 18
<212> TYPE: DNA
<213> ORGANISM: Artificial Sequence
<220> FEATURE:
<223> OTHER INFORMATION: primer

<400> SEQUENCE: 12
gatgaacatg atgatgac                                                    18

<210> SEQ ID NO 13
<211> LENGTH: 15
<212> TYPE: DNA
<213> ORGANISM: Artificial Sequence
<220> FEATURE:
<223> OTHER INFORMATION: primer

<400> SEQUENCE: 13
gggcattgca tgaag                                                       15

<210> SEQ ID NO 14
<211> LENGTH: 51
<212> TYPE: DNA
<213> ORGANISM: Artificial Sequence
<220> FEATURE:
<223> OTHER INFORMATION: primer

<400> SEQUENCE: 14
cttggcaaac tctggcagc agacgtcaac acgctggaac cgagtgggta t                51

<210> SEQ ID NO 15
<211> LENGTH: 78
<212> TYPE: DNA
<213> ORGANISM: Artificial Sequence
<220> FEATURE:
<223> OTHER INFORMATION: primer

<400> SEQUENCE: 15
ggcagcagac gatgaacatg atgatgacag gagaagggca ttgcatgaag agtcaacacg      60
ctggaaccga gtgggtat                                                    78

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
ggcagcagac gatgaacatg atgatcgctg gaaccgagtg ggtat                      45

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gacaggagaa gggcattgca                                                  20

<210> SEQ ID NO 18
<211> LENGTH: 18
<212> TYPE: DNA
<213> ORGANISM: Artificial Sequence
<220> FEATURE:
<223> OTHER INFORMATION: primer

```
<400> SEQUENCE: 18
ttgcatgaag agtcaaca                                                  18

<210> SEQ ID NO 19
<211> LENGTH: 25
<212> TYPE: DNA
<213> ORGANISM: Bacillus anthracis

<400> SEQUENCE: 19
ttcaagttgt actggaccga ttctc                                          25

<210> SEQ ID NO 20
<211> LENGTH: 21
<212> TYPE: DNA
<213> ORGANISM: Bacillus anthracis

<400> SEQUENCE: 20
tccatcattg tcacggtctg g                                              21

<210> SEQ ID NO 21
<211> LENGTH: 24
<212> TYPE: DNA
<213> ORGANISM: Bacillus anthracis

<400> SEQUENCE: 21
cagataatgc atcgcttgct ttag                                           24

<210> SEQ ID NO 22
<211> LENGTH: 23
<212> TYPE: DNA
<213> ORGANISM: Bacillus anthracis

<400> SEQUENCE: 22
ggatgagcat tcaacatacc acg                                            23

<210> SEQ ID NO 23
<211> LENGTH: 20
<212> TYPE: DNA
<213> ORGANISM: Brucella species

<400> SEQUENCE: 23
ccaggcgtac cggttatctc                                                20

<210> SEQ ID NO 24
<211> LENGTH: 26
<212> TYPE: DNA
<213> ORGANISM: Brucella species

<400> SEQUENCE: 24 agacccttt gaggtctact ccctta                                          26

<210> SEQ ID NO 25
<211> LENGTH: 24
<212> TYPE: DNA
<213> ORGANISM: Brucella species

<400> SEQUENCE: 25
atgaacatca agagccttct cctt                                           24

<210> SEQ ID NO 26
<211> LENGTH: 22
<212> TYPE: DNA
```

<213> ORGANISM: Brucella species

<400> SEQUENCE: 26
ggtgcccgga atgtagaagt ag                                          22

<210> SEQ ID NO 27
<211> LENGTH: 25
<212> TYPE: DNA
<213> ORGANISM: Francisella tularensis

<400> SEQUENCE: 27
cagcatacaa taataaccca caagg                                       25

<210> SEQ ID NO 28
<211> LENGTH: 25
<212> TYPE: DNA
<213> ORGANISM: Francisella tularensis

<400> SEQUENCE: 28
tcagcatact tagtaattgg gaagc                                       25

<210> SEQ ID NO 29
<211> LENGTH: 24
<212> TYPE: DNA
<213> ORGANISM: Francisella tularensis

<400> SEQUENCE: 29
ctggtttaac atggttcttt ggtg                                        24

<210> SEQ ID NO 30
<211> LENGTH: 27
<212> TYPE: DNA
<213> ORGANISM: Francisella tularensis

<400> SEQUENCE: 30
ccagcaggta aaacatactt agactca                                     27

<210> SEQ ID NO 31
<211> LENGTH: 22
<212> TYPE: DNA
<213> ORGANISM: Orthopox species

<400> SEQUENCE: 31
gatgatgcaa ctctatcatg ta                                          22

<210> SEQ ID NO 32
<211> LENGTH: 26
<212> TYPE: DNA
<213> ORGANISM: Orthopox species

<400> SEQUENCE: 32
gtataattat caaaatacaa gacgtc                                      26

<210> SEQ ID NO 33
<211> LENGTH: 23
<212> TYPE: DNA
<213> ORGANISM: Orthopox species

<400> SEQUENCE: 33
gaacattttt ggcagagaga gcc                                         23

<210> SEQ ID NO 34
<211> LENGTH: 24

```
<212> TYPE: DNA
<213> ORGANISM: Orthopox species

<400> SEQUENCE: 34
caactcttag ccgaagcgta tgag                                              24

<210> SEQ ID NO 35
<211> LENGTH: 19
<212> TYPE: DNA
<213> ORGANISM: Yersinia pestis

<400> SEQUENCE: 35
agtggccttg cagaaaaaa                                                    19

<210> SEQ ID NO 36
<211> LENGTH: 21
<212> TYPE: DNA
<213> ORGANISM: Yersinia pestis

<400> SEQUENCE: 36
gtaaactcgg tttgcttgaa g                                                 21

<210> SEQ ID NO 37
<211> LENGTH: 28
<212> TYPE: DNA
<213> ORGANISM: Yersinia pestis

<400> SEQUENCE: 37
gtgagagtag gatcatatac ccgttaga                                          28

<210> SEQ ID NO 38
<211> LENGTH: 24
<212> TYPE: DNA
<213> ORGANISM: Yersinia pestis

<400> SEQUENCE: 38
atcctagact gaatgagaac cgga                                              24

<210> SEQ ID NO 39
<211> LENGTH: 20
<212> TYPE: DNA
<213> ORGANISM: Venezuelan equine encephalitis virus

<400> SEQUENCE: 39
cttggcaaac ctctggcagc                                                   20

<210> SEQ ID NO 40
<211> LENGTH: 20
<212> TYPE: DNA
<213> ORGANISM: Venezuelan equine encephalitis virus

<400> SEQUENCE: 40
atacccactc ggttccagcg                                                   20

<210> SEQ ID NO 41
<211> LENGTH: 18
<212> TYPE: DNA
<213> ORGANISM: Venezuelan equine encephalitis virus

<400> SEQUENCE: 41
gagcttcccg cagtttga                                                     18

<210> SEQ ID NO 42
```

```
<211> LENGTH: 17
<212> TYPE: DNA
<213> ORGANISM: Venezuelan equine encephalitis virus

<400> SEQUENCE: 42
tgggtccacc tccgttt                                                  17

<210> SEQ ID NO 43
<211> LENGTH: 20
<212> TYPE: DNA
<213> ORGANISM: Ebola virus

<400> SEQUENCE: 43
gctggtgaat gggctgaaaa                                               20

<210> SEQ ID NO 44
<211> LENGTH: 22
<212> TYPE: DNA
<213> ORGANISM: Ebola virus

<400> SEQUENCE: 44
caccctcttt atggaaggca aa                                            22

<210> SEQ ID NO 45
<211> LENGTH: 20
<212> TYPE: DNA
<213> ORGANISM: Ebola virus

<400> SEQUENCE: 45
tgccttatcc gactcgcaat                                               20

<210> SEQ ID NO 46
<211> LENGTH: 22
<212> TYPE: DNA
<213> ORGANISM: Ebola virus

<400> SEQUENCE: 46
tgctcacgtt ccgtaactac ca                                            22

<210> SEQ ID NO 47
<211> LENGTH: 22
<212> TYPE: DNA
<213> ORGANISM: Marburg virus

<400> SEQUENCE: 47
gcgaacaata tcaacaacta cg                                            22

<210> SEQ ID NO 48
<211> LENGTH: 22
<212> TYPE: DNA
<213> ORGANISM: Marburg virus

<400> SEQUENCE: 48
tcggcaatag cttgaatttc ct                                            22

<210> SEQ ID NO 49
<211> LENGTH: 26
<212> TYPE: DNA
<213> ORGANISM: Marburg virus

<400> SEQUENCE: 49
cagttccagc aattacaaca cataca                                        26
```

```
<210> SEQ ID NO 50
<211> LENGTH: 23
<212> TYPE: DNA
<213> ORGANISM: Marburg virus

<400> SEQUENCE: 50
ggaaggagta tcccaatctc agc                                          23

<210> SEQ ID NO 51
<211> LENGTH: 18
<212> TYPE: DNA
<213> ORGANISM: Bacillus anthracis

<400> SEQUENCE: 51
tgagttcgaa gatttttg                                                18

<210> SEQ ID NO 52
<211> LENGTH: 15
<212> TYPE: DNA
<213> ORGANISM: Bacillus anthracis

<400> SEQUENCE: 52
gcagaggctc ttggg                                                   15

<210> SEQ ID NO 53
<211> LENGTH: 19
<212> TYPE: DNA
<213> ORGANISM: Bacillus anthracis

<400> SEQUENCE: 53
ttttaattct ggcaattgt                                               19

<210> SEQ ID NO 54
<211> LENGTH: 15
<212> TYPE: DNA
<213> ORGANISM: Bacillus anthracis

<400> SEQUENCE: 54
attgatgagg aaaca                                                   15

<210> SEQ ID NO 55
<211> LENGTH: 15
<212> TYPE: DNA
<213> ORGANISM: Francisella tularensis

<400> SEQUENCE: 55
tatgccaact attga                                                   15

<210> SEQ ID NO 56
<211> LENGTH: 15
<212> TYPE: DNA
<213> ORGANISM: Francisella tularensis

<400> SEQUENCE: 56
gagaccataa cgcca                                                   15

<210> SEQ ID NO 57
<211> LENGTH: 15
<212> TYPE: DNA
<213> ORGANISM: Francisella tularensis

<400> SEQUENCE: 57
gagaccataa cgcca                                                   15
```

<210> SEQ ID NO 58
<211> LENGTH: 15
<212> TYPE: DNA
<213> ORGANISM: Francisella tularensis

<400> SEQUENCE: 58
taatcttggg tgttt                                                    15

<210> SEQ ID NO 59
<211> LENGTH: 17
<212> TYPE: DNA
<213> ORGANISM: Yersinia pestis

<400> SEQUENCE: 59
tggaattggg ctcctta                                                  17

<210> SEQ ID NO 60
<211> LENGTH: 18
<212> TYPE: DNA
<213> ORGANISM: Yersinia pestis

<400> SEQUENCE: 60
accaagcact cataacaa                                                 18

<210> SEQ ID NO 61
<211> LENGTH: 18
<212> TYPE: DNA
<213> ORGANISM: Yersinia pestis

<400> SEQUENCE: 61
tgcatggaat catagatg                                                 18

<210> SEQ ID NO 62
<211> LENGTH: 15
<212> TYPE: DNA
<213> ORGANISM: Yersinia pestis

<400> SEQUENCE: 62
cccgaagccg ttgaa                                                    15

<210> SEQ ID NO 63
<211> LENGTH: 15
<212> TYPE: DNA
<213> ORGANISM: Brucella species

<400> SEQUENCE: 63
ggagcctgcc attgt                                                    15

<210> SEQ ID NO 64
<211> LENGTH: 15
<212> TYPE: DNA
<213> ORGANISM: Brucella species

<400> SEQUENCE: 64
catggcactt agaac                                                    15

<210> SEQ ID NO 65
<211> LENGTH: 15
<212> TYPE: DNA
<213> ORGANISM: Brucella species

<400> SEQUENCE: 65
ttgtatcatg gcact                                                    15

```
<210> SEQ ID NO 66
<211> LENGTH: 15
<212> TYPE: DNA
<213> ORGANISM: Brucella species

<400> SEQUENCE: 66
cacttagaac cttct                                                    15

<210> SEQ ID NO 67
<211> LENGTH: 15
<212> TYPE: DNA
<213> ORGANISM: Orthopox species

<400> SEQUENCE: 67
gttgtctgtt tccca                                                    15

<210> SEQ ID NO 68
<211> LENGTH: 15
<212> TYPE: DNA
<213> ORGANISM: Orthopox species

<400> SEQUENCE: 68
ttttgcaaga tgtct                                                    15

<210> SEQ ID NO 69
<211> LENGTH: 15
<212> TYPE: DNA
<213> ORGANISM: Orthopox species

<400> SEQUENCE: 69
tagatgccat gagac                                                    15

<210> SEQ ID NO 70
<211> LENGTH: 15
<212> TYPE: DNA
<213> ORGANISM: Orthopox species

<400> SEQUENCE: 70
gtatttaatt ctagg                                                    15

<210> SEQ ID NO 71
<211> LENGTH: 15
<212> TYPE: DNA
<213> ORGANISM: Venezuelan equine encephalitis virus

<400> SEQUENCE: 71
gtcgaaggcg ctccc                                                    15

<210> SEQ ID NO 72
<211> LENGTH: 15
<212> TYPE: DNA
<213> ORGANISM: Venezuelan equine encephalitis virus

<400> SEQUENCE: 72
gacgcttacg gcgct                                                    15

<210> SEQ ID NO 73
<211> LENGTH: 15
<212> TYPE: DNA
<213> ORGANISM: Venezuelan equine encephalitis virus

<400> SEQUENCE: 73
```

```
gtcgaaggcg ctccc                                             15

<210> SEQ ID NO 74
<211> LENGTH: 15
<212> TYPE: DNA
<213> ORGANISM: Venezuelan equine encephalitis virus

<400> SEQUENCE: 74
taccggagag gtggc                                             15

<210> SEQ ID NO 75
<211> LENGTH: 19
<212> TYPE: DNA
<213> ORGANISM: Ebola virus

<400> SEQUENCE: 75
gatttcaaga ttgtagcag                                         19

<210> SEQ ID NO 76
<211> LENGTH: 17
<212> TYPE: DNA
<213> ORGANISM: Ebola virus

<400> SEQUENCE: 76
accatcagct aacagag                                           17

<210> SEQ ID NO 77
<211> LENGTH: 16
<212> TYPE: DNA
<213> ORGANISM: Ebola virus

<400> SEQUENCE: 77
gacactcact cccgtc                                            16

<210> SEQ ID NO 78
<211> LENGTH: 19
<212> TYPE: DNA
<213> ORGANISM: Ebola virus

<400> SEQUENCE: 78
cttcacaaag tgtttgaac                                         19

<210> SEQ ID NO 79
<211> LENGTH: 18
<212> TYPE: DNA
<213> ORGANISM: Marburg virus

<400> SEQUENCE: 79
tgtagtttta cttccgca                                          18

<210> SEQ ID NO 80
<211> LENGTH: 16
<212> TYPE: DNA
<213> ORGANISM: Marburg virus

<400> SEQUENCE: 80
gatgttcatg tcgcct                                            16

<210> SEQ ID NO 81
<211> LENGTH: 21
<212> TYPE: DNA
<213> ORGANISM: Marburg virus

<400> SEQUENCE: 81
```

```
ggccatatca aaatttattt t                                              21

<210> SEQ ID NO 82
<211> LENGTH: 18
<212> TYPE: DNA
<213> ORGANISM: Marburg virus

<400> SEQUENCE: 82
gttgtaattg ctggaact                                                  18
```

ASSAY CARTRIDGES AND METHODS OF USING THE SAME

CROSS REFERENCE TO RELATED APPLICATIONS

This application claims the benefit of U.S. Provisional Application No. 61/460,708 filed on Jan. 6, 2011, the entire contents of which are incorporated herein by reference.

STATEMENT REGARDING FEDERALLY-SPONSORED RESEARCH

This invention was made with federal support under W911NF-06-C-0120 from the Defense Threat Reduction Agency and W81XWH-10-2-0155 from the Congressionally Directed Medical Research Program. The U.S. government has certain rights in the invention.

FIELD OF THE INVENTION

This application relates to apparatuses, systems, kits and methods for conducting multiplexed nucleic acid measurements on a sample. These apparatuses include assay cartridges and readers for conducting these assays.

BACKGROUND OF THE INVENTION

Amplified nucleic acid assays for pathogens can achieve sensitivities approaching single organism detection. Practical considerations, in particular the need for time consuming, labor intensive, and complex sample preparation, have prevented wide spread application of amplified nucleic acid assays in field or point-of-care settings. In addition, there is a need for amplified nucleic acid assays with high levels of multiplexing that can detect multiple different organisms in a sample.

SUMMARY OF THE INVENTION

The invention provides an assay cartridge comprising a chamber and a fluidic network including: (a) a primary flow path comprising, from a proximate to a distal end, an inlet, a purification zone, a reaction zone, and a detection zone, wherein the primary flow path further comprises one or more air vent ports, and (b) one or more fluidic conduits each intersecting the primary flow path and fluidically connected to the chamber, wherein the chamber is connected to an additional air vent port, wherein the fluidic network is configured to meter a volume of fluid in the primary flow path. Preferably, a fluidic conduit of the one or more fluidic conduits comprises a multi-conduit fluidic junction including (i) a first conduit connecting the primary flow path and the chamber, and (ii) a second conduit connecting the chamber to the additional air vent port, wherein the fluidic conduit is in communication with an optical fluid sensor at a position distal from the fluidic junction and the metered volume of fluid is defined by the distance between the fluidic junction and the distal position.

Also provided is an assay system comprising an assay cartridge and a reader configured to use the assay cartridge, wherein the assay cartridge comprises a chamber and a fluidic network including (a) a primary flow path comprising, from a proximate to a distal end, an inlet, a purification zone, a reaction zone, and a detection zone, wherein the primary flow path further comprises one or more air vent ports, and (b) one or more fluidic conduits each intersecting the primary flow path and fluidically connected to the chamber, wherein the chamber is connected to an additional air vent port; wherein the fluidic network is configured to meter a volume of fluid in the primary flow path; and the reader comprises (x) an enclosure; (y) a cartridge tray for holding the cartridge during analysis in the reader; and (z) a mounting frame in the enclosure, the mounting frame is configured to align the cartridge with one or more reader components comprise (i) an optical detection assembly comprising at least one CCD detector; (ii) an ampoule breaking mechanism; (iii) an electrode contact pin assembly; (iv) a fluidic control manifold configured to drive fluid motion within the fluidic network; (v) one or more heater assemblies; and/or (vi) one or more optical fluid sensors.

In a preferred embodiment, the invention provides an assay cartridge for conducting a PCR analysis of a sample, the cartridge comprising a chamber and a fluidic network including (a) a primary flow path comprising, from a proximate to a distal end, an inlet, a purification zone, a PCR reaction zone, and a detection zone, wherein the primary flow path further comprises one or more air vent ports, and (b) one or more fluidic conduits each intersecting the primary flow path and fluidically connected to the chamber, wherein the chamber is connected to an additional air vent port, and the PCR reaction zone comprises a first reaction temperature controlled zone and a second reaction temperature controlled zone and the fluidic network is configured to shuttle a metered volume of fluid between the first and second reaction temperature controlled zones during a PCR reaction conducted in the PCR reaction zone. Preferably, a fluidic conduit of the one or more fluidic conduits comprises a multi-conduit fluidic junction including (i) a first conduit connecting the primary flow path and the chamber, and (ii) a second conduit connecting the chamber to the additional air vent port, wherein the fluidic conduit is in communication with an optical fluid sensor at a position distal from the fluidic junction and the metered volume of fluid is defined by the distance between the fluidic junction and the distal position.

The invention also provides an assay cartridge for conducting a PCR analysis of a sample, the cartridge comprising a fluidic network and a plurality of chambers, wherein the fluidic network comprises (a) a primary flow path comprising, from a proximate to a distal end, an inlet, a purification zone, a PCR reaction zone, and a detection zone, wherein the primary flow path further comprises one or more air vent ports, and (b) one or more fluidic conduits each intersecting the primary flow path and fluidically connected to one or more of the chambers, wherein each of the chambers are connected to an additional air vent port, wherein the plurality of chambers include: a sample chamber, a lysis reagent chamber, a lysis chamber, a purification reagent chamber, a plurality of PCR reagent chambers, a plurality of reconstitution chambers, and one or more waste chambers; and the PCR reaction zone comprises a first reaction temperature controlled zone and a second reaction temperature controlled zone and the fluidic network is configured to shuttle a metered volume of fluid between the first and second reaction temperature controlled zones during a PCR reaction conducted in the PCR reaction zone. Preferably, a fluidic conduit of the one or more fluidic conduits comprises a multi-conduit fluidic junction including (i) a first conduit connecting the primary flow path and the chamber, and (ii) a second conduit connecting the chamber to the additional air vent port, wherein the fluidic conduit is in communication with an optical fluid sensor at a position distal from the fluidic junction and the metered volume of fluid is defined by the distance between the fluidic junction and the distal position.

A further embodiment of the invention is a method of conducting a PCR analysis of a sample in an assay cartridge, the cartridge comprising a fluidic network and a plurality of chambers, wherein the fluidic network comprises (a) a primary flow path comprising, from a proximate to a distal end, (i) an inlet, (ii) a purification zone, (iii) a PCR reaction zone including a first reaction temperature controlled zone and a second reaction temperature controlled zone, and (iv) a detection zone, wherein the primary flow path further comprises (vi) one or more air vent ports, and (b) one or more fluidic conduits each intersecting the primary flow path and fluidically connected to one or more of the chambers, wherein each of the chambers are connected to an additional air vent port, wherein the plurality of chambers include: a sample chamber, a lysis reagent chamber, a lysis chamber, a purification reagent chamber, a plurality of PCR reagent chambers, and one or more waste chambers; the method comprising the steps of:

(i) metering a volume of sample from the sample chamber to the lysis chamber;
(ii) metering a volume of lysis buffer from the lysis reagent chamber to the lysis chamber;
(iii) lysing the volume of sample;
(iv) moving the lysate from the lysis chamber to the purification zone;
(v) extracting nucleic acid from the lysate;
(vi) purifying the nucleic acid;
(vii) moving the a purified nucleic acid mixture to the PCR reaction zone;
(viii) contacting the purified nucleic acid mixture with one or more PCR reagents;
(ix) shuttling the mixture formed in step (viii) between the first and second reaction temperature controlled zones;
(ix) repeating steps (viii) and (ix) to form an amplified product mixture;
(x) contacting the amplified product mixture with a detection reagent;
(xi) moving the mixture formed in step (x) to the detection zone; and
(xii) measuring a signal from the detection zone.

Another embodiment of the invention is an assay cartridge configured to purify components of a sample, the assay cartridge comprising a primary fluid path including a purification zone, a purification reagent chamber, and a waste chamber, wherein the purification zone comprises, from a proximal to a distal end, (i) a purification multi-conduit fluidic junction including (a) a first purification reagent chamber conduit connecting the primary flow path and the purification reagent chamber; and (b) a second purification reagent chamber conduit connecting the purification reagent chamber and a purification reagent chamber air vent port; (ii) an integrated purification membrane positioned in the purification zone; and (iii) a waste multi-conduit fluidic junction including (a) a first waste chamber conduit connecting the primary flow path and the waste chamber; and (b) a second waste chamber conduit connecting the waste chamber and a waste chamber air vent port.

Moreover, the invention contemplates a method of purifying a fluid in an assay cartridge comprising a primary fluid path including a purification zone, a purification reagent chamber, and a waste chamber, wherein the purification zone comprises, from a proximal to a distal end, (i) a purification multi-conduit fluidic junction including (a) a first purification reagent chamber conduit connecting the primary flow path and the purification reagent chamber; and (b) a second purification reagent chamber conduit connecting the purification reagent chamber and a purification reagent chamber air vent port; (ii) an integrated purification membrane positioned in the purification zone; and (iii) a waste multi-conduit fluidic junction including (a) a first waste chamber conduit connecting the primary flow path and the waste chamber; and (b) a second waste chamber conduit connecting the waste chamber and a waste chamber air vent port; the method comprising the steps of:

(x) moving a volume of fluid through the membrane;
(y) removing a volume of fluid eluted in step (x) to the waste chamber;
(z) moving one or more volumes of purification reagent from the purification reagent chamber through the membrane;
(xx) removing one or more volumes of fluid eluted in step (z) to the waste chamber; and
(yy) eluting a purified volume of fluid from the membrane.

The invention further provides an assay cartridge configured to conduct a reaction using a sample processed in the cartridge, the assay cartridge comprising a primary flow path including a reaction zone, wherein the reaction zone comprises a first reaction temperature controlled zone and a second reaction temperature controlled zone and the primary flow path is configured to shuttle a volume of fluid between the first and second reaction temperature controlled zones during a reaction conducted in the reaction zone, wherein the primary flow path is intersected at the reaction zone by one or more reagent multi-conduit junctions connecting (i) the primary flow path and one or more reaction reagent chambers; and (ii) the one or more reagent chambers and one or more reagent chamber air vent ports.

In addition, the invention provides an assay cartridge configured to detect a component of a metered volume of fluid in the cartridge, the cartridge comprising a one or more detection reagent chambers and a primary flow path including a detection zone, wherein the detection zone is intersected by a detection reagent multi-conduit junction connecting (i) the primary flow path and the one or more detection reagent chambers; and (ii) the one or more detection reagent chambers and one or more detection reagent air vent ports.

Moreover, the invention includes a fluidic network comprising a chamber connected to an air vent port, the fluidic network comprising a primary flow path and one or more fluidic conduits each intersecting the primary flow path and fluidically connecting the primary flow path to the chamber, wherein the fluidic network is configured to meter a volume of fluid in the network. Also provided is a system configured to interface with a fluidic network as described herein.

BRIEF DESCRIPTION OF THE DRAWINGS

FIG. 1(a) is a schematic representation of the fluidic network and reagent storage and processing zones within the cartridge.

FIGS. 2(b-c) show the position of vent ports in one embodiment of a cartridge of the invention. FIG. 2(c) is a cross-sectional view of the manifold interface port shown in FIG. 2(b), which depicts an aerosol barrier incorporated into the cartridge at the point where the manifold mates with the cartridge.

FIGS. 3(c-d) depict cross-sectional views of an embodiment of the design for an extraction filter used in the purification zone. Panel (c) shows that the design is composed of three components, i.e., a top, GFD filter, and base. The top carrier has a knife edge that both cuts the extraction filter and serves as an energy director for ultrasonic welding to the base. Panel (d) shows the configuration of the filter after ultrasonic welding. The knife edge melts during ultrasonic welding and forms the weld bead. The thickness of the filter, the depth of the recess in the top carrier, and the depth of the weld determine the amount of filter compression.

FIGS. 3(f-g) illustrate two non-limiting examples of configurations for reagent reconstitution chambers in the cartridge.

FIGS. 6(a-b) show heating elements in the heating block of an exemplary reader of the invention.

FIG. 6(c) shows one embodiment of a cartridge and the various temperature controlled zones within.

FIGS. 12(a-b) provides PCR amplification results for nucleic acids spiked into clean buffer, whole blood or a solution containing 1 ug/uL humic and fulvic acids. One hundred (100) fg of DNA from B. anthracis was spiked into PBS (buffer only), whole blood (Blood spike), or a buffer sample containing 1 ug/uL humic acid and fulvic acid (humic Spike).

FIG. 13 shows the CT values for real-time analysis of eluted product from the mini-column prototype using the lysis procedure described here.

FIG. 14 shows the final primer sequences used to amplify gene targets.

FIGS. 15(a-b) shows that addition of tRNA completely reverses the inhibitory effect of RT enzyme on PCR. Panel A shows the amplification of a DNA target (FT) using our 16-plex primer mix and a one step RT and PCR protocol (all primers for DNA and RNA targets present during RT step). Panel B shows the amplification of the same DNA target (FT) using two step RT and PCR protocol (only the reverse primers for the RNA targets were present during the RT step and remaining primers were added after completion of RT step.

FIG. 15(c) shows the results of an experiment using a model 6-plex PCR assay to examine the tradeoff between PCR cycle duration and the number of PCR cycles that can be run in a 15 min amplification reaction.

FIG. 16(a) shows that for the BA-PA target, an annealing temperature of 56° C. and a cycle dedicating 60% of cycle time to the anneal/extend step gave optimal amplification when using a fast (20 sec.) overall cycle time. The graph also shows that these values provide good robustness to small changes in temperature or anneal/extend time.

FIG. 16(b)-(e) show that the optimal denaturation temperature for fast PCR cycles was between 95 to 97° C.

FIG. 18 is a table of amplification efficiencies measured in the flow cell prototype for each of our 16 targets.

FIG. 20(a) shows the final probe sequences used to detect PCR amplicons.

FIG. 20(b) shows the sequences of PCR primers prepared by shifting the position of one of the primers on the target sequence to shorten the length of the amplicon and remove nucleotides involved in secondary structure formation.

FIG. 21(a-b) show the effects of these strategies on signals for the VEE 5'UTR and NSP4 targets.

FIG. 22(a-b) demonstrate the performance of our optimized 16-plex ECL sandwich hybridization assays in the multi-well plate format and the observed levels of cross-reactivity of each target for the different capture probes.

FIG. 23(a-b) shows ECL signals for measuring amplicons from a model 6-plex panel (our 6 genetic targets for BA, FT and YP).

DETAILED DESCRIPTION

Figure 1B:
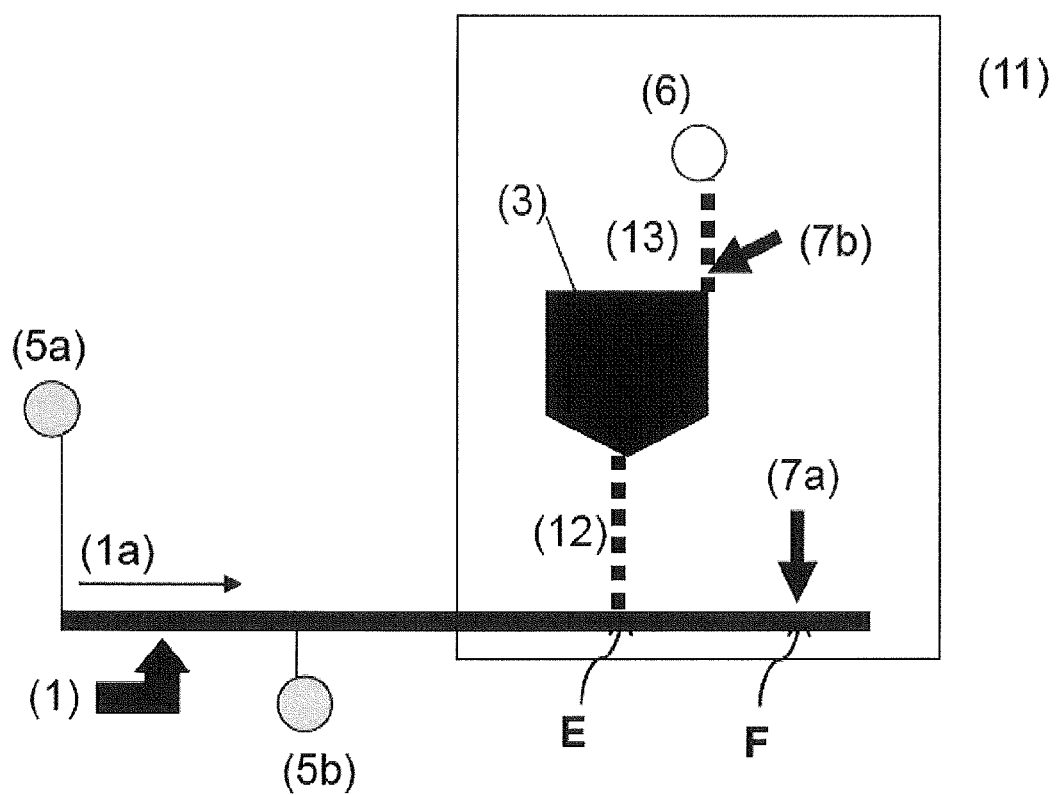
FIG. 1(b) is a schematic representation of a multi-conduit fluidic junction.

The invention, as well as additional objects, features and advantages thereof, will be understood more fully from the following detailed description of certain preferred embodiments. Where the terms "measure" or "measurement" are used herein, they are understood to encompass quantitative and qualitative measurement, and encompasses measurements carried out for a variety of purposes including, but not limited to, detecting the presence of a thing or property, measuring the amount of a thing or property, and/or identifying a thing or property in a sample. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention relates to assay cartridges, systems, and methods of using the same, wherein the cartridge includes a fluidic network and one or more chambers and zones for conducting a multiplexed nucleic acid measurement on a biological fluid sample. In particular, the assay cartridge of the present invention is configured to conduct one or more steps of a nucleic acid measurement, e.g., cell lysis, nucleic acid extraction, purification, amplification, and detection of PCR amplicons. The cartridge can be used in an assay system including a reader configured to interface with the cartridge. One embodiment of the reader includes an enclosure, a cartridge tray and a mounting frame positioned within the enclosure to align the cartridge with one or more reader components, including but not limited to an optical detection assembly, an ampoule breaking mechanism, an electrode contact pin assembly, a fluidic control manifold configured to enable fluid motion within the fluidic network of the cartridge, one or more optical sensors for fluidic control, and one or more heater assemblies.

The assay cartridge can include the necessary electronic components and/or active mechanical components for carrying out an assay measurement, e.g., one or more sources of electrical energy, ammeters, potentiometers, light detectors, temperature monitors or controllers, pumps, valves, etc. Preferably, some or all of the electronic and/or active mechanical components are arranged within a separate reader. The reader can also include the appropriate electrical, hydraulic, fluidic and/or optical connections to the assay cartridge for carrying out an assay on the assay cartridge. Using such an arrangement, the assay cartridge can be designed to be low cost and disposable while the reader (which holds the more expensive and complex components) is reusable. A preferred assay procedure using the assay system of the invention comprises inserting the cartridge in the reader, which makes the appropriate electrical, fluidic and/or optical connections to the cartridge (making use of electrical, fluidic and/or optical connectors on the cartridge and reader), and conducting an assay in the cartridge. The sample is preferably introduced into the cartridge prior to inserting the cartridge in the reader. The assay can also involve adding one or more assay reagents to the cartridge, but in a preferred embodiment, one or more assay reagents are stored in the cartridge in a dry and/or wet form.

The assay cartridge of the present invention preferably includes all the required reagents and fluidic features to carry out all the steps required to process and analyze a sample. FIG. 1(a) is a schematic representation of the fluidic network and reagent storage and processing zones within the cartridge. The fluidic network within the cartridge can include a primary flow path (1) and one or more fluidic conduits (2), connecting the primary flow path to one or more chambers (3) for reagents and other materials/operations used and/or conducted in the cartridge during the conduct of an assay. The primary flow path includes an inlet (4), a purification zone (depicted in FIG. 1(a) between points A and B along the primary flow path), a reaction zone (shown in FIG. 1(a) between points B and C along the primary flow path), and a detection zone (shown in FIG. 1(a) between points C and D along the primary flow path). In addition, the primary flow path also includes one or more air vent ports (5). The fluidic conduits intersect the primary flow path and connect a chamber to the primary flow path as well as each chamber to an additional air vent port (6). The fluidic network is configured to meter a volume of fluid in the primary flow path.

As shown in FIG. 1(a), the cartridge can include a plurality of chambers (3a-3f), for example, a sample chamber (3a), a mixing chamber (3b), one or more liquid and/or dried reagent chambers (3c-f), and one or more waste chambers (8a-b). The chambers are connected to the primary flow path via a plurality of fluidic conduits, so that a sample introduced into the sample inlet can be routed to a sample chamber, and a metered volume of sample can be sequentially delivered to and processed in one or more chambers/zones intersecting and/or positioned along the primary flow path. The vent ports are positioned in the fluidic network in fluidic communication with the various chambers, purification, reaction, and detection zones (directly or through vent conduits) so as to allow the equilibration of fluid in the chambers with the atmosphere or to allow for the directed movement of fluid into or out of a specified chamber/zone by the application of positive or negative pressure.

In a specific embodiment, a fluidic conduit within the fluidic network includes a multi-conduit fluidic junction (11) as shown in FIG. 1(b) including (i) a first conduit (12) connecting the primary flow path and a chamber (3), and (ii) a second conduit (13) connecting the chamber to the additional air vent port (6), wherein the first conduit is in communication with an optical fluid sensor (7a) at a position distal from the fluidic junction, i.e., the point at which the primary flow path is intersected by the first conduit (represented in FIG. 1(b) as point E). The direction of fluid flow is shown by arrow (1a). In one embodiment, fluid is directed through the primary flow path (1) and when the fluid flow reaches optical sensor (7a) (point F), i.e., the optical sensor in communication with the first fluidic conduit of the multi-conduit fluidic junction (11), the fluid flow path is vented to atmospheric pressure by vent (5a), stopping fluid flow at point F. As vent (5a) is opened, vent (5b) remains closed. Once fluid flow at point F is stopped, vent (5a) is closed and air is introduced by vent (5b) to push fluid upstream in the primary flow path (1). This method generates a metered volume of fluid wherein the volume is defined by the distance between the intersection of the vent (5b) and the primary flow path, and the optical sensor in communication with the junction (point F). The sample chamber fluidic junction is also in communication with a sample chamber optical fluid sensor (7a) at a position distal from the sample chamber fluidic junction and a metered volume of fluid traversing the fluidic network is alternatively defined by the distance between the sample chamber fluidic junction and the distal position. As discussed in more detail below, in this alternate embodiment, once the fluid front in the primary flow path reaches an optical sensor in communication with a multi-conduit fluidic junction, the fluid front can be backflowed into the chamber of the junction. The contents of the chamber can then be reintroduced into the primary flow path and directed in the forward direction along the primary flow path to a subsequent chamber/zone in the cartridge. Hence, the volume of fluid metered in the fluid flow path is defined by the geometry of the microfluidic channel.

Each of the chambers within the cartridge interface with the primary flow path via a multi-conduit fluidic junction as shown in FIG. 1(b). As described above, fluid can be directed along the primary flow path in the forward or reverse direction, with the direction of fluid flow being controlled by the vent ports positioned in the fluidic network. The vent ports act as control ports that allow a reader to control the movement of fluid in the cartridge, e.g., by a combination of sealing one or more ports, opening one or more ports to atmospheric pressure, connecting one or more ports to a source of positive pressure, and/or connecting one or more ports to a source of negative pressure.

Likewise, if the chamber is a mixing chamber, the metered volume of fluid is directed along the primary flow path into the chamber via the first fluidic conduit, where it can be mixed with one or more reagents and subsequently redirected to the primary flow path. A mixing chamber can also be connected to one or more reagent chambers and a metered volume of reagent can be directed into the mixing chamber, before or after a metered volume of sample is introduced to the mixing chamber. Hence, the primary flow path is intersected by a mixing chamber multi-conduit junction including (i) a first mixing chamber conduit connecting the primary flow path and the mixing chamber, and (ii) a second mixing chamber conduit connecting the mixing chamber to a mixing chamber vent port. In a preferred embodiment, the mixing chamber fluidic junction is in communication with a mixing chamber optical sensor at a position distal from the mixing chamber fluidic junction and the metered volume of fluid traversing the primary flow path is defined by the distance between the mixing chamber junction and the distal position. In a preferred embodiment, the primary flow path further comprises a series of Z-transitions at a position distal from the mixing chamber fluidic junction to facilitate mixing of the sample and reagent(s) added to the sample.

The fluidic network meters a volume of reagent from a reagent chamber as described above in reference to FIG. 1(b), i.e., the contents of the reagent chamber are released into the first conduit and flow into the primary flow path until the reagent reaches an optical sensor in communication with the multi-conduit fluidic junction connected to the reagent chamber. When the reagent fluid front reaches the optical sensor, a vent in the flow path is opened to atmospheric pressure to stop the reagent fluid front at the optical sensor, the vent is closed and a secondary vent is opened to direct the metered volume of fluid to flow in the desired direction. In the embodiment shown in FIG. 1(b), the fluid front in the primary flow path reaches optical sensor (7a) and is back-flowed into the chamber (3). Thereafter, the contents of chamber (3) are reintroduced into the primary flow path and directed in the forward direction along the primary flow path to a subsequent chamber/zone in the cartridge. The chamber can also include an overflow optical sensor (7b) and as described herein and illustrated in FIG. 1(b).

Vent ports are preferably apertures on the surface of the cartridge that are in fluidic communication with fluidic chambers or conduits within the cartridge. In a laminated cartridge construction, the vent ports can be provided, for example, by apertures in cover layers that seal against a cartridge body to define planar fluidic networks or alternatively, by through-holes exposed on one surface of the cartridge body that communicate with fluidic networks on the opposing side. The vent ports can also be used to introduce air into liquid streams passing through the fluidic conduits of the invention, for example, to segment the fluid streams with slugs of air. The introduction of air can be used to prevent mixing of two liquid slugs passed sequentially through a conduit, to clear a liquid from a conduit and/or to enhance the efficiency of a wash step. Preferably, the vent ports are arranged in a single row at a common location along the cartridge body's width. Such an arrangement and configuration of the control points advantageously allows the interface between the reader and the cartridge to be simplified. For example, using such a preferred configuration allows the reader to make use of a single fluidic mating device for placing the cartridge into fluidic communication with the reader. Such a configuration also allows the motion control subsystem(s) to be simplified in that a single motor or actuation device can be used to actuate the fluidic mating device and move it into sealing engagement with the cartridge body.

The fluidic conduits can be located at any position within the cartridge and oriented at any angle. Advantageously, the fluidic channels are located, primarily, in planar networks, preferably located proximate to the outside surfaces to allow for a multi-layered cartridge design that uses, e.g., machined, die-cut, laser-cut and/or molded cartridge body components. Preferred conduit geometries include conduits with cross-sections that are circular, semi-circular, oval, square or rectangular in cross-section. The width is, preferably, similar to the height so as to minimize the surface area for a particular cross-sectional area. Width and height can vary widely from nm to cm ranges depending on the application, sample volume and cartridge design. Preferred ranges for the width and height are 0.05 to 10 mm, preferably, 0.25 to 3 mm, most preferably 0.5 to 2 mm. Cartridges adapted to low volume samples such as blood from finger pricks can have small conduits, preferably having height/widths<1 mm, preferably between 0.25 to 1.0 mm.

The fluidic channels preferably include "Z-transitions" to route the fluid flow path between planes in the cartridge. A conduit with such a Z-transition can comprise first, second, and third conduit segments arranged in sequence, the first and third conduit segments being located in different planar fluidic networks and a second conduit segment connecting the two fluidic networks and arranged at an angle to the other two segments. By way of example, Z-transitions route the fluid flow/path from fluidic conduits near the upper surface to fluid conduits near the bottom surface and vice versa. Z-transitions are advantageous in that they provide capillary breaks (as described below) and allow for more complicated fluidic networks than would be possible if the fluidic conduits were confined to one plane. Z-transitions can be used to passively control the flow of fluids and prevent mixing of fluid streams. Certain embodiments of the invention employ "double Z-transitions," that is conduits that comprise a first Z-transition that directs fluid flow from a first planar network to a second planar network, a second Z-transition that redirects fluid flow back to the first planar network and a connecting segment in the second planar network that connects the two Z-transitions. Such a double Z-transition can comprise first, second, third, fourth and fifth conduit segments arranged in series, the first and fifth segments located in a first planar fluidic network, the third segment located in a second planar fluidic network, the second and fourth segments located so as to direct flow between the two planar networks. A double Z-transition can be used to traverse a channel without interruption ("jumping over" a channel) or to cross another type of boundary.

The fluidic network can be formed within the cartridge in a number of different ways, dependent, in part, upon the materials chosen for the cartridge. Any known fabrication method appropriate to the cartridge body material can be employed including, but not limited to, stereolithography, chemical/laser etching, integral molding (i.e., channels are formed as the part is being molding during manufacturing), machining, lamination, etc. Such fabrication methods can be used alone or in combination. In certain embodiments of the invention, the cartridge comprises a cartridge body and one or more cover layers mated to surfaces of the cartridge body so as to define one or more fluidic networks (preferably, planar fluidic networks) there between. Similarly, Z-transitions and/or ports can be selectively molded into, or machined out of, the cartridge body at predetermined locations to form the fluidic connections between the channels on the upper and lower surfaces.

One preferred embodiment of the cartridge can be fabricated using a "lamination" process whereby the cartridge body's functional surfaces are sealed using cover layers to form the fluidic network. For example, recesses (e.g., channels, grooves, wells, etc.) in one or more surfaces of the cartridge body provide what is referred to herein as "functional surfaces." Sealing/mating of the functional surfaces to cover layers forms a fluidic network comprising fluidic components (e.g., conduits, chambers, etc.) at least some of which are defined in part by the recesses in the cartridge body and in part by a surface of a cover layer. The cover layers are preferably comprised of plastic film such as mylar film. The cover layer can be coated with an adhesive to seal the cover layer against the cartridge layer. Other methods for mating the cover layer to the cartridge body will be known to the skilled artisan, e.g., the seal can be achieved by heat sealing, ultrasonic welding, RF (radio frequency) welding, by solvent welding (applying a solvent between the components that softens or partially dissolves one or both surfaces), by use of an intervening adhesive layer (e.g., a double sided adhesive tape, etc.). Advantageously, cartridge features that are created by patterned deposition (e.g., patterned deposition of electrode or dielectric layers and/or patterned deposition of reagents to form dry reagent pills or to form binding domains with immobilized binding reagents) are created on cover layers so as to take advantage of automation available to process plastic film in large sheets or rolls.

Recesses can be, for e.g., molded in, etched in or machined from the cartridge body. By analogy, fluidic components can also be defined, at least in part, by recesses in a cover layer that is mated to a cartridge body. Fluidic components can also be defined, at least in part, by regions cutout from gasket layers disposed between the cartridge body and cover layers. Apertures in the cartridge body and/or cover layers can be used to provide for access ports to the fluidic network, e.g., sample introduction ports, vent ports, reagent addition ports and the like. Vent ports, preferably, allow the equilibration of fluid in the chambers with the atmosphere or to allow for the directed movement of fluid into or out of a specified chamber by the application of positive or negative pressure. In a preferred embodiment, fluid is moved in the fluidic network by applying positive or negative air pressure, without directly applying pressure on the fluid front. Vent ports, preferably, are designed to prevent the leakage of liquid samples or reagents through the ports and can include aerosol-resistance filters, membrane or filter materials that permit air flow but act as barriers to aqueous solutions (e.g., filter or membranes made from porous hydrophobic materials such as Gore-Tex®), and materials that are porous to air but seal when they come in contact with aqueous solutions (e.g., cellulose gum impregnated filters).

Preferred embodiments include a cartridge having a cartridge body with a first side and a second, preferably opposing, side and one or more cover layers mated to the first side to form a first fluidic network there between and one or more cover layers mated to the second side to form a second fluidic network there between. Through-holes through the cartridge body (which can be formed by molding, etching, machining, etc.) can be used to link the first and second fluidic networks and to provide Z-transitions. Additional fluidic complexity can be built into a cartridge by employing a laminated cartridge body having multiple cartridge body layers and additional fluidic networks between these layers; through-holes through the various cartridge body layers are used to link the different fluidic networks.

A high degree of control over the movement of liquids in the cartridges of the invention can be attained, without the introduction of active valve elements in the cartridge, through the use of fluidic networks comprising capillary breaks. "Capillary break," as used herein, refers to a region in a fluid conduit that acts as a barrier to liquid moving through the conduit under capillary action or under the driving force of a low pressure gradient below a threshold pressure. In preferred examples of capillary breaks, application of a pressure above the threshold pressure acts to push the fluid past the barrier. Capillary breaks can be designed into fluid conduits by introducing, e.g., i) a transition, on a surface of a conduit, from a wettable surface to a less wettable surface (e.g., as indicated by the contact angle for water); ii) a transition in conduit width from a region of narrow width that promotes capillary flow to a region of wider width; iii) a transition, on a surface of a conduit, in roughness; iv) a sharp angle or change in direction and/or v) a change in cross-sectional geometry. In another embodiment, a fluid conduit has a flexible wall/diaphragm that impinges into the conduit and blocks flow driven by a pressure below a threshold pressure. Application of a higher pressure forces the flexible wall/diaphragm out of the flow path and lets fluid flow. In one embodiment, the diaphragm is made of a material (e.g., Gore-Tex®) that allows gas to pass through but prevents the flow of liquid up to a certain pressure. Preferred capillary breaks involve a sharp angle or change in direction in a fluid conduit.

In one embodiment of the invention, a liquid is introduced into a chamber comprising an outlet conduit that includes a capillary break (preferably a Z-transition). The liquid enters the outlet conduit but stops at the Z-transition. A pressure gradient is then applied (e.g., by applying positive pressure to the chamber or negative pressure to the other end of the conduit) which cause the liquid to flow past the Z-transition into the rest of the conduit.

The sample chamber (3a) is adapted to receive a sample to be analyzed in the cartridge. The sample chamber includes a sample introduction port for introducing sample into the chamber (with regard to the design of the sample introduction port, reference is made to U.S. Ser. No. 10/744,726, filed Dec. 23, 2003, and FIGS. 35(a-b) and 47(a-b) and accompanying text of U.S. Ser. No. 12/959,952, filed Dec. 3, 2010, the disclosures of which are hereby incorporated herein by reference). The port is preferably an opening in the cartridge that provides access to the sample chamber. Alternatively, the port can be a membrane or septa through which a sample can be injected into the sample chamber, e.g., through the use of a needle or cannula. Preferably, the cartridge also includes a sealable closure for sealing the sample introduction port and preventing leakage of the sample and possible exposure of the user and/or associated instruments to biohazards. Preferably the sealing/capping mechanism utilizes a hinged configuration so that the sample chamber is easily accessed and sealed. In particularly preferred embodiments the sealing/capping mechanism incorporates a flexible hinge, e.g., rubber, plastic or the like. Most preferably, the sample chamber is adapted and configured to receive a modular detachable insert that includes a cap for sealing the sample chamber. Use of a modular detachable insert within the sample chamber also allows for independent selection of materials for the main cartridge body. In an alternative embodiment, sealing of the sample introduction port is achieved by applying an adhesive tape to the port. The sample chamber can contain dry reagents used in carrying out the assay that reconstitute on addition of a liquid sample.

The sample chamber can also include a filter for, e.g., removing particulate matter that can be present within the sample itself or that can be present as a result of using a swab or the like to introduce sample into the sample chamber. A preferable embodiment can employ a filter that not only removes any particulate matter but that is also designed to separate red blood cells (RBC) from blood plasma; e.g., where the particular assay/assay format requires blood plasma as the sample. Such a filter can be an integral cross-flow filter, in-line filter or the like. Preferably, the filter is arranged at or near the entrance of the sample conduit. As described above, the sample chamber is connected to the primary flow path by a sample chamber multi-conduit fluidic junction including (i) a first sample chamber conduit connecting the primary flow path and the sample chamber; and (ii) a second sample chamber conduit connecting the sample chamber to a sample chamber air vent port via an overflow waste chamber. A liquid sample is added to the sample chamber and the operator closes the cap. After sample addition, the cartridge meters a pre-defined volume of sample for processing. After the sample volume is metered, the fluid slug is moved into a mixing chamber (3b), where it is combined with a metered volume of reagent stored in reagent chamber (3c).

The reagent chambers are adapted to hold liquid reagents used during sample processing (with regard to the design of reagent chambers in a cartridge, reference is made to U.S. Ser. No. 10/744,726, filed Dec. 23, 2003, and Ser. No. 12/959,952, filed Dec. 3, 2010, the disclosures of which are hereby incorporated herein by reference). Liquid reagents that can be held in a reagent chamber include buffers, assay diluents, solutions containing binding reagents (e.g., proteins, receptors, ligands, haptens, antibodies, antigens, nucleic acids and the like), solutions containing enzymes and/or enzyme substrates, solutions containing control reagents, ECL read buffers containing ECL co-reactants (e.g., tertiary amines such as piperazine-N,N'-bis(2-ethanesulfonic acid) and tripropylamine), wash solutions, antifoam agents, extraction reagents (e.g., solutions containing detergents, acids, bases, etc.) and the like. A cartridge can have one, two or more reagent chambers depending, for e.g., on the number of reagents required for sample processing in the cartridge and/or by the assay format. The reagent chamber is connected to the primary flow path as described above and as illustrated in FIG. 1(b). Optionally, a filter element is placed before or in the reagent conduit, e.g., if the reagent solution is expected to contain particles that can clog the cartridge fluidics or otherwise negatively affect assay performance.

Preferably, where an assay requires the use of liquid reagents, some or all of these liquid reagents are stored in liquid form in reagent chambers so as to minimize the number and complexity of the operations that must be carried out by a user or reader. In one preferred embodiment the reagent chamber(s) can be filled with the requisite assay reagent(s) at the time of cartridge manufacture and subsequently sealed. When used to store liquid reagents, the reagent chambers should be designed to prevent leakage and/or evaporative loss of the reagents from the chambers during storage. In a preferred embodiment, an assay reagent release mechanism would be incorporated within the reader for releasing the assay reagent from the reagent cartridge. The assay reagent release mechanism is preferably adapted and configured to engage the reagent chamber and release/recover its contents.

The reagent chamber is a container such as an ampoule (e.g., glass, plastic, or the like), a pouch (e.g., plastic, metal foil, plastic/metal foil laminates, rubber, or the like), a blister pack, a syringe, or the like, or any other container that can be filled with fluid, sealed and dropped into the cartridge for subsequent fluid delivery. Preferred materials include glass, plastics with good water vapor barrier properties (e.g., cyclic olefin copolymers such as copolymers of ethylene and norbornene, nylon 6, polyethyelene naphthalate, polyvinylidene chloride and polychlorotrifluoro-ethylene) and metal foil/plastic laminates because of their chemical inertness and their resistance to evaporative losses; other suitable materials will be apparent to the skilled practitioner. Ampoules preferably comprise a material that can be made to shatter or break on impact such as glass or hard plastic. Embodiments incorporating breakable ampoules preferably also include filters to ensure that substantially all of the fragments that can result upon rupturing the ampoules are not permitted to enter the fluidic network and possibly obstruct/block fluid flow. The reagent chambers include an outlet port (or drain) for transferring reagent out of the reagent chamber. The outlet can include a filter element for preventing glass shards from entering the cartridge fluidics.

Optionally, ampoules are used as reagent chambers and the ampoules rest in an ampoule cradle adapted to receive a cylindrical ampoule (with regard to the design of an ampoule cradle, reference is made to FIG. 36 and the accompanying text of U.S. Ser. No. 12/959,952, filed Dec. 3, 2010, the disclosure of which are hereby incorporated herein by reference). The ampoule cradle, i.e., a reagent chamber, includes side walls and a plurality of support brackets protruding from the side walls, and the support brackets are configured to provide a multi-point cradle support for a cylindrical ampoule. The reagent chamber can include three, four or more support brackets, protruding from the side walls, at least one bracket being present on each side of the chamber. The brackets are, preferably, sloped inward such that the width of the reagent chamber becomes narrower with increased depth in the well (in which case, the side walls themselves do not need to be sloped). In one embodiment, the side walls of the chamber are also sloped. The brackets provide a multi-point cradle support for the ampoules (e.g., a three or four point cradle design) that allows for significant tolerance in the length of the ampoules. The surface of the supports that contact and support the ampoule can be slanted (as shown) or flat. The width of the brackets (i.e., the dimension along the length of the chamber) can be narrow (e.g., <5 mm or less than 2 mm) to focus forces on relatively small regions of the ampoule during ampoule breaking.

An important consideration for cartridge based assay systems relates to long term storage of the cartridge prior to use; i.e., "shelf life" of the cartridge. Certain assay reagents (especially biological reagents and/or binding reagents such as enzymes, enzyme substrates, antibodies, proteins, receptors, ligands, haptens, antigens, nucleic acids and the like), when dissolved in a liquid medium require special handling and storage in order to improve their shelf life. In certain instances, even if the assay reagents dissolved in liquid media are handled and stored in strict compliance with the special handling and storage requirements their shelf life is impractically short. Furthermore, the need to observe special handling and storage requirements adds to the complexity and cost of the cartridge based system employing such reagents. The special handling and storage requirements can be substantially reduced, if not eliminated, and the complexity and cost of the system can be minimized by using more stable dry, or dehydrated, forms of the assay reagents. The use of dry reagents can also simplify mixing operations and reduce the volume and weight of a cartridge. Reagents that can be included in dry form include biological reagents, binding reagents, pH buffers, detergents, anti-foam agents, extraction reagents, blocking agents, and the like. The dry reagent can also include excipients used to stabilize the dry reagents such as sugars (e.g., sucrose or trehalose). For assays that employ acidic or basic samples (e.g., samples that are inherently acidic/basic and/or samples that are extracted or otherwise treated with an acidic/basic reagent), a dry reagent can include a neutralizing reagent (e.g., an acid, base, or a pH buffer).

Dry reagents can be employed in a cartridge in a number of ways. Dry reagents can be stored in a reagent chamber that is filled prior to use by a user or by a reader apparatus. Similarly, dry reagents can be stored in other fluidic components such as within fluidic conduits, along the primary flow path, or in chambers, most preferably within the purification, reaction, and detection zones. In one embodiment, reagents are provided in the form of a dry pill and are retained in reagent reconstitution chambers. Reagent reconstitution chambers are in fluidic communication with the primary flow path, allowing fluid to enter the chamber and dissolve the dried reagent pill. In one embodiment, a reagent reconstitution chamber has a fluid inlet at the bottom of the chamber (or below the location of the pill) and a vent located at the top of the chamber (or above the location of the pill). The chamber holds a pill between the inlet and the vent but, preferably, provides fluid paths around the pill to allow for facile introduction of fluid into the chamber without pressure build-up. The pill may be held between the inlet and the vent by pill retaining features defined by the chamber walls. The pill retaining feature can be a cradle defined by sloping brackets (as described above in the context of features for holding ampoules). Alternatively, the walls of the chamber are shaped to conform to the shape of the pill and, preferably, taper down towards the bottom of the chamber to provide a seat that firmly holds the pill through multi-point contacts. In this case, fluidic paths around the pill can be provided by distorting the shape of the walls so that they are not perfectly conformal with the bead or by introducing lobes that break contact with the bead at defined locations. In one embodiment, the bead is spherical or cylindrical and the pill seat is defined by tapered walls that are oblong in cross-section or that are generally circular in cross-section except for the presence of lobes that provide fluid paths around the bead. In one preferred embodiment, the internal diameter near the top of the chamber is at least 0.1" or 0.125" or about 0.15" to permit bubbles formed in the chamber to burst prior to entering the vent. In one specific example, the pill is retained through the use of a chamber with an oblong (39) or tri-lobed (40) wall design, shown in FIGS. 3*f* and 3*g*, respectively.

In operation, a fluid slug is introduced into the reagent reconstitution chamber through the inlet port, while air in the chamber exists through the vent port. The fluid slug volume is selected to reach and, preferably, completely immerse the pill, but not reach the vent port. The dry pill is dissolved in the fluid slug. The fluid slug, now containing the dry reagents, is then removed back through the inlet. Optionally, reconstitution and mixing of the reagent in the slug can be aided by repeatedly pulling the slug in and out of the chamber through the inlet or, after introduction of the slug into the chamber, by introducing air through the inlet to form bubbles that pass through the fluid in the chamber and out the vent port.

In an alternate embodiment, a fluid slug is introduced into the chamber to dissolve the dry pill and is then removed through the vent port.

Dry reagents can be inserted during the manufacture of a cartridge by depositing the dry reagents in the appropriate fluidic component, e.g., by depositing the reagent in the form of a powder or pellet or by incorporating the dry reagent in a screen printed ink. Alternatively, the reagents can be inserted in solution and then dried to remove the solvent. In one preferred embodiment, dried reagents can be formed upon a substrate by depositing solutions containing the reagents in one or more predefined locations and subsequently drying the reagents to form a dried reagent pill under conditions such that on addition of a liquid sample or an appropriate solvent, the dry reagent dissolves into solution. The term "pill" is used herein to refer generally to an amount of a dry, but redissolvable, reagent on a substrate and not to connote any specific three dimensional shape. A pill can be attached to a substrate or free standing. The location of a pill on a substrate is referred to herein as a "pill zone." The substrate is preferably a component of the cartridge, e.g., cartridge body, chamber, cover layer, electrode array, etc. Suitable locations for the pill zone include the sample chamber, reagent chamber, primary flow path, fluidic conduits, and/or reconstitution chambers, so that liquid reagents and samples pick up the dry reagent prior to their introduction to the detection chambers. Alternatively or additionally, reagent pills can be located within the detection zone. In the preferred embodiment, a reagent chamber holds a liquid reagent in an ampoule and a dry reagent pill, so that the dry reagent is reconstituted upon rupture of the ampoule.

A pill zone in which dried reagents are deposited can be prescribed by a boundary which confines the volume of a deposited solution (and, therefore, the dried reagent left after allowing the solution to dry) to a specific region of a substrate. According to one embodiment of the invention, a cartridge comprises a pill zone that is bounded by a boundary surface, the boundary surface being raised or lowered (preferably, raised) and/or of different hydrophobicity (preferably, more hydrophobic) than the pill zone. Preferably, the boundary surface is higher, relative to the substrate surface within the pill zone, by 0.5-200 micrometers, or more preferably by 2-30 micrometers, or most preferably by 8-12 micrometers. Even more preferably, the boundary surface has a sharply defined edge (i.e., providing a steep boundary wall and/or a sharp angle at the interface between the pill zone and the boundary). Preferably, the pill zone surface has a contact angle for water 10 degrees less than the boundary surface, preferably 15 degrees less, more preferably 20 degrees less, more preferably 30 degrees less, even more preferably 40 degrees less, and most preferred 50 degrees less.

In one preferred embodiment the pill zone is defined by a depression cut or molded into the substrate. In another embodiment, the boundary surface around a pill zone is defined by a boundary material applied on the substrate. In one example, the pill zone is defined by a cutout in a film or gasket applied to the substrate, preferably a cutout in a film of adhesive tape. In another preferred embodiment the boundary can be physically defined by applying a coating in a manner which defines the boundary of the pill zone using, e.g., established techniques for forming patterned coatings such as photolithography, patterned deposition, screen printing, etc. In one example, a patterned dielectric coating can be screen-printed onto the surface of a substrate material, the pattern including apertures, the boundaries of which define the pill zone. The reagent can then be dispensed onto the substrate within the pill zone boundary and thereafter dried to form the dried reagent pill.

The waste chambers are adapted to hold excess or waste liquid (with regard to the design of waste chambers, reference is made to U.S. Ser. No. 10/744,726, filed Dec. 23, 2003, and Ser. No. 12/959,952, filed Dec. 3, 2010, the disclosures of which are hereby incorporated herein by reference). Sizing of the waste chambers is preferably done in accordance with the anticipated volume of sample and liquid reagents that will be used in the assay. Another sizing-related factor for the waste chambers that is preferably taken into account relates to the potential for waste fluids, as they enter the waste chamber to foam or bubble. In such instances, where foaming or bubbling is anticipated, the waste chamber volume could be increased sufficiently to avoid any issues that can arise from such foaming or bubbling.

As described above, waste chambers are linked to the primary flow path via a waste chamber conduit and to a vent port (e.g., through a vent conduit). The waste chamber is configured to allow liquid waste to be delivered to the waste chamber through the waste chamber conduit and, preferably, for air that is included in the waste stream to escape through a waste chamber vent port. Optionally, the waste chambers contain a water absorbing material, such as a sponge, that retains waste fluid and prevents leakage of the waste fluid on disposal of a cartridge. A factor that is preferably considered when designing the configuration and arrangement of the waste chambers relates to eliminating or substantially reducing the possibility that fluid from the waste chamber can flow back ("back-flow") into the cartridge's fluidic network.

As described above, sample is added via a sample inlet and stored in the sample chamber. A metered volume of sample is delivered to the mixing chamber into which an additional reagent can be added via a reagent chamber. In a preferred embodiment, a metered volume of reagent is first delivered to the mixing chamber, followed by the addition of a metered volume of sample from the sample chamber. Mixing is facilitated by aerating the contents of the mixing chamber by opening and closing one or more vent ports directly or indirectly connected to the mixing chamber. In a preferred embodiment, the mixing chamber includes an antifoam reagent, for example, SE-15, Antifoam 204, Antifoam A, Antifoam B, Antifoam C, Antifoam Y-30, and combinations thereof (available from Sigma-Aldrich Corp., St. Louis, Mo., www.sigmaaldrich.com). The air which is pumped through the fluid in the mixing chamber displaces an amount of liquid. The mixing chamber is preferably sized and shaped to prevent the escape of liquid into the air vent conduit during aeration and to accommodate fluid flow into and out of the mixing chamber.

As shown in FIG. 1(a), after mixing, the sample is delivered from the mixing chamber to the purification zone for purifying target material in a sample, e.g., nucleic acids, from potential interferents. The basic design is amenable to use with a variety of known approaches for capturing, washing and eluting nucleic acids including approaches that generally target all nucleic acids in a sample (such as binding to glass membranes) as well as approaches that target specific sequences (such as binding to membranes or other solid supports that present specific capture sequences). The purification zone can include a waste chamber (8a), one or more purification reagent chambers (3d-e), and an integrated purification membrane (9). In a preferred embodiment, the purification zone comprises, from a proximal to a distal end, a purification multi-conduit fluidic junction including (i) (a) a first purification reagent chamber conduit connecting the primary flow path and the purification reagent chamber; and (b) a second purification reagent chamber conduit connecting the purification reagent chamber and a purification reagent chamber air vent port; (ii) an integrated purification membrane positioned in the primary flow path of the purification zone; and (iii) a waste multi-conduit fluidic junction including (a) a first waste chamber conduit connecting the primary flow path and the waste chamber; and (b) a second waste chamber conduit connecting the waste chamber and a waste chamber air vent port. The purification membrane can be positioned on a support fit within the primary flow path and the membrane can be compressed prior to cartridge assembly. In a specific embodiment, the membrane comprises a glass fiber membrane.

In operation, a solution containing material to be purified is passed through the membrane under conditions in which the material is bound to the membrane. The remaining solution is collected in the waste chamber. One or more wash buffers are passed through the membrane to remove contaminants and the flow-through is collected in the waste chamber. The washing step with each buffer may be repeated one or more times to improve wash quality. Optionally, the membrane is dried by passing air through it, prior to elution of purified material from the membrane. The purified material is then eluted from the membrane by passing an elution buffer through the membrane.

Some nucleic acid purification methodologies benefit from heating of the purification matrix during elution of nucleic acids and, optionally, during washing of the matrix prior to elution of the nucleic acids. One embodiment of the purification zone includes i) a pre-heating zone that heats the primary flow path to the membrane and/or a ii) a membrane heating zone that surrounds the membrane carrier and heats the integrated membrane. In an more specific embodiment, during the elution of purified material from the membrane (and, optionally, during washing and drying of the membrane), the fluid flowing into the membrane and/or the membrane itself are heated to about 60-80° C., and preferably about 70° C.

The eluate is then directed along the primary flow path to the reaction zone. Reagents required for the conduct of a reaction in the reaction zone can be stored in one or more reagent chambers within the cartridge and/or as dried pills stored within the primary flow path in the reaction zone and/or in one or more reconstitution chambers (10a and 10d). In one embodiment of the invention, a cartridge has one or more reconstitution chambers that are empty or contain only dried reagents. Prior to conducting an assay, the user or reader dispenses liquid reagents into these chambers (e.g., through reagent vent ports or through reagent introduction ports similar to the sample introduction port described above) which, optionally, reconstitute any dried reagent present in the chambers; the reagents are thus prepared for use in the assay. In a preferred embodiment, all reagents are stored in liquid and/or dried form in the cartridge and prior to conducting an assay or a step of an assay, the reader breaks the reagent ampoule(s) to dispense reagent and/or the fluid in the fluidic network reconstitutes dried reagents in the flow path. Sealable closures can be used to prevent leakage of the reagents after their addition. The reaction zone also includes a first reaction temperature controlled zone (10b) and a second reaction temperature controlled zone (10*c*) and the fluidic network is configured to shuttle a volume of fluid between the first and second reaction temperature controlled zones during a reaction conducted in the reaction zone.

The primary flow path leads from the reaction zone outlet to the detection zone. The detection zone is intersected by a detection reagent multi-conduit junction connecting (i) the primary flow path and one or more detection reagent chambers; and (ii) one or more detection reagent chambers and one or more detection reagent air vent ports. The detection zone is adapted for carrying out a physical measurement on the sample. In a preferred embodiment, the detection zone is configured to measure luminescence and in this regard, reference is made to U.S. Ser. No. 10/744,726, filed Dec. 23, 2003, and Ser. No. 12/959,952, filed Dec. 3, 2010, the disclosures of which are incorporated herein by reference. If the measurement requires illumination or optical observation of the sample (e.g., as in measurements of light absorbance, photoluminescence, reflectance, chemiluminescence, electrochemiluminescence, light scattering and the like) the detection zone should have at least one transparent wall arranged so as to allow the illumination and/or observation. When employed in solid phase binding assays, the detection zone preferably comprises a surface (preferably, a wall of the chamber) that has one or more binding reagents (e.g., antibodies, proteins, receptors, ligands, haptens, nucleic acids, etc.) immobilized thereon (preferably, an array of immobilized binding reagents, most preferably an array of immobilized antibodies and/or nucleic acids). In an especially preferred embodiment, the detection zone is an electrochemiluminescence detection zone, most preferably having one or more binding reagents immobilized on one or more electrodes. In one preferred embodiment, the cartridge includes a working electrode having an array of binding reagents immobilized thereon. In another preferred embodiment, the cartridge comprises an array of independently controllable working electrodes each having a binding reagent immobilized thereon. In cartridges employing arrays of binding reagents, at least two elements of the array comprise binding reagents that differ in specificity for analytes of interest. Depending on the detection technology employed in the cartridge, the detection zone can also include a detection temperature controlled region. In a preferred embodiment, the detection zone is an electrochemiluminescence detection zone and the detection zone includes a detection temperature controlled region designed to maintain the temperature of the detection zone between about 20-40° C., preferably 20-35° C., and most preferably 25-35° C.

Depending on the application, manufacturing approach, sample size, etc., the primary flow path dimensions in the detection zone can range from nanometers to tens of centimeters and the volume from picoliters to milliliters. Certain preferred embodiments have widths that can range from 0.05-20 mm, more preferably, 1-5 mm and heights (preferably, less than or equal to the width so as to increase, for a given volume, the surface area of the bottom of the detection zone, especially when this surface is used to immobilize binding reagents) that range from 0.01-20 mm, more preferably, 0.05-0.2 mm. Preferably, the height is less than or equal to the width. Preferably, the detection zone is designed to accommodate sample volumes between 0.1-1000 uL, more preferably, 1-200 uL, more preferably, 2-50 uL, most preferably, 5-25 uL. The primary flow path in the detection zone preferably has a width greater than or equal to the height.

A cartridge can comprise one or more detection regions within the detection zone. Cartridges comprising multiple detection regions can comprise separate fluidic systems for each detection region (e.g., multiple sample chambers and/or reagent chambers and associated fluidic conduits) so that assays on multiple samples can be carried out in parallel. In certain preferred embodiments, multiple detection regions are linked to a single sample chamber and can share the use of other fluidic components such as reagent chambers, waste chambers and the like. In these embodiments, the two detection regions can be used to carry out different sets of assays, thus increasing the number of measurements that can be carried out on a sample relative to a cartridge with one detection region.

In an alternate embodiment employing a plurality of detection regions, one or more of a plurality of detection regions is used as control/calibration region for measuring assay control/calibration samples. In one such embodiment, a first and a second detection region are each configured to carry out a panel of one or more assays for one or more analytes. One detection region (the test region) is used to analyze a sample. The other detection region (the control region) is used to analyze a spiked sample having a predetermined additional amount of the one or more of the analytes of interest (this predetermined additional amount, preferably, being provided by passing the sample through a reagent pill zone comprising the additional amounts). The change in signal between the two regions allows for the calculation of the responsiveness of the signal to changes in analyte and can be used to calibrate the system and/or to determine if the cartridge is functioning properly. In another embodiment employing a control region, the control region is not used to analyze the sample or a derivative thereof, but is used to measure analyte in a separate control or calibrator matrix. The signal in the control region can be used for determining background signals (by using a matrix with no analyte), for calibrating the instrument (by using a calibrator matrix with a predetermined amount of analyte to determine calibration parameters) or to determine if the cartridge is functioning properly (by using a control matrix with a predetermined amount of analyte and determining if the signal falls within a predetermined acceptable range).

Figure 2A:
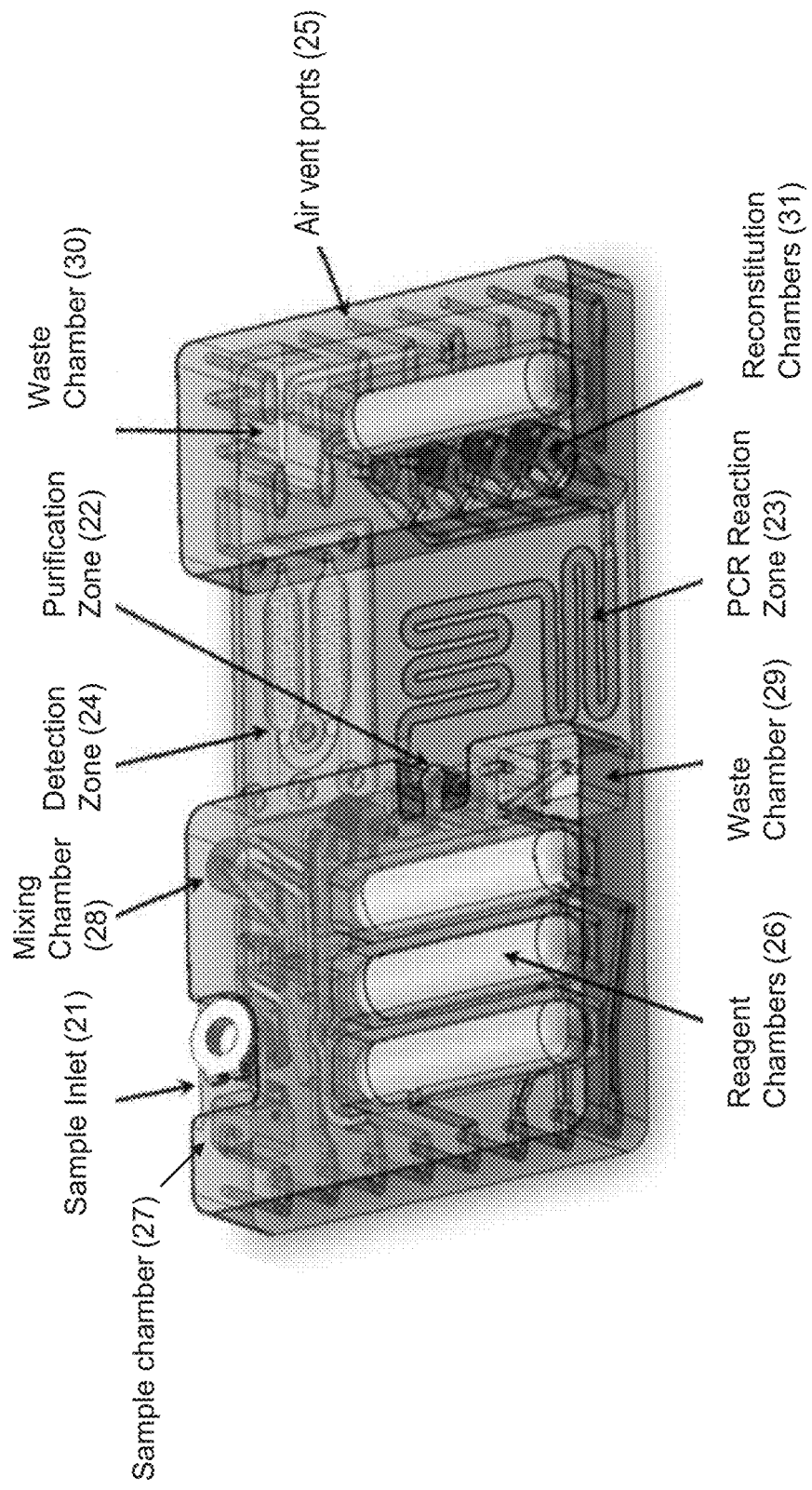
FIG. 2(a) is one embodiment of a cartridge of the invention configured to conduct multiplexed nucleic acid measurements and sample processing, including nucleic acid extraction, purification, amplification, and detection of PCR amplicons.

A preferred embodiment of the invention is depicted in FIG. 2(*a*). The cartridge depicted in FIG. 2(*a*) includes the fluidic network and a plurality of chambers, as described above and illustrated in FIGS. 1(*a-b*). The cartridge is configured to conduct multiplexed nucleic acid measurements and optionally sample processing, including one or more steps of nucleic acid extraction, purification, amplification, and detection of PCR amplicons. In a preferred embodiment, the cartridge is configured to conduct lysis, purification, and elution steps in approximately 15 minutes or less, reverse transcription in approximately 5 minutes or less, amplification in approximately 15 minutes or less, detection reagent binding in approximately 5 minutes or less, and detection in about 5 minutes or less, for a total analysis time of about 45 minutes or less. The cartridge includes a fluidic network such as that described above, including a primary flow path and one or more fluidic conduits, as well as a plurality of chambers for reagents and other materials and/or operations used and/or conducted in the cartridge during the conduct of an assay. The primary flow path includes a sample inlet (21), a purification zone (22), a PCR reaction zone (23), and a detection zone (24). In a preferred embodiment, all amplicons are moved from the detection zone into the waste chamber (30) once detected. In addition, the primary flow path also includes one or more air vent ports (25). Like the cartridge embodied in FIGS. 1(a-b), the fluidic conduits of the cartridge depicted in FIG. 2(a) intersect the primary flow path connecting the chambers to the primary flow path, as well as one or more chambers to an additional air vent port (not shown) and the fluidic network is configured to meter a volume of fluid in the fluidic network within the cartridge. As shown in FIG. 2(a), the cartridge includes a plurality of reagent chambers (26), a sample chamber (27), a mixing chamber (28), waste chambers (29 and 30), and a plurality of reconstitution chambers (31).

As described above in reference to FIGS. 1(a)-(b), as shown in FIGS. 2(b)-(c), vent ports are preferably apertures on the surface of the cartridge that are in fluidic communication with fluidic chambers or conduits within the cartridge. The vent ports act as control ports that allow the reader to control the movement of fluid in the cartridge, e.g., by a combination of sealing one or more ports, opening one or more ports to atmospheric pressure, connecting one or more ports to a source of positive pressure and/or connecting one or more ports to a source of negative pressure. As shown in FIG. 2(b), vent ports are arranged in a row at a common location along the cartridge body's width. Such an arrangement and configuration of the control points advantageously allows the interface between the reader and the cartridge to be simplified. Manifold interface ports are preferably located in a row(s) on the periphery of the cartridge along both sides as shown in FIG. 2(b) (25a and 25b).

FIG. 2(c) is a cross-sectional view of the manifold interface port shown in FIG. 2(b) (25c), which depicts an aerosol barrier incorporated into the cartridge at the point where the manifold mates with the cartridge. The aerosol filter minimizes contamination by aerosols that could be generated during analysis. In one embodiment, the aerosol barrier achieves greater than 95% filter efficiency, and preferably greater than 99% filter efficiency, down to less than 0.75 um, and preferably less than 0.50 um. In one embodiment, the aerosol barrier comprises a 10 um pore size filter available, e.g., from Porex. Preferably, the aerosol barrier is built into the consumable rather than the reader so that the manifold interface of the reader does not become contaminated.

Figure 3A:
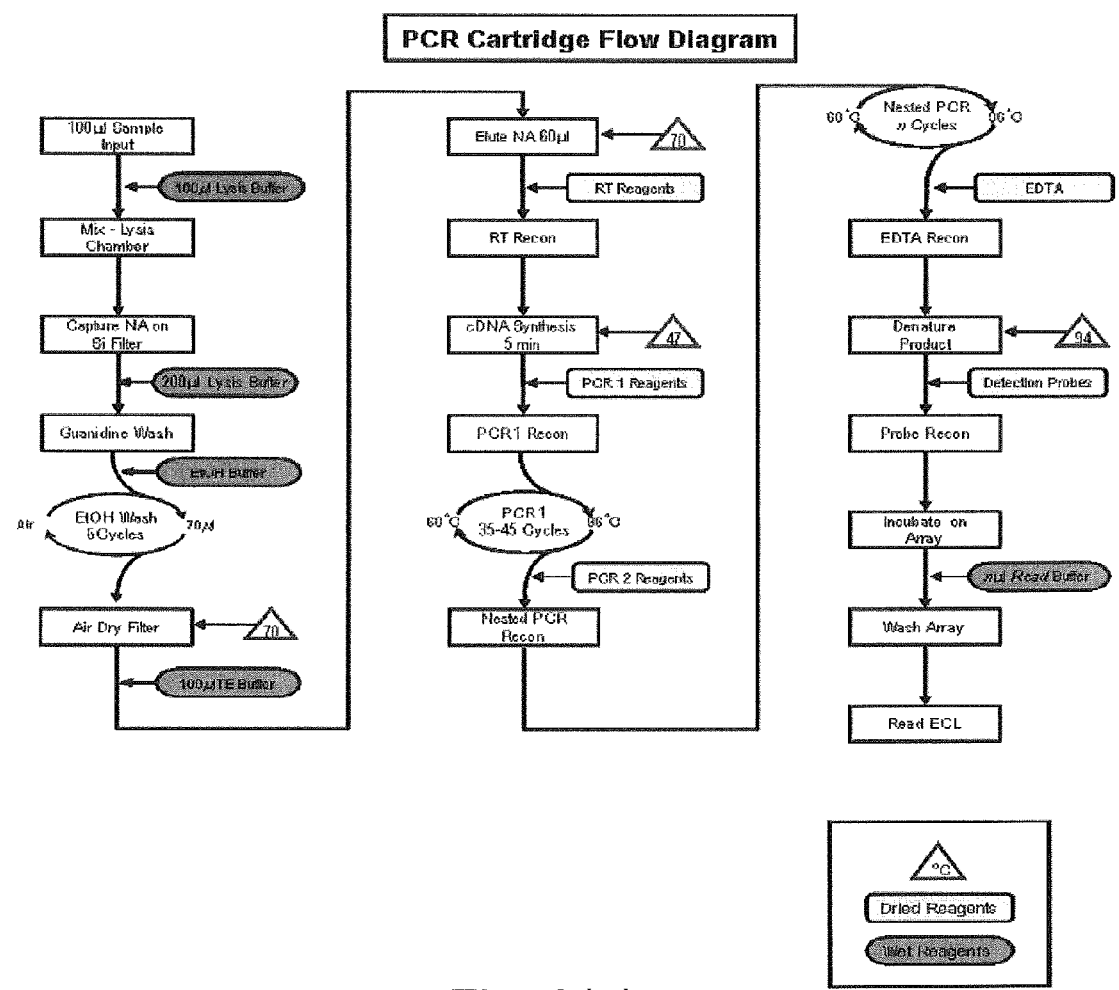
FIG. 3(a) is a detailed flow diagram of the operation of the cartridge depicted in FIG. 2(a).
Figure 3B:
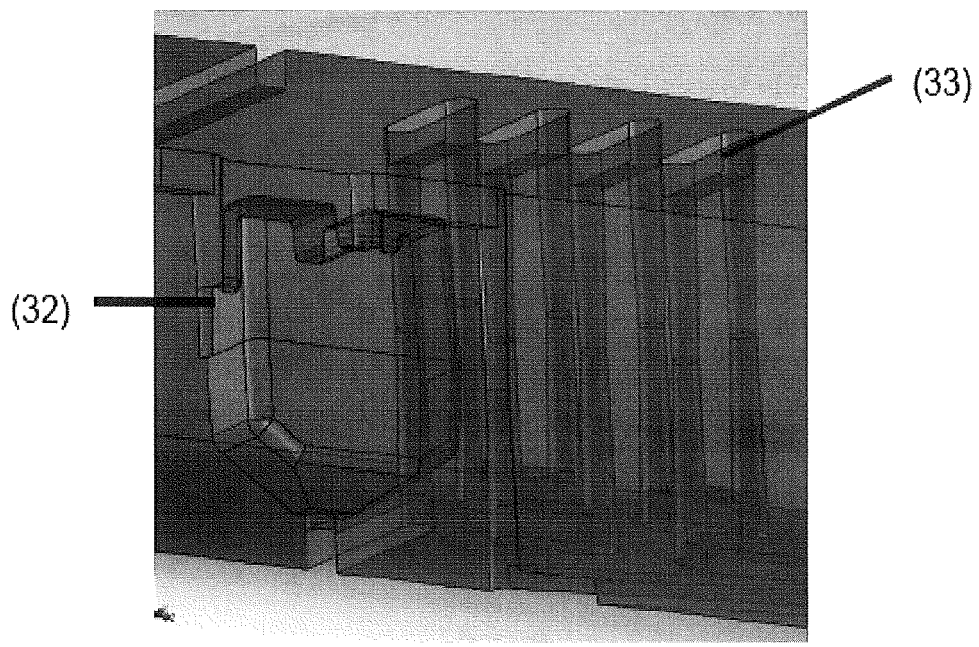
FIG. 3(b) shows one embodiment of a lysis chamber, including an inlet port and a series of "Z transitions" at the exit of the lysis chamber for mixing the sample and lysis buffer.

A detailed flow diagram of the operation of the cartridge depicted in FIG. 2(a) is provided in FIG. 3(a). A liquid sample is introduced to the sample inlet which is fluidically connected along the primary flow path to the sample chamber. The cap on the sample inlet is sealed. After sample addition, the cartridge meters a volume of lysis buffer to the mixing chamber (lysis chamber), and the cartridge subsequently meters a volume of sample to the mixing chamber. Mixing of the contents of the mixing chamber is facilitated by aerating the contents of the mixing chamber via one or more of the vent ports connected directly and/or indirectly to the mixing chamber. In addition, mixing can be further facilitated by the addition of a series of Z-transitions in the primary flow path at a position distal to the mixing chamber fluidic junction, as shown in FIG. 3(b) (and preferably at a position following position 7a in FIG. 1(b)). The solution in the lysis chamber (32) is moved through the series of Z-transitions (vertical sections (33)) to promote mixing. As described above in reference to FIG. 1(b), optical sensors that monitor the fluidic channels on the fluidic network are used both for metering and mixing operations. The lysis buffer includes glutathione isothiocyanate (5 M), NaCl (300 mM), Tris-HCl, pH 7.4 (60 mM), 1% Triton X-100, and optionally an antifoaming reagent. In a preferred embodiment, the mixing chamber includes a dried pill of antifoam reagent prior to fluid addition to the chamber. The chaotropic salt glutathione isothiocyanate lyses gram negative and, to a lesser degree, gram positive bacteria that can be present in the sample, and it also denatures proteins in the sample, including nucleases.

Once the sample is lysed, it is re-directed to the primary flow path and moved to the purification zone of the cartridge. The purification zone includes a waste chamber (29), one or more purification reagent chambers (26), and an integrated purification membrane (not shown). In a preferred embodiment, the purification zone comprises, from a proximal to a distal end, a purification multi-conduit fluidic junction including (a) a first purification reagent chamber conduit connecting the primary flow path and the purification reagent chamber; and (b) a second purification reagent chamber conduit connecting the purification reagent chamber and a purification reagent chamber air vent port; (ii) an integrated purification membrane positioned in the primary flow path of the purification zone; and (iii) a waste multi-conduit fluidic junction including (a) a first waste chamber conduit connecting the primary flow path and the waste chamber; and (b) a second waste chamber conduit connecting the waste chamber and a waste chamber air vent port. In a particularly preferred embodiment, the purification zone further comprises a pre-heating region (not shown) preceding the integrated purification membrane and configured to heat the elution buffer to maximize recovery of nucleic acids from the membrane. Preferably, the pre-heating region is in communication with one or more heating elements (or blocks) in the accompanying cartridge reader to heat the fluid within the pre-heating region to between 60 to 80° C., more preferably between about 65 to 75° C., and most preferably about 70° C.

As described above, the purification membrane, e.g., a glass fiber membrane, can be positioned on a support frit within the primary flow path and the membrane can be compressed prior to cartridge assembly. The geometry of the primary flow path in the purification zone is preferably configured to provide uniform fluid flow across the diameter of the membrane. In a preferred embodiment, the primary flow path in the purification zone is configured to provide a fluid flow path with a high aspect ratio to ensure a uniform flow with a relatively low retention volume. This facilitates the efficient capture of nucleic acids on the membrane. In a preferred embodiment, the glass membrane is cut and assembled in situ in a single step of the manufacturing process of the cartridge. As shown in FIGS. 3(c-d), the resulting design is composed of top (34) and base (35) plastic carriers with the glass membrane material (36) sandwiched in between. The knife edge (37) on the top carrier cuts through the membrane material and then it is welded to the bottom carrier with the application of ultrasonic energy. Panel (c) shows the configuration of the filter after ultrasonic welding. The knife edge (37) melts during ultrasonic welding and forms the weld bead. The thickness of the filter, the depth of the recess in the top carrier, and the depth of the weld determine the amount of filter compression. This approach minimizes handling of the membrane material and it facilitates reproducible pre-compression of the membrane.

Figure 3E:
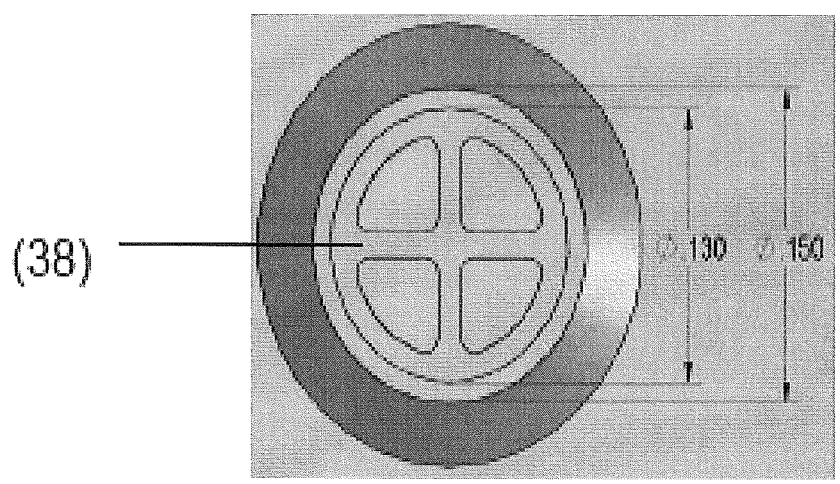
FIG. 3(e) shows one example of an aperture pattern for the top and base carriers for the membrane material. The pattern shown has an exposed membrane surface area of approximately 47%.
Figure 3H:
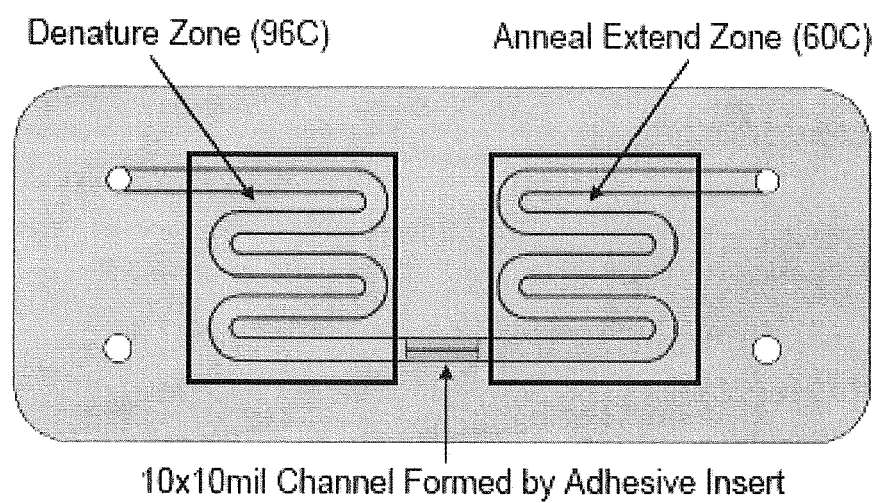
FIG. 3(h) shows the restriction zone in the flow path positioned between the denature zone and the anneal/extend zone (the first and second reaction temperature controlled zones). This feature causes an increase in the driving pressure as liquid traverses it. The pressure signal can therefore be used to determine the location of the front and back of a liquid slug and for closed-loop fluidic control.

The aperture design on the base plastic carrier supporting the membrane material can be optimized to increase the exposed surface area of the membrane material. A non-limiting example of an aperture design for the base plastic carrier is depicted in FIG. 3(e). This design features a support pattern (38) which is cross-shaped in the non-limiting embodiment shown in FIG. 3(e). The design shown optimizes the exposed membrane surface area, thereby significantly reducing the pressure drop that occurs as fluid is passed through the membrane. Additional parameters can be adjusted to maximize nucleic acid recovery while maintaining a reasonable pressure drop across the filter, e.g., less than about 15 psi and preferably less than about 10 psi regardless of the fluid matrix. Such additional parameters include but are not limited to weld depth, membrane diameter and pre-compression, and lysis buffer formulation. It is preferable to minimize the extraction volume in the purification zone to facilitate rapid thermocycling and to provide a compact cartridge design. In one embodiment, the retention volume of the membrane less than 10 uL, preferably less than 5 uL, and most preferably less than 2 uL. A volume of lysis buffer is added to the membrane and the eluate is collected in the waste chamber. The membrane is washed by a wash cycle which includes the addition of wash buffers, preferably including ethanol (most preferably 70% ethanol/water), to the membrane to remove contaminants, elution buffer is added (preferably 10 mM Tris 1.0 mM, pH 7.5, including 1 mM EDTA), and the purified sample is directed along the primary flow path to the PCR reaction zone.

In a preferred embodiment, the reaction zone is substantially adhesive free and/or free of seams in order to reduce bubble formation. Reagents required for the conduct of a reaction in the reaction zone can be stored in one or more reagent chambers within the cartridge and/or as dried pills stored in the primary flow path and/or in one or more reconstitution chambers fluidically connected to the primary flow path in the reaction zone. Lyophilized pills containing the appropriate reagents can be stored in the reconstitution chambers and in one embodiment, each chamber is includes a reagent used in a specific step of the procedure carried out in the PCR reaction zone. In one specific example, the pill is retained through the use of a chamber with an oblong or tri-lobed wall design, shown in FIGS. 3*f* and 3*g*, respectively.

In a specific embodiment, the cartridge includes a plurality of reconstitution chambers: (a) the first chamber houses the pill containing the reagents for reverse transcription including the first strand primers, Superscript-3 (reverse transcriptase), dNTP's, and other reagents necessary for cDNA formation; (b) the next chamber houses the pill containing reagents for PCR amplification, including dNTP's, primers, and Taq polymerase; (c) a third chamber can include additional primers, if a specific application requires a nested PCR amplification protocol; (d) a fourth chamber houses lyophilized EDTA and salts to inhibit Taq polymerase and to increase the ionic strength of the fluid sample, preparing it for the final denature step after PCR amplification is complete; and (e) a fifth reconstitution chamber holds the pill that contains the detection probes which is reconstituted after the sample is denatured, just before presentation to the capture array. The reagents in the first chamber are reconstituted and added to the primary flow path with the purified sample, where fluid is directed to the reaction zone to enable cDNA synthesis. In a preferred embodiment, the reaction zone is maintained at about 47° C. during cDNA synthesis. The reagents in the second chamber are then reconstituted and added to the fluid in the primary flow path. An important step in genomic amplification is the initial denature during which the long pieces of duplex DNA are melted apart, exposing the primer binding sequences and allowing the primers to bind before elongation by Taq polymerase. In a preferred embodiment, double stranded genomic DNA is denatured for about 90 seconds before cycling. Upon completion of this step the liquid sample containing the single stranded genomic material is moved from the first reaction temperature controlled zone (maintained at approximately 96° C.) to the second reaction temperature control zone (maintained at approximately 60° C.), where primers bind and are extended through the actions of Taq polymerase. The cartridge shuttles fluid between these two reaction temperature zones of the PCR reaction zone and this process is repeated up to about 45 times resulting in the generation of detectable PCR amplicons. Optionally, additional primers are reconstituted in the third chamber and combined with the fluid in the primary flow path, which is then cycled through the first and second reaction temperature controlled zones once more for amplification of nested sequences. The contents of the fourth chamber are reconstituted and directed to the primary flow path for the final denature step. Preferably, the final denature step is conduct at about 94° C.

In a preferred embodiment, the flow path between the first and second reaction temperature controlled zones comprises a restriction zone that enables the use of a pressure sensor to determine the location of the liquid between each reaction temperature controlled zone. When liquid traverses the restriction zone the driving pressure increases, indicating the position of the liquid in the flow path and allowing for closed loop control. The restriction zone is depicted in FIG. 3(*h*). In a preferred embodiment, the length of the restriction zone is between about 0.1-1.0 inches and more preferably about 0.375 inches, and the cross-sectional width and height are between 5 mils and 40 mils, and more preferably about 10 mils (1 mil=0.001 inches). Accordingly, the invention includes a method comprising: i) incubating a fluid slug in the first temperature controlled zone, ii) using pressure or vacuum to move the fluid slug through the restriction zone to the second reaction zone, iii) monitoring the applied pressure to determine when the fluid slug has fully passed through the reaction zone and iv) releasing the applied pressure or vacuum to stop fluid movement and to incubate the fluid slug in the second temperature controlled zone. The invention also includes the analogous method for moving the fluid slug from the second to the first temperature controlled zone as well as a method for cycling the fluid slug between temperatures by repeatedly moving the slug between the temperature zones.

The primary flow path leads from the reaction zone outlet to the detection zone. The detection zone is intersected by a detection reagent multi-conduit junction connecting (i) the primary flow path and one or more detection reagent chambers; and (ii) one or more detection reagent chambers and one or more detection reagent air vent ports. The detection zone is adapted to carry out a physical measurement on the PCR amplicons produced in the PCR reaction zone. Detection probes are reconstituted and directed to the primary flow path, where the probes are mixed with the PCR amplicons formed in the reaction zone. In a particularly preferred embodiment, the detection zone is configured to detect PCR amplicons using the nucleic acid detection assay depicted in FIG. 4. Briefly, oligonucleotide probes (41) composed of unique target-specific capture sequences are immobilized on separate electrodes (42) in the detection zone. These capture oligonucleotides are thiolated on the 5' end (43) and are covalently coupled to bovine serum albumin (BSA) (44) through sulfoSMCC linker chemistry, and the BSA is adsorbed onto the carbon-based electrode. Detection probes (45) are composed of unique oligonucleotide sequences containing a 3' biotin residue. These probes are coupled to an ECL-labeled streptavidin (46) at a 1:1 ratio. Both the capture and detection probes are unique sequences that are internal to the primer binding sites (47) used for PCR. This approach can be used to minimize possible competitive binding events that can occur in the presence of free PCR primers. The detection probes and amplicons are incubated in the detection zone, detection buffer is added, the detection zone is optionally washed, and electrode induced luminescence is detected.

The detection zone can be configured to conduct an assay in either a one- or two-step format. In a one-step format, the capture surface is exposed to a solution containing both analyte and detection probe in a single volume and incubated for a specified time before analysis. A two-step assay separates the analyte and detection probe: analyte solution is first incubated with the capture surface, followed by addition of detection probes and a second incubation. A wash step can be incorporated between the two steps to remove any unbound analyte before the addition of detection probes. In a preferred embodiment, a one-step assay format is employed in the detection zone.

Preferably, the electrodes in the assay cartridge are patterned in a two dimensional array along the fluid path. The array and/or fluid path are preferably in a linear arrangement, although other shapes (e.g., arcs, curves, zig-zags, etc. can also be used). In a preferred embodiment, the primary flow path in the detection zone is configured to maintain uniform flow through-out the detection zone and the flow path comprises a square or U-shaped arrangement. Most preferably, the length of the flow path along the direction of flow is greater than the width perpendicular to the direction of flow, the active area of the electrode takes up a significant portion of the width of the flow path (preferably greater than 60%, more preferably greater than 80%), and/or the height of the flow path above the electrodes is small compared to the width of the flow path. In an especially preferred embodiment, the electrodes are imaged using a CCD camera, electrochemiluminescence is triggered simultaneously across the entire electrode surface in the detection zone, and the camera images the entire electrode to detect emitted electrochemiluminescence.

As illustrated in FIG. 1(c) of copending U.S. Ser. No. 10,744,726, filed Dec. 23, 2003 and the accompanying text, an electrode array (preferably comprised of carbon ink) is applied to the substrate layer to form the electrode, electrical lead, and electrical contact portions. A dielectric layer is preferably applied over the electrode layer to define assay domains and impedance sensors. Alternatively, electrical contact can be printed on the opposing side of the substrate and connected to the electrodes or electrical leads via conductive through-holes through the substrate.

Co-pending U.S. patent application Ser. No. 10/185,274, filed Jun. 28, 2002, 10/744,726, filed Dec. 23, 2003, and Ser. No. 12/959,952, filed Dec. 3, 2010, hereby incorporated by reference, provide a number of examples of electrode and dielectric materials, electrode patterns and patterning techniques and immobilization techniques that are adapted for use in electrode-induced luminescence assays and suitable for use with the assay cartridges of the invention. Electrodes in the present invention are preferably comprised of a conductive material. The electrode can comprise a metal such as gold, silver, platinum, nickel, steel, iridium, copper, aluminum, a conductive alloy, or the like. They can also comprise oxide coated metals (e.g. aluminum oxide coated aluminum). Electrodes can comprise non-metallic conductors such as conductive forms of molecular carbon. Electrodes can also be comprised of semiconducting materials (e.g. silicon, germanium) or semi-conducting films such as indium tin oxide (ITO), antimony tin oxide (ATO) and the like. Electrodes can also be comprised of mixtures of materials containing conductive composites, inks, pastes, polymer blends, metal/non-metal composites and the like. Such mixtures can include conductive or semi-conductive materials mixed with non-conductive materials. Preferably, electrode materials are substantially free of silicone-based materials.

Electrodes (in particular working electrodes) used in assay cartridges of the invention are advantageously able to induce luminescence from luminescent species. Preferable materials for working electrodes are materials able to induce electrochemiluminescence from ruthenium-tris-bipyridine in the presence of tertiary alkyl amines (such as tripropylamine). Examples of such preferred materials include platinum, gold, ITO, carbon, carbon-polymer composites, and conductive polymers.

Preferably, electrodes are comprised of carbon-based materials such as carbon, carbon black, graphitic carbon, carbon nanotubes, carbon fibrils, graphite, carbon fibers and mixtures thereof. Advantageously, they are comprised of conductive carbon-polymer composites, conductive particles dispersed in a matrix (e.g. carbon inks, carbon pastes, metal inks), and/or conductive polymers. One preferred embodiment of the invention is an assay cartridge, preferably an assay cartridge, having electrodes (e.g., working and/or counter electrodes) that comprise carbon, preferably carbon layers, more preferably screen-printed layers of carbon inks. Some useful carbon inks include materials produced by Acheson Colloids Co. (e.g., Acheson 440B, 423ss, PF407A, PF407C, PM-003A, 30D071, 435A, Electrodag® 505SS, and Aquadag™), E. I. Du Pont de Nemours and Co. (e.g., Dupont® 7105, 7101, 7102, 7103, 7144, 7082, 7861D, E100735 62B and CB050), Advanced Conductive Materials (e.g., PTF 20), Gwen Electronics Materials (e.g., C2000802D2) and Conductive Compounds Inc (e.g., C-100), and Ercon Inc. (e.g., G-451, G-449 and 150401).

Electrodes can be formed into patterns by a molding process (i.e., during fabrication of the electrodes), by patterned deposition, by patterned printing, by selective etching, through a cutting process such as die cutting or laser drilling, and/or by techniques known in the art of electronics microfabrication. Electrodes can be self-supporting or can be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support, or substrate, can be rigid or flexible, flat or deformed, transparent, translucent, opaque or reflective. Preferably, the support comprises a flat sheet of plastic such as acetate or polystyrene. Electrode materials can be applied to a support by a variety of coating and deposition processes known in the art such as painting, spray-coating, screen-printing, ink-jet printing, laser printing, spin-coating, evaporative coating, chemical vapor deposition, etc. Supported electrodes can be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Electrodes can be supported by another conducting material. In some applications, screen printed carbon ink electrodes are printed over a conducting metal ink (e.g., silver ink) layer so as to improve the conductivity of the electrodes. Preferably, in assay cartridges, a miniaturized design allows the use of electrodes having short printed electrode leads (preferably less than 1.5 cm, more preferably less than 1.0 cm) that are relatively similar in length. By keeping the leads short, it is possible to use screen printed carbon electrodes without an underlying conductive metal layer such as a silver layer.

According to one preferred embodiment of the invention, the electrode surface (preferably a working electrode surface of an assay cartridge or assay plate) is bounded by a dielectric surface, the dielectric surface being raised or lowered (preferably raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary).

Preferably, the first electrode surface has an advancing contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary can be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface. In an especially preferred embodiment of the invention, the dielectric boundary is formed by printing a patterned dielectric ink on and/or around the electrode, the pattern designed so as to expose one or more assay domains on the electrode.

Electrodes can be modified by chemical or mechanical treatment to improve the immobilization of reagents. The surface can be treated to introduce functional groups for immobilization of reagents or to enhance its adsorptive properties. Surface treatment can also be used to influence properties of the electrode surface, e.g., the spreading of water on the surface or the kinetics of electrochemical processes at the surface of the electrode. Techniques that can be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes can be particularly beneficial by increasing the roughness and therefore the surface area of the electrodes. In the case of composite electrodes having conductive particles or fibers (e.g., carbon particles or fibrils) in a polymeric matrix or binder, selective etching of the polymer can be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment can change, for example, the physical properties, chemical composition, or surface-chemical properties of the electrode. These changes can, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas can also be used to introduce carboxylic acids or other oxidized carbon functionality into carbon or organic materials (these can be activated, e.g., as active esters or acyl chlorides) so as to allow for the coupling of reagents. Similarly, ammonia-containing plasmas can be used to introduce amino groups for use in coupling to assay reagents.

Treatment of electrode surfaces can be advantageous so as to improve or facilitate immobilization, change the wetting properties of the electrode, increase surface area, increase the binding capacity for the immobilization of reagents (e.g., lipid, protein or lipid/protein layers) or the binding of analytes, and/or alter the kinetics of electrochemical reactions at the electrode. In some applications, however, it can be preferable to use untreated electrodes. For example, we have found that it is advantageous to etch carbon ink electrodes prior to immobilization when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays can also be carried out on unetched carbon ink electrodes despite the presence of polymeric binders in the ink. In fact, in some applications requiring high sensitivity or low non-specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100 are used to facilitate spreading of reagents (e.g., capture reagents) onto unetched screen-printed electrodes (i.e., so as to allow the immobilization of the reagents), the solutions containing the reagents are allowed to dry onto the electrode surface. It has been found that this drying step greatly improves the efficiency and reproducibility of the immobilization process.

Electrodes can be derivatized with chemical functional groups that can be used to attach other materials to them.

Materials can be attached covalently to these functional groups, or they can be adsorbed non-covalently to derivatized or underivatized electrodes. Electrodes can be prepared with chemical functional groups attached covalently to their surface. These chemical functional groups include but are not limited to COOH, OH, $NH_2$, activated carboxyls (e.g., N-hydroxy succinimide (NHS)-esters), poly-(ethylene glycols), thiols, alkyl ($(CH_2)_n$) groups, and/or combinations thereof). Certain chemical functional groups (e.g., COOH, OH, $NH_2$, SH, activated carboxyls) can be used to couple reagents to electrodes. For further reference to useful immobilization and bioconjugation techniques see G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that can be used for ECL can be attached to the electrode via NHS-ester groups.

It can be desirable to control the extent of non-specific binding of materials to electrodes. Simply by way of non-limiting examples, it can be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $Ru^{III}(bpy)_3$ derivatives), oxalates, trialkylamines, antigens, analytes, and/or combinations thereof). In another example, it can be desirable to enhance the binding of biomolecules.

One or more chemical moieties that reduce or prevent non-specific binding (also known as blocking groups) can be present in, on, or in proximity to an electrode. Such moieties, e.g., PEG moieties and/or charged residues (e.g., phosphates, ammonium ions), can be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic (e.g., F108), Tetronic, Tergitol, and Span).

Materials used in electrodes can be treated with surfactants to reduce non-specific binding. For example, electrodes can be treated with surfactants and/or detergents that are well known to one of ordinary skill in the art (for example, the Tween, Triton, Pluronics (e.g., F108), Span, and Brij series of detergents). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) can be used instead of and/or in conjunction with surfactants and/or detergents. Undesirable non-specific adsorption of certain entities such as those listed above can be blocked by competitive non-specific adsorption of a blocking agent, e.g., by a protein such as bovine serum albumin (BSA), casein or immunoglobulin G (IgG). One can adsorb or covalently attach an assay reagent on an electrode and subsequently treat the electrode with a blocking agent so as to block remaining unoccupied sites on the surface.

Electrodes used in the assay cartridges are, preferably, non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

Preferred assay cartridges can use dielectric inks, films or other electrically insulating materials (hereinafter referred to as dielectrics). Dielectrics in the present invention can be used to prevent electrical connectivity between electrodes, to define patterned regions, to adhere materials together (i.e., as adhesives), to support materials, to define assay domains, as masks, as indicia and/or to contain assay reagents and other fluids. Dielectrics are non-conducting and advantageously non-porous (i.e., do not permit transmission of materials) and resistant to dissolving or degrading in the presence of media encountered in an electrode induced luminescence measurement. The dielectrics in the present invention can be liquids, gels, solids or materials dispersed in a matrix. They can be deposited in uncured form and cured to become solid. They can be inks, solid films, tapes or sheets. Materials used for dielectrics include polymers, photoresists, plastics, adhesives, gels, glasses, non-conducting inks, non-conducting pastes, ceramics, papers, elastomers, silicones, thermoplastics. Preferably, dielectric materials of the invention are substantially free of silicones. Examples of non-conducting inks include UV curable dielectrics such as materials produced by Acheson Colloids Co. (e.g., Acheson 451SS, 452SS, PF-455, PD039A, PF-021, ML25251, ML25240, ML25265, and Electrodag® 38DJB16 clear), Nazdar® (e.g., Nazdar® GS2081 3400SPL) and E. I. du Pont de Nemours and Co. (e.g., Dupont: 5018, 3571, and 5017).

Dielectrics, in accordance with certain preferred embodiments, can be applied by a variety of means, for example, printing, spraying, laminating, or can be affixed with adhesives, glues, solvents or by use of mechanical fasteners. Patterns and/or holes in dielectric layers can be formed by molding processes (i.e., during fabrication of the layer), by selective etching and/or by a cutting process such as die cutting or laser drilling. Dielectrics can be deposited and/or etched in patterns through the use of established photolithographic techniques (e.g., techniques used in the semiconductor electronics industry) and/or by patterned deposition using an evaporative or CVD process (e.g., by deposition through a mask). In a preferred embodiment, a dielectric ink is deposited on a substrate by printing (e.g., ink jet printing, laser printing or, more preferably, screen printing) and, optionally, UV cured. Preferably, the screen printed dielectric is UV curable allowing for improved edge definition than solvent based dielectrics. In another preferred embodiment, a non-conducting polymeric film is affixed to a support using an adhesive.

When using a dielectric ink printed on, or adjacent to, an electrode to confine fluids to regions of the electrode surface, the dielectric film preferably has a thickness of 0.5-100 micrometers, or more preferably 2-30 micrometers, or most preferably 8-12 micrometers and also, preferably, has a sharply defined edge with steep walls.

The use of patterned electrodes in cartridges can impose certain unique design and/or performance constraints. In particular, the use of patterned electrode leads can lead to problems associated with voltage drops along the leads, especially in applications like electrochemiluminescence that often require relatively high currents. The problems are often greatest when using electrodes comprising thin layers of only moderately conductive materials such as carbon inks. The problem can be partially mitigated by use of multi-layer patterned electrodes (where the conductivity of an exposed moderately conductive material such as a carbon ink is increased by printing it over a more conductive material such as a silver ink) although this approach introduces additional manufacturing steps. Alternatively, the problem can be partially mitigated in systems having multiple assay electrodes by keeping the leads short (preferably, so that the resistance between the electrode and the electrical contact is less than 500 ohms, more preferably less than 300 ohms, most preferably less than 100 ohms) to minimize the voltage drop and by keeping the leads about the same length to make the voltage drop consistent from electrode to electrode.

In an assay cartridge comprising multiple working electrodes, the variability from electrode to electrode in the voltage drop across the electrode leads is preferably smaller than the potential applied during the course of an assay measurement so that this variability has minimal effect on the variability of the measurements. In especially preferred embodiments, the variability in voltage drop across the leads is less than 20% of the potential applied during the course of an assay measurement, more preferably less than 10% or most preferably less than 2%. Alternatively, the uniformity in leads can be described in terms of the variation in resistance across the leads which is preferably less than 50 ohms, more preferably less than 10 ohms, most preferably less than 1 ohm.

Where the arrangement of the electrodes and/or contacts makes it difficult to keep the leads a uniform length, the matching of lead resistances can be accomplished by geometrically matching the length-to-width ratio of each electrode lead (assuming consistent print thickness). This length-to-width ratio is referred to hereinafter as the "number of squares." Typically, for a preferred cartridge-based configuration using screen printed carbon inks, the electrode leads are on the order of 4 to 5 squares. Commercially available inks typically have ink resistances that are specified in resistance per square per thickness (e.g., ohms/square/mil) and can vary widely depending on the ink selected. In a particularly preferred embodiment, a carbon ink is used that possesses an ink resistance that measures approximately 15 ohms/square/mil. The total resistance measured from end-to-end across a lead for one preferred embodiment is typically on the order of 450 ohms for a configuration utilizing a 5 squares lead.

According to another aspect of the present invention, the electrode surfaces are coated with assay reagents such as BSA or other specific binding reagents by dispensing solutions comprising the reagents to one or more appropriate locations on the electrode array, i.e., the capture surfaces. Preferably, the assay reagents collect on the surface (e.g., via the formation of covalent bonds, non-specific adsorption or specific binding interactions) to form an immobilized layer on the electrode. In a preferred embodiment, accurate volume delivery to a specified location results in complete coverage of only the desired electrode surface and/or a desired portion thereof. Accurate volume delivery to a specified location can be readily accomplished with commercially available dispensing equipment; e.g., commercially available equipment from BioDot.

Attaining complete coverage of a pre-defined region on a surface (e.g., an assay electrode) via localized deposition of a liquid (e.g., an assay reagent or a liquid comprising an assay reagent) can be difficult to achieve if the advancing contact angle of the liquid on the surface is high, thereby inhibiting spreading of the liquid on the surface (as has been observed for surfactant-free aqueous solutions on untreated carbon ink electrodes). Spreading can be accelerated by chemically modifying the surface to make it more wettable or by adding surfactants to the liquid, however, in many circumstances it is undesirable to change the physical properties of the surface or liquid. Alternatively, we have found that excellent and well controlled spreading of liquids can be achieved on surfaces, such as carbon ink electrodes, having high contact angle hysteresis (i.e., large differences in the advancing and retreating contact angle of the liquid on the surface, preferably differences greater than 10 degrees, more preferably greater than 30 degrees, more preferably greater than 50 degrees, most preferably greater than 70 degrees) by using impact-driven fluid spreading. Such results can be achieved without surface modification or the use of surfactants. Fluid is deposited (preferably, using a fluid micro-dispenser such as a micro-pipette, micro-syringe, solenoid valve controlled micro-dispenser, piezo-driven dispenser, ink-jet printer, bubble jet printer, etc.) on the surface at high velocity (preferably greater than 200 cm/s, more preferably greater than 500 cm/s, most preferably greater than 800 cm/s) so as to drive spreading of the liquid over the surface, despite the high advancing contact angle, to a size dictated by the volume and velocity of the dispensed fluid. The low retreating contact angle prevents significant retraction of the fluid once it has spread. Using the impact-driven spreading technique, it is possible to coat, with a predetermined volume of liquid, regions of a surface that are considerably larger (preferably, by at least a factor of 1.2, more preferably by at least a factor of two, even more preferably by at least a factor of 5) than the steady state spreading area of the predetermined volume of liquid on the surface (i.e., the area over which a drop having that volume spreads when touched to the surface at a velocity approaching zero).

Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability). More preferably, the liquid has a higher receding contact angle on the surrounding region than on the pre-defined region (preferably, the difference is greater than 10 degree, more preferably greater than 30 degrees, most preferably greater than 50 degrees). Even more preferably, the surrounding region also exhibits a low contact angle hysteresis for the liquid (preferably, less than 20 degrees, most preferably, less than 10 degrees). By using a surrounding region having high receding contact angle and/or low hysteresis, the tolerance for imprecision in deposition velocity or spreading rate becomes much improved. In a preferred deposition method, a small volume of reagent is dispensed onto the pre-defined region with sufficient velocity to spread across the pre-defined region and slightly onto the surrounding region, the liquid then retracts off the surrounding region (due to its high receding contact angle) but does not retract smaller than the size of the pre-defined area (due to its low receding contact angle). In especially preferred embodiments of the invention the pre-defined area is an exposed area of an electrode (preferably, a carbon ink electrode) and the surrounding region is provided by a dielectric ink patterned on the electrode.

As described above, assay reagents such as nucleic acids, proteins, or other specific binding reagents can be patterned by depositing (e.g., via impact driven spreading) solutions comprising the reagents on pre-defined locations on a surface (e.g., an electrode surface, preferably a carbon ink electrode surface) and allowing the reagents to become immobilized on the surface (e.g., via covalent bonds, non-specific interactions and/or specific binding interactions). Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability) so as to form a fluid containment region.

In certain preferred embodiments, nucleic acids, proteins or other binding reagents (preferably proteinaceous binding reagents) are immobilized on carbon ink electrodes by non-specific adsorption. It may be advantageous to allow the assay reagent solution to dry on the electrode during the immobilization procedure. Preferably, the immobilization procedure further comprises blocking un-coated sites on the surface with a blocking agent such as a protein solution (e.g., solutions of BSA or casein), washing the surface with a wash solution (preferably a buffered solution comprising surfactants, blocking agents, and/or protein stabilizers such as sugars) and/or drying the surface.

In a preferred immobilization procedure of the invention, imprecision due to variations in the ability of different assay reagents to adsorb on a surface such as a carbon ink electrode are reduced by immobilizing via a specific binding interaction involving a first and second binding partner. Such an immobilization technique is less likely to be affected by small variations in the properties of the surface. By way of example, nucleic acids can be patterned by patterned deposition of nucleic acid solutions (the first binding partner) on a surface coated with a nucleic acid complement (the second binding partner). Alternatively, assay reagents labeled with the first binding partner (preferably, biotin) can be patterned by patterned deposition of the assay reagents on a surface coated with the second binding partner (preferably, anti-biotin, streptavidin, or, more preferably, avidin). Most preferably, the second binding partner is deposited in the same pattern as the assay reagents. By analogy, the method can be adapted to use any of a variety of known first binding partner—second binding partner pairs including, but not limited to, hapten-antibody, nucleic acid—complementary nucleic acid, receptor-ligand, metal-metal ligand, sugar-lectin, boronic acid—diol, etc.

The skilled practitioner will be able to readily select materials suitable for the fabrication of the cartridges of the invention. Suitable materials include glass, ceramics, metals and/or plastics such as acrylic polymers (such as Lucite), acetal resins (such as Delrin), polyvinylidene fluoride (PVDF), polyethylene terephthalate (PET), polytetrafluoroethylene (e.g., Teflon), polystyrene, polypropylene, ABS, PEEK and the like. Preferably, the materials are inert to any solutions/reagents that will contact them during use or storage of the cartridge. In certain preferred embodiments, at least some portion of the cartridge is fabricated from transparent and/or translucent materials such as glass or acrylic polymer to provide windows that allow optical interrogation of fluids or surfaces inside the cartridge, e.g., for analysis of compositions within detection chambers of the cartridge or for monitoring and controlling the movement of liquids through the fluidic networks defined within the cartridge.

Figure 5A:
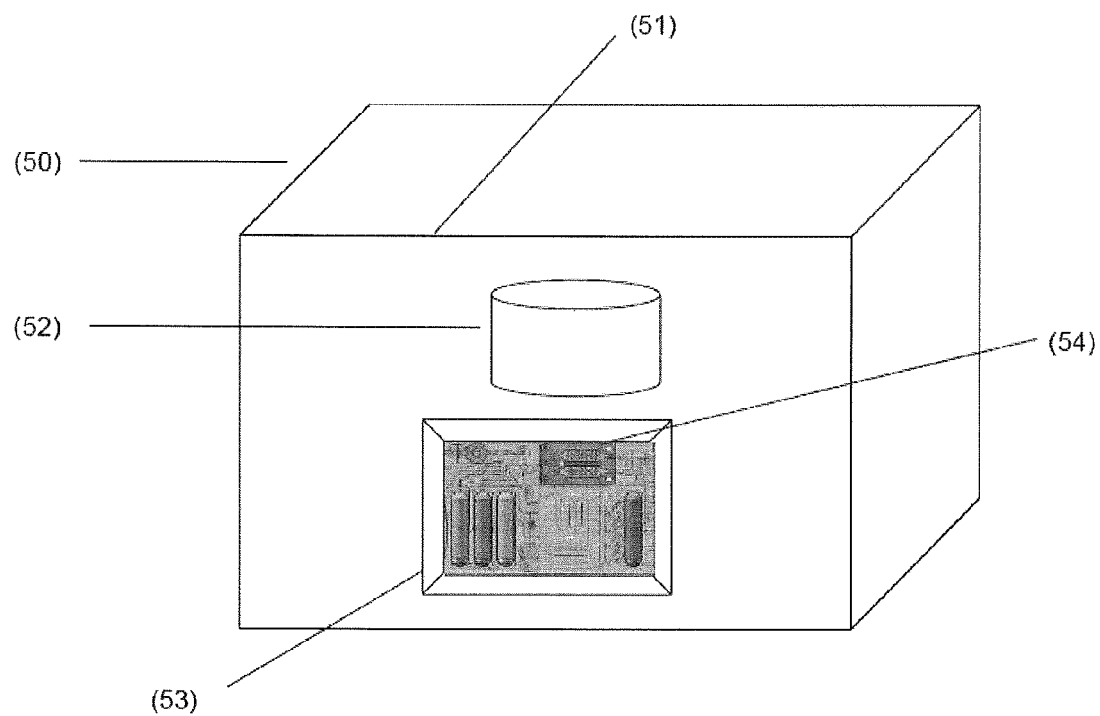
FIG. 5(a) is a simplified schematic of a reader configured to interface with a cartridge of the invention.

The assay cartridge is preferably adapted and configured to be selectively controlled via a reader instrument. In this regard, reference is made to FIGS. 1(a), 23, and 34, and the accompanying text of U.S. Ser. No. 10/744,726, filed Dec. 23, 2002, and FIGS. 42-46 and the accompanying text of U.S. Ser. No. 12/959,952, filed Dec. 3, 2010, the disclosures of which are incorporated herein by reference. FIG. 5(a) depicts a simplified schematic of the reader. The reader (50) preferably includes a housing (51), an optical detector (52), and the reader is adapted and configured to receive and position a cartridge (53) and/or the optical detector for processing of the cartridge. The reader also contains support subsystems that can include one or more of the following: sample acquisition/preprocessing/storage subsystem for sample handling; electrical subsystem for electrically contacting the cartridge's electrical contacts and supplying electrical energy to electrodes within the cartridge detection zone (54); and a control subsystem for controlling and coordinating operation of the system and subsystems and for acquiring, processing and storing the optical detection signal.

In a preferred embodiment of the invention, an assay cartridge has minimal or no active mechanical or electronic components. When carrying out an assay, such an assay cartridge can be introduced into a reader which provides these functions. For example, a reader can have electronic circuitry for applying electrical energy to the assay electrodes and for measuring the resulting potentials or currents at assay electrodes. The reader can have one or more light detectors for measuring luminescence generated at assay electrodes. Light detectors that can be used include, but are not limited to photomultiplier tubes, avalanche photodiodes, photodiodes, photodiode arrays, CCD chips, CMOS chips, film. The light detector can be comprised within an optical detection system that also comprise lenses, filters, shutters, apertures, fiber optics, light guides, etc. The reader can also have pumps, valves, heaters, sensors, etc. for providing fluids to the cartridge, verifying the presence of fluids and/or maintaining the fluids at an appropriate controlled temperature. The reader can be used to store and provide assay reagents, either onboard the reader itself or from separate assay reagent bottles or an assay reagent storage device. In a preferred embodiment, all assay reagents required for an analysis of a sample are stored within the assay cartridge. The reader can also have cartridge handling systems such as motion controllers for moving the cartridge in and out of the reader. The reader can have a microprocessor for controlling the mechanical and/or electronic subsystems, analyzing the acquired data and/or providing a graphical user interface (GUI). The reader can also comprise electrical, mechanical and/or optical connectors for connecting to the cartridge.

Figure 5B:
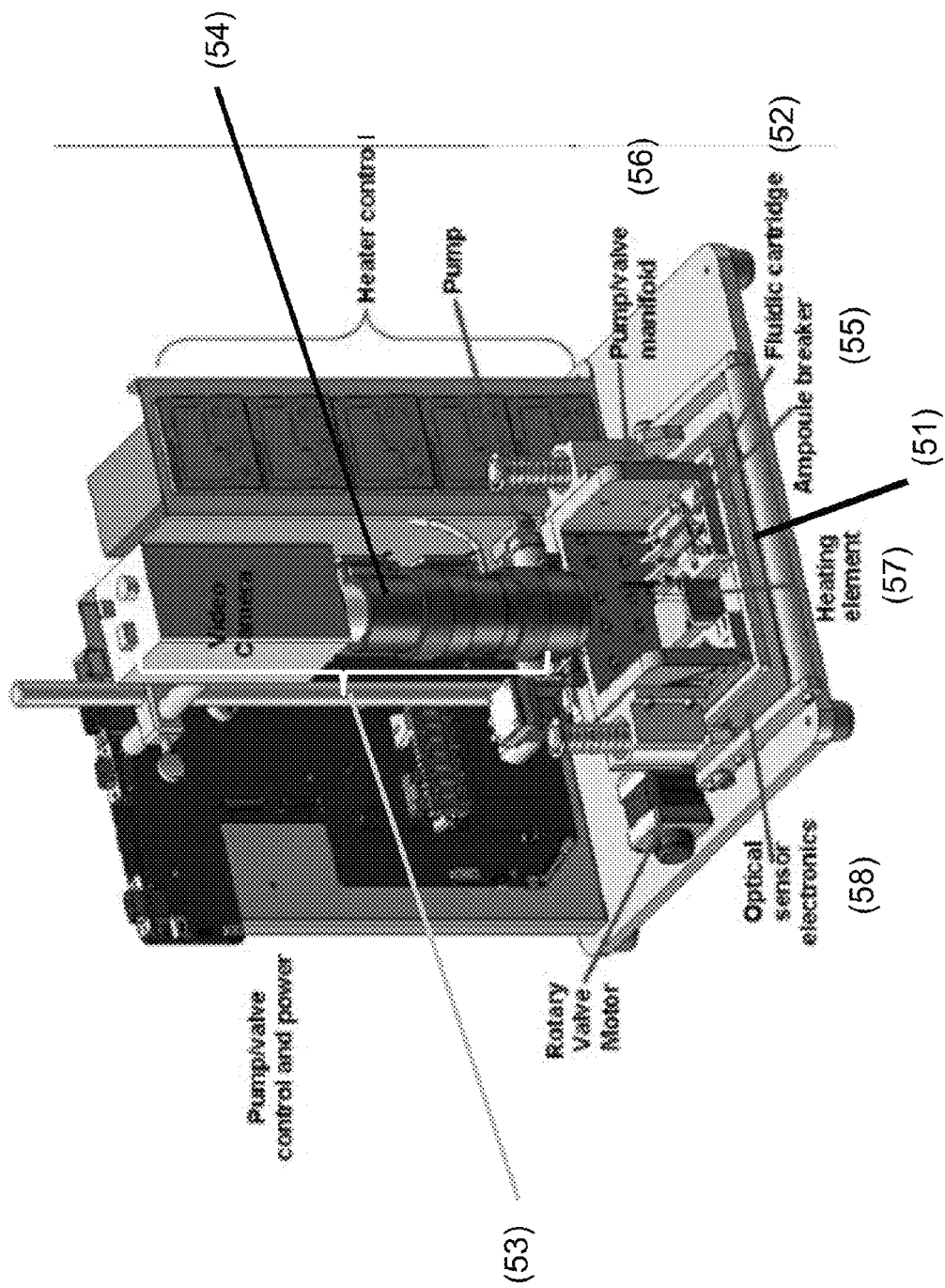
FIG. 5(b) shows one embodiment of a reader according to the present invention.

An exemplary reader is depicted in FIG. 5(b). The reader includes a housing and an enclosure positioned within the housing (not shown); a cartridge tray (51) for holding the assay cartridge (52) during analysis in the reader; and a mounting frame (not shown) in the enclosure configured to align the cartridge with one or more reader components including, but not limited to (i) an optical detection assembly (53) comprising at least one optical detector (54); (ii) an ampoule breaking mechanism (55); (iii) an electrode contact pin assembly positioned over the cartridge tray (not shown); (iv) a fluidic control manifold (56) configured to drive fluid motion within the fluidic network of the cartridge; (v) one or more heater assemblies (57); and (vi) one or more optical fluid sensors (58).

The ampoules in the cartridge can be broken serially (one at a time) or in parallel (simultaneously or substantially simultaneously). In a preferred embodiment, each ampoule in the cartridge is broken independently. A variety of different approaches are available for driving a hammer element to break an ampoule including but not limited to directly coupling the hammer to a motor, solenoid or other active drive element for striking the ampoule with the hammer or, alternatively, by releasing a hammer held under a spring force (in which case an active drive element can be used to load a spring). In a preferred embodiment, the cartridge reader comprises a solenoid driven mechanism configured to break each ampoule in the cartridge independently.

The ability to control the temperature of distinct regions of the cartridge with a high degree of precision is particularly preferred. As described above, an assay cartridge can include a plurality of distinct temperature controlled zones and the accompanying reader includes a cartridge tray with thermally isolated aluminum heating and/or cooling blocks, as appropriate, for each temperature controlled zone. As shown in FIG. 6(*a-b*), heating elements interface with the cartridge through a heater block positioned on the top side and two bottom heater plates. There are at least three distinct heating zones that are formed in the heating block shown in FIGS. 6(*a-b*). One heating zone (63) is configured to heat the purification zone. This purification heater block is configured to surround the purification zone, allowing for the maximum heat transfer during the drying and elution steps of the purification process. The other heating zones (61 and 62) are configured to heat the PCR reaction zone of the cartridge. These zones (61 and 62) maintain two different temperatures for denaturing cycles and anneal/extend cycles. The lower heaters are two flat heaters separated by an air gap that thermally insulates them from each other. In a preferred embodiment, the heating block is configured to heat the top and bottom surfaces of the cartridge and the primary flow path in the purification and detection zones is configured to maximize heat transfer for rapid thermal cycling. FIG. 6(*c*) shows another embodiment of the cartridge and the various temperature controlled zones within. The cartridge includes a purification zone (64) maintained at about 70° C., the PCR reaction zone including two temperature controlled regions, i.e., the denature region (65) maintained at about 96° C. and the anneal/extend region (66) maintained at about 60° C., and the detection zone (67) which is maintained about 20-40° C., preferably 20-35° C., and most preferably 25-35° C. In a preferred embodiment, the reader further comprises a heater/cooling device, e.g., a theromoelectric Peltier device, to interface with the detection zone that is capable of both heating and cooling.

In a preferred embodiment, the step of PCR amplification in the cartridge is allotted approximately 15 minutes or less of the total cartridge processing time. In order to accomplish between about 35-45 cycles of PCR, the time a fluid sample spends between the temperature set points for denaturing and annealing/extension in each cycle in the detection zone should be minimized. Two factors that can affect the total PCR time are (i) the time elapsed when moving from one temperature zone to another, and (ii) the time it takes for the fluid sample to reach the temperature set point, which is similar to the ramp rate in a conventional thermal cycler. The time it takes for fluid sample to transition from one temperature zone to another can be adjusted by adjusting the pump speed. In a preferred embodiment, the elapsed time between fluid transitions between the two reaction temperature controlled zones in the detection zone is less than 5 seconds, and preferably less than 1 second. In order to minimize the time for the fluid sample to reach the set point, the detection zone includes a serpentine shape, increasing the fluid surface area contacting the heating surfaces. The channels in the detection zone of the cartridge are 0.080"× 0.020". This aspect ratio, along with the temperature feedback of the heaters and controllers, allows for rapid temperature increases and decreases during thermal cycling. Total cycle times of about 20 seconds effectively generate PCR signal in as few as 35 cycles. The temperature of each of the temperature controlled zones is preferably controlled with resistive heating elements and a panel of Watlow heater controllers with thermocouple feedback control. Thermally conductive gasket material is preferably used to ensure that there is good thermal transfer between the heating blocks and the cartridge. With this thermal control configuration, the temperature within a temperature controlled zone of the cartridge can be maintained with an accuracy of ±0.5° C. In a preferred embodiment, each of the temperature controlled zones can be independently maintained at the appropriate temperature.

Figure 7:
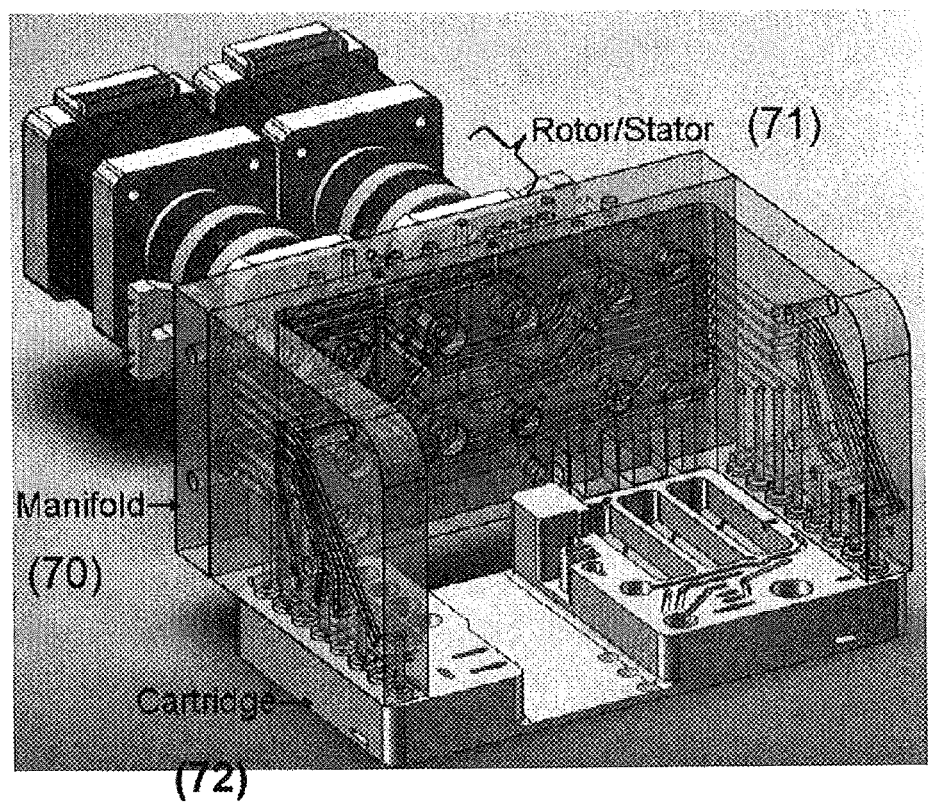
FIG. 7 shows a fluidic control manifold of the reader of the invention.

The movement of a liquid sample through all of the processing steps involved in the PCR cartridge is controlled by mating vent ports on the cartridge to a fluidic control manifold that seals against the cartridge. The fluidic control manifold includes valves that allow each vent port to be sealed, opened to ambient pressure or connected to a pressure/vacuum source. Accurate fluid movement through the cartridge using pressure is achieved through the use of optical sensors to provide closed loop control. The manifold shown in FIG. 7 is an acrylic piece made from multiple precision machined acrylic layers that are laminated together using a vapor bonding process. The channels of the manifold preferably have a large dimension to reduce resistance and allow a high volume of air to pass at a relatively low pressure. Preferably, the fluidic control manifold does not come into contact with fluid in the cartridge and is protected by aerosol filters in the cartridge vent ports, which reduces the risk of contamination and minimizes the need for cleaning.

In one embodiment, the fluidic control manifold (70) includes at least two types of valves. The first type is a rotary shear valve (71) composed of two discs with machined apertures/ports, a Teflon stator and a stainless steel rotor. A specific vent on the cartridge (72) is linked to the pump or to ambient pressure by aligning the corresponding ports on the stator and rotor, respectively. Tension between the stator and rotor can be adjusted to provide a air tight seal between the discs while also allowing for free rotation of the discs relative to each other. Accurate positioning of the rotor is enabled through the use of an optical encoder. The reader includes at least two rotary shear valves so that any two vent ports on the cartridge can be addressed at any one time, i.e., one port is connected to vacuum or pressure, the second is opened to ambient atmosphere and the remaining ports are left sealed. To stop fluid flow on a fast time scale, two fast-acting solenoid relief valves (not shown) are incorporated between the rotary shear valves and the cartridge that can quickly release the applied pressure with a response time of approximately 10 ms. To prevent overheating of the solenoids, electronic controls of the valves can be included if necessary so that they are only powered when needed.

There are at least two types of pumps used in the reader. To generate pressure for liquid movement, a linear actuator driving an air cylinder is used. All liquid movement in the fluidic network is driven from this high precision air cylinder. The other pump is a high volume and pressure diaphragm pump. This pump serves only one function during the cartridge processing and that is to dry the integrated purification membrane. Drying the extraction membrane serves to drive off any residual wash buffer and requires a large volume of air.

Closed-loop feedback control of fluid movement in the cartridge is achieved by monitoring fluid movement in the cartridge through the use of infra-red reflective optical sensors in the reader. These sensors are positioned beneath the cartridge as shown in FIG. 5(b). The optical sensors function to feed-back information to control the valves through closed-loop deterministic control using a high speed microprocessor. The data from the optical sensors is collected in a serial manner to eliminate potential cross-talk and potential false signals that can result in improper fluid addressing. The response time of the optical sensor feedback loop is approximately 30 ms, allowing all of the sensors to be cycled through to generate a complete picture of the location and behavior of the fluid sample.

The reader is preferably packaged as a single self-contained unit. In preferred embodiments employing luminescence based assays, a smaller light-tight region is incorporated within the overall reader housing. This allows the luminescence based assay to be performed within the light tight enclosure to ensure that the readings are not affected by ambient light. Preferably, electronic components and other heat-generating components are located outside of the light tight enclosure.

The cartridge handler subsystem preferably includes a motor to draw the cartridge into the cartridge housing and selectively position the cartridge within the reader; e.g., position the cartridge under a sensor/detector. In one preferred embodiment, retraction of the cartridge within the reader housing can be mechanically coupled to one or more mechanisms within the reader for synchronized/coordinated operation of the linked mechanisms. For example, the retraction of the cartridge can be mechanically coupled to: the mechanism for closing the door to the light tight enclosure after the cartridge has entered the chamber; the assay electronics subsystem (described in greater detail below) to allow the reader's electrical contacts to engage the cartridge's electrical contacts, i.e., be placed into electrical contact with the electrode array's electrode contacts; the fluidic handler subsystem's fluidic control manifold to engage the cartridge's fluid ports, i.e., be placed into fluidic communication with the cartridge's fluidic ports (e.g., establishing a pressure seal between the cartridge's fluidic ports and the fluid control manifold); and/or the fluid handler subsystem's reagent cartridge breaking mechanism to allow the reagent cartridges such as ampoule(s) to be broken during the cartridge retraction/positioning step.

In a preferred embodiment a barcode reader is incorporated on/within the reader to preferably automatically scan an identifying mark/label on the cartridge; e.g., as it is drawn into the reader. The label can contain encoded information relating to the specific assays that are to be performed, calibration parameters and/or any other information required to perform the assay.

The assay electronics subsystem preferably includes electrical contacts, sensors and electronic circuitry. The electrical contacts are preferably adapted and configured to be placed into electrical contact with the electrode array. In one preferred embodiment, the reader's electronic circuitry can include analog switching and trans-impedance amplification circuits to address a specific pair of electrodes (i.e., pair-wise firing, discussed in greater detail above) and apply a predefined voltage waveform to the circuit formed by that electrode pair. The actual output voltage and current can be optionally measured for diagnostic purposes. Preferably the electronic circuitry is also capable of applying an AC waveform (e.g., 500 Hz or less) for capacitive or conductive measurements (as discussed above).

In one particularly preferred embodiment of the reader configured to perform luminescence based assays, the reader can employ an optical detector, e.g., a photodiode (most preferably, a cooled photodiode), photomultiplier tube, CCD detector, CMOS detector or the like, to detect and/or measure light/luminescence emanating from the read chambers. If a cooled photodiode is employed, a thermo-electric cooler and temperature sensor can be integrated into the photodiode package itself providing for selective control by the electronic control system.

A computerized control system is preferably utilized to selectively control operation of the cartridge-based system. The computerized control system can be fully integrated within the reader, separated from the reader in an externally housed system and/or partially integrated within and partially separated from, the reader. For example, the reader can be configured with external communications ports (e.g., RS-232, parallel, USB, IEEE 1394, and the like) for connection to a general purpose computer system (not shown) that is preferably programmed to control the reader and/or its subsystems. In one preferred embodiment, a single embedded microprocessor can be used to control the electronics and to coordinate cartridge operations. Additionally, the microprocessor can also support an embedded operator interface, connectivity and data management operations. The embedded operator interface can preferably utilize an integrated display and/or integrated data entry device (e.g., keypad). The computerized control system can also preferably include non-volatile memory storage for storing cartridge results and instrument configuration parameters.

Preferably, the reader has a cartridge handling subsystem that mechanically engages the cartridges and moves/aligns it into position. Preferably, this process includes positioning the cartridge within a light-tight enclosure. The reader also makes the appropriate fluidic and/or electronic connections to the cartridge and, optionally, breaks or pierces any reagent chamber (e.g., reagent ampoules) present in cartridge reagent chambers. As discussed above, in one preferred embodiment, the cartridge handler's motion would be physically coupled to the fluidic and electronic handlers (and, optionally, the reagent cartridge release mechanism) such that upon positioning the cartridge within the light tight enclosure the electrical contacts and the fluidics manifold engage the cartridge at their respective engagement points (and, optionally, the reagent cartridge release mechanisms releases reagent from any reagent cartridges). Next, where required or preferred, the electronic control system begins operating one or more heating elements in order to bring a zone of the cartridge, i.e., the purification zone (the preheating region, the additional temperature controlled region in the purification zone, or both), the first and/or second reaction temperature controlled zones in the reaction zone, and the detection zone, to the appropriate predetermined temperature and maintain the cartridge at such target temperature.

The assay cartridges can be used for multiplexed detection of one or more biological agents in a sample, e.g., bacteria, viruses, biological toxins, and the like. A "biological agent" refers to any biological material that can be identified, e.g., cells, viruses, naturally occurring proteins, glycoproteins, complex and simple sugars, nucleic acids, lipids, and lipoproteins, as well as toxins, particularly nucleic acid and protein-based toxins, both natural and synthetic. A non-exemplary list of biological agents that can be detected using the cartridge and methods of the invention include pathogens associated with upper respiratory infection (e.g., influenza A, influenza B, Respiratory Syncytial Virus, Streptococci species), pathogens found in food and water (e.g., *salmonella, listeria, cryptosporidia, campylobacter, E. Coli* 0157, etc.), sexually transmitted diseases (e.g., HIV, syphilis, herpes, gonorrhea, HPV, etc.), and blood borne pathogens and potential bioterrorism agents (e.g., pathogens and toxins in the CDC lists of Select A, B and C agents such as *B. anthracis, Y. pestis*, small pox, *F. tularensis*, ricin, botulinum toxins, *staph* enterotoxins (including but not limited to methicillin-resistant *Staphylococcus aureus* (MRSA)), Vancomycin Resistant *Enterococcus* (VRE), *Clostridium difficile*, Enteroviral meningitis, etc.). Preferred panels also include nucleic acid arrays for measuring mRNA levels of mRNA coding for cytokines, growth factors, components of the apoptosis pathway, expression of the P450 enzymes, expression of tumor related genes, pathogens (e.g., the pathogens listed above), etc. Preferred panels also include nucleic acid arrays for genotyping individuals (e.g., SNP analysis), pathogens, tumor cells, etc.

In a particularly preferred embodiment, the cartridge includes at least a panel of the following eight agents, with two DNA or RNA sequences targeted per agent: *Bacillus anthracis* (BA), *Yersinia pestis* (YP), *Francisella tularensis* (FT), *Brucella* species, Variola virus (smallpox), Ebola virus, Marburg virus, and Venezuelan Equine Encephalitis (VEE).

The present invention also includes kits. The kits can include disassembled components necessary to make an assay cartridge of the invention. Alternatively, the kits can comprise, in one or more containers, an assay cartridge of the invention and at least one additional assay reagent necessary to carry out an assay. The one or more assay reagents can include, but are not limited to, binding reagents (preferably, labeled binding reagents, more preferably binding reagents labeled with electrochemiluminescent labels) specific for an analyte of interest, ECL coreactants, enzymes, enzyme substrates, extraction reagents, assay calibration standards or controls, wash solutions, diluents, buffers, labels (preferably, electrochemiluminescent labels), etc.

The invention includes assay cartridges (preferably assay cartridges) and readers (preferably readers) as described above. These can be supplied as separate components. The invention also includes assays systems that comprise an assay cartridge (preferably a cartridge) and a reader (preferably a reader).

EXAMPLES

Example 1. Nucleic Acid Extraction and Purification

Approach Used for Nucleic Acid Extraction and Purification.

Nucleic acids are extracted from a sample by lysis in a guanidine isothiocyanate (GuSNC) buffer. Purification of nucleic acid from potential interferents in clinical samples is achieved by binding nucleic acid to a silica matrix in the presence of GuSCN. To test this method, multiple types of purification matrices were tested in a prototype mini-column component to determine which would have the highest binding capacity and which could be readily incorporated into a small format suitable for the cartridge of the invention. Whatman glass fiber membranes (types GF/D and GF/F; available from Whatman Ltd.), 3M Empore membranes (available from 3M, St. Paul, Minn., and Sigma size-fractionated silica dioxide particles (available from Sigma-Aldrich Co., St. Louis, Mo.) were tested as possible candidates. Whatman G F/D, GF/F, and 3M Empore, were tested and compared for total nucleic acid binding capacity. Whatman G F/D was found to have the highest binding capacity compared to the other matrices (about 8.3 ug/mg). Most importantly, GF/D can readily be integrated into a fluid flow path of a cartridge and the total binding capacity of the membrane can be adjusted by simply adding additional layers of GF/D.

Figure 8:
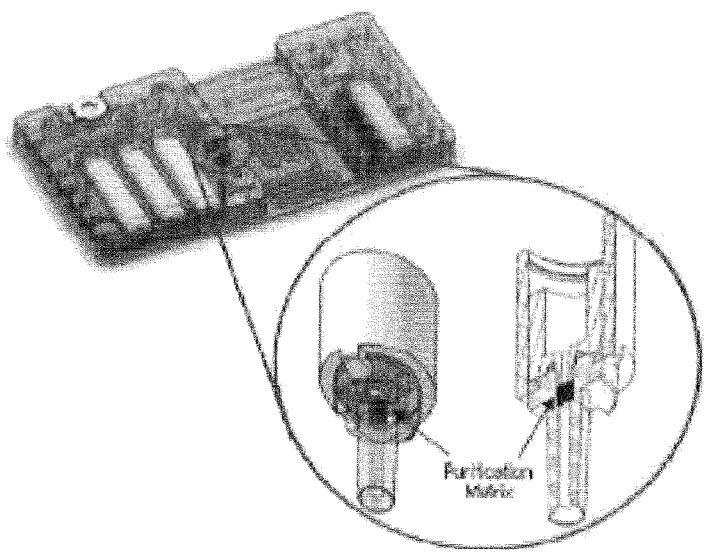
FIG. 8 shows a mini-column prototype.

Buffers for nucleic acid extraction and purification were initially formulated and optimized using spin column methods. Further characterization and optimization was then carried out using a mini-column prototype (FIG. 8) to facilitate incorporation of a membrane into a cartridge and to examine fluid flow through the membrane under conditions that mimic those expected in a cartridge. The interior of the prototype included a similar geometry to what would be used in a cartridge, including a support frit, a pre-compression mechanism, and features designed to minimize unwanted fluid retention. Using this prototype, the thickness and aspect ratio of the membrane was optimized to minimize the retention of fluid. It was found that using two layers of GF/D membrane discs, each with a diameter of 0.81" was preferable. Design approaches were also developed to securely hold the membrane in place and to provide pre-compression of the membrane to reduce fluctuations in the volume of the membrane as it is wet with different solvents.

The extraction prototype system consisted of a small column and a pump to pull air/buffer through the column, along with a pressure sensor and associated fluidic lines. Pressure, pump speed, and flow volume through the purification column were controlled. Using this prototype, a liquid sample, mixed with GuSCN lysis buffer, was passed through the purification column to bind nucleic acids. Wash buffers (lysis buffer and ethanol) were sequentially passed through the column to remove contaminants. Finally, the purification matrix was dried by air flow and heated before introduction of elution buffer (a low ionic strength aqueous buffer) to release the bound nucleic acid.

Practical Considerations Relating to Flow of Samples and Buffers Through Glass Fiber Membranes.

An important factor considered during purification matrix optimization was ensuring that the column geometry facilitated homogeneous flow across the diameter of the column when driving fluids with air pressure. Testing of designs with different aspect ratios (thickness/diameter) revealed that higher aspect ratio columns had more homogeneous flow and had lower retention of fluid. When drying a low aspect ratio column by passing air through the column, drying of a small region of the membrane surface provided a low resistance pathway that essentially prevented complete drying across the diameter of the membrane. High aspect ratio columns provided more efficient capture of nucleic acids, probably because the entire volume of the column was more evenly interrogated. The goal in the extraction and elution steps was to recover the DNA/RNA in the smallest possible volume, which could be used as the starting material in the amplification process. A small extraction volume will facilitate rapid thermocycling and will allow for a compact cartridge design. The retention volume of the prototype purification chamber geometry and aspect ratio was about 4 uL.

Figure 9:
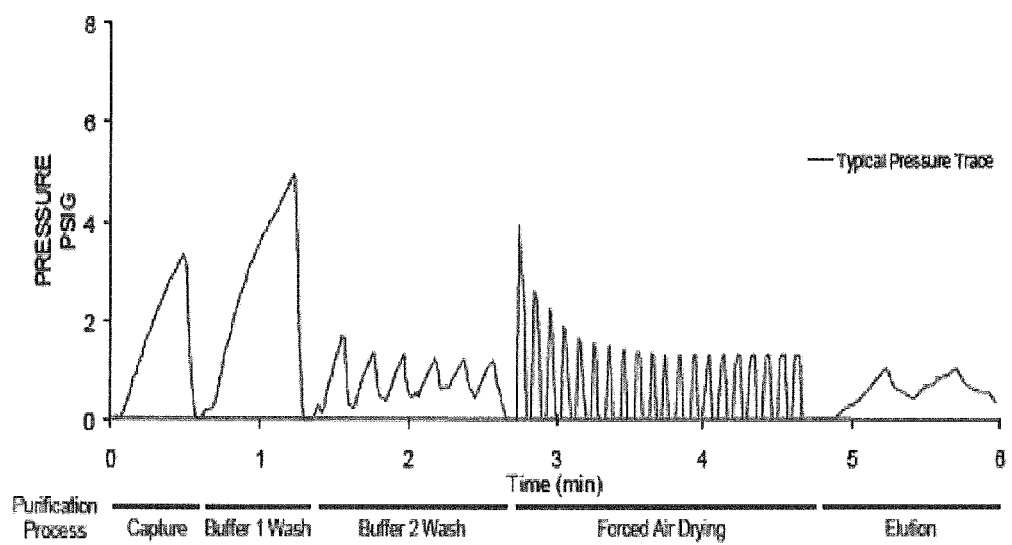
FIG. 9 shows pressure traces for a typical purification of DNA from a model organisms using the mini-column prototype and shows the pressures created during i) loading of samples in GuSCN lysis buffer; ii) washing of the column with clean GuSCN lysis buffer (buffer 1) and ethanol (buffer 2); iii) drying of the column with air flow; and iv) elution of nucleic acid with low ionic strength elution buffer.

In the cartridge design, fluid movement is driven by application of air pressure or vacuum. Another consideration in the design of the purification component is ensuring that samples and purification reagents can be driven through the GF/D membrane at reasonable flow rates (compatible with the 15 minutes allocated for sample lysis and purification in the assay cartridge) using reasonable pressures (i.e., less than about 0.5 atm or about 7 psi) that will not compromise seals within the cartridge. FIG. 9 presents pressure traces for a typical purification of DNA from a model organisms using the mini-column prototype and shows the pressures created during i) loading of samples in GuSCN lysis buffer; ii) washing of the column with clean GuSCN lysis buffer (buffer 1) and ethanol (buffer 2); iii) drying of the column with air flow; and iv) elution of nucleic acid with low ionic strength elution buffer. Briefly, 100 uL of an overnight *E. coli* culture was lysed in GuSCN and purified on a GF/D membrane in a mini-column fixture. Fluid movement was driven by vacuum created by an air cylinder (syringe) run at a speed of 1 to 2 mL per minute for fluid movement steps or 273 mL/min for air drying.

Figure 10:
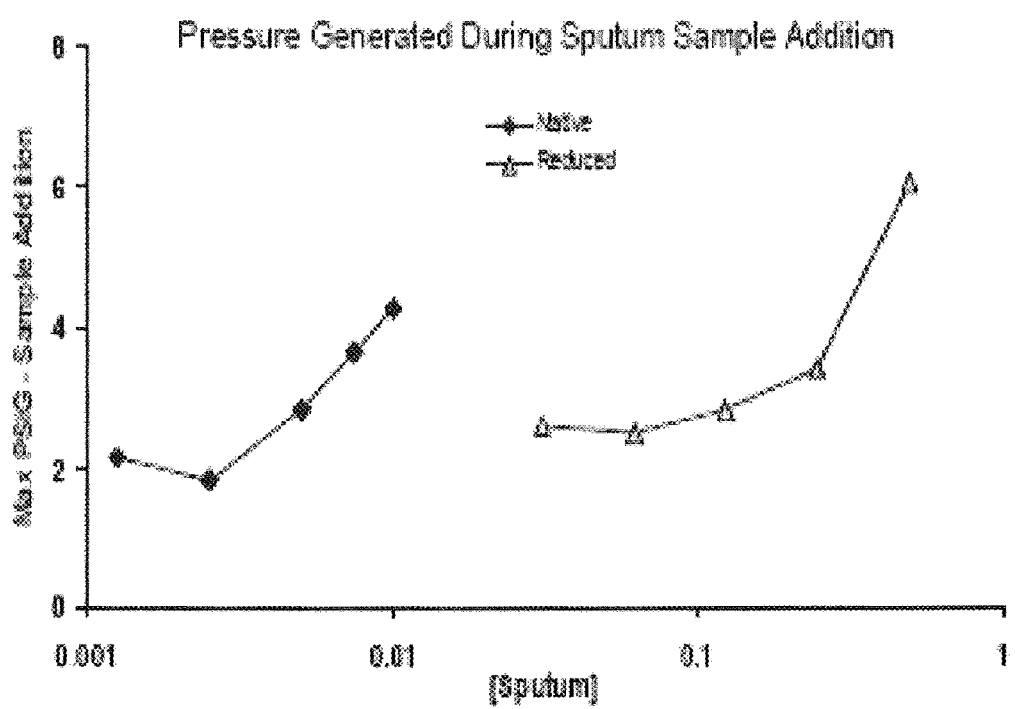
FIG. 10 is a graph demonstrating that, relative to untreated sputum, up to 50 times more DTT-treated sputum could be loaded on the mini-column prototype while maintaining acceptable pressures.

A number of different clinical matrices of different viscosity were tested with the mini-column prototype. Whole blood samples (viscosity of about 4 cps) were readily processed and produced pressure profiles similar to that presented in FIG. 9, although with a slightly higher pressure during sample loading (about 5 psi). Sputum yielded significant elevation of pressure during sample loading (the viscosity of sputum can be in the hundreds of cps). This effect could be markedly reduced by treating sputum samples with a reducing agent dithiothreitol (DTT) to decrease viscosity prior to loading. FIG. 10 demonstrates that, relative to untreated sputum, up to 50 times more DTT-treated sputum could be loaded while maintaining acceptable pressures. Briefly, test samples were homogenized by the addition of an equal volume of phosphate buffered saline and vortexed with 2 mm glass beads to make 1× stock. Serial dilutions were then made and either treated with 0.1% DTT at room temperature for 1 hour (triangles) or untreated (diamonds). Replicates were then purified in the mini-column prototype while monitoring column pressure. The data shows the highest observed pressure as a function of the sputum dilution (1=undiluted). The highest concentration point for each sample type is the highest concentration that could be run without exceeding the pressure specification.

Efficiency of Nucleic Acid Purification.

Figure 11:
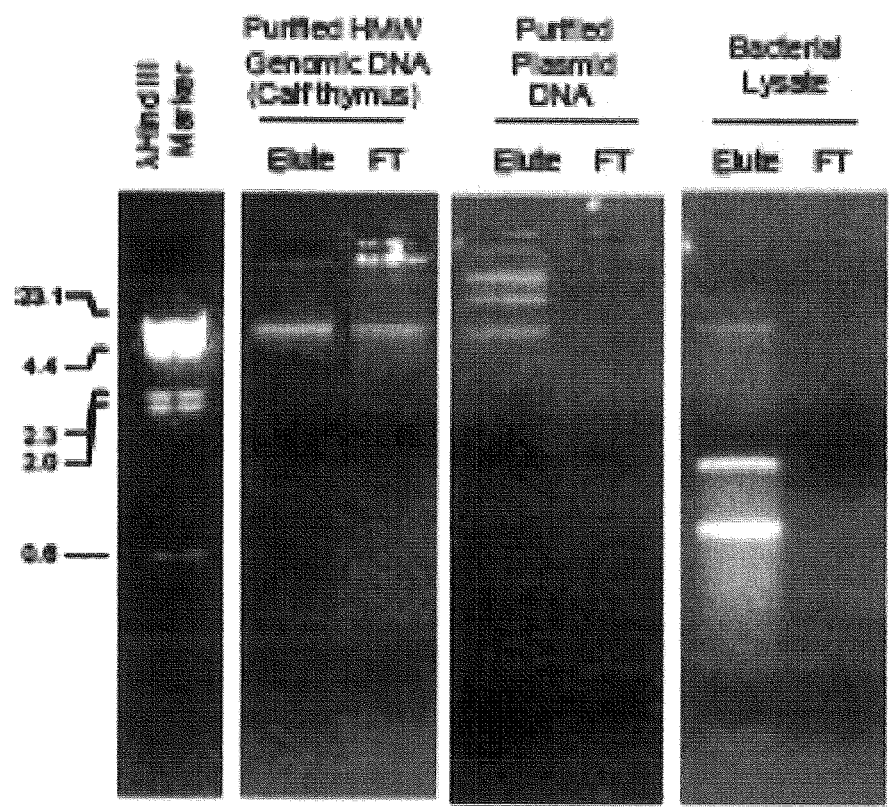
FIG. 11 demonstrates that multiple types of nucleic acid, including genomic DNA, plasmid DNA, and total bacterial lysate (containing both genomic DNA and RNA) could be captured and eluted from the purification membrane.

Using the prototype mini-column, the effect of temperature on nucleic acid elution efficiency was also investigated. Optimal elution of nucleic acid from the purification matrix was done by increasing the temperature of the elution buffer and GF/D matrix to 70° C. This information aided in the design of the final cartridge and reader as it led to the incorporation of heating elements to allow the purification matrix to achieve the optimal temperature for nucleic acid elution. FIG. 11 shows that multiple types of nucleic acid, including genomic DNA, plasmid DNA, and total bacterial lysate (containing both genomic DNA and RNA) could be captured and eluted from the purification membrane. Briefly, purified high molecular weight genomic DNA from calf thymus, purified plasmid DNA, or a bacterial lysate containing a mixture of high molecular weight genomic DNA and RNA of various sizes were all subjected to purification using the nucleic acid extraction and purification prototype.

For each sample type the flow-through (FT) material and the eluted material were retained for comparison. After purification, the eluate and the pooled (low-through fractions were resolved on a 1% agarose gel and visualized with ethidium bromide staining. The absence of bands in the lanes for flow-through material (nucleic acid that was not captured during sample loading) shows that capture of nucleic acid was very efficient. The one exception was high molecular weight calf thymus genomic DNA; some DNA was observed in the flow-through, although greater than 50% of the DNA was captured on the membrane. High levels of purity could be achieved using the prototype. The column washing protocols routinely achieved wash qualities of 1 to 10 parts per 100,000, a level that was found to be sufficient to remove potential interferents of Taq polymerase in clinical samples, such as hemoglobin, anti-coagulants (like EDTA), humic or fulvic acids, and residual lysis buffer components.

FIG. 12 provides PCR amplification results for nucleic acids spiked into clean buffer, whole blood or a solution containing 1 ug/uL humic and fulvic acids. 100 fg of DNA from *B. anthracis* was spiked into PBS (buffer only, light grey bars), whole blood (Blood spike—dark grey bars), or a buffer sample containing 1 ug/uL humic acid and fulvic acid (humic Spike—white Bars). Samples were then either purified using the extraction prototype (+Purification) or not (−Purification). Eluate from the purified samples or material from the unpurified samples was amplified by PCR to determine the effects of purification and removal of potential PCR inhibitors. After amplification the samples were analyzed using 16-plex assay plates. FIG. 12 shows recovery and detection of the BA. Without purification, blood and humic acid completely inhibited the PCR reactions, reducing the assay signals to background levels. Using the purification prototype column and protocol we were able to recover the PCR assay signals in these matrices and generate signals that were roughly equivalent to those observed in clean buffer (PBS).

Efficiency of Cell Lysis Protocol.

The use of lysis buffer to achieve efficient lysis of a number of gram positive and gram negative model bacteria was demonstrated in the prototype purification system. In one study, vegetative *Bacillus anthracis* (Ames strain non-encapsulated) was used to validate the performance of cell lysis and nucleic acid purification protocols and to compare them to a standard laboratory method. The lysis procedure was robust enough to completely lyse the vegetative bacteria in a about 2 minutes. Moreover, this method outperformed a conventional, multi-step labor intensive lysis method (Qiagen®), when compared in parallel. The CT values for the real-time analysis of the eluted product are shown in FIG. 13. Briefly, vegetative non-encapsulated *B. anthracis* (Ames strain) were lysed and purified using either the lysis buffers and methodology described hereinabove or the Qiagen® QiaAmp® procedure. CT values obtained by the present method were lower or comparable to those obtained with the Qiagen® method. Colony formation analysis was done using aliquots of the target organism before and after addition of lysis buffer. There were no viable bacteria after the addition of lysis buffer, confirming the efficacy of the lysis buffer in lysing bacterial cells.

Example 2. Nucleic Acid Amplification

Primer Selection.

To amplify 16 gene targets (8 agents, 16 gene targets including 6 RNA and 10 DNA targets), primers were used that had been selected for real time PCR assays. The primers generated amplified products that were long enough to allow for detection of amplified product through the use of probes directed to the sequences between the priming regions. In some cases small changes were made to the primers (slight changes in length or small shifts along the target sequence) to improve amplification efficiency or to ensure that all the primers had similar melting temperatures The final primer sequences are provided in FIG. 14.

Reverse Transcription Assay Formulation.

Three of the pathogens in the final reaction cocktail had RNA genomes: Venezuelan Equine Encephalitis virus (VEE), Marburg virus (MV), and Ebola virus (EV) In order to amplify the two targets associated with each of these pathogens, a reverse transcription (RT) step was necessary. To reduce the number of oligonucleotide primers present in the final RT reaction cocktail, all RT reactions utilized the reverse PCR primer as the first strand synthesis primer. This method of cDNA synthesis should also convey another level of specificity as only cDNA templates specific for the target of interest will be synthesized.

During preliminary studies of RT conditions, we found that the presence of reverse transcriptase can have severe inhibitory effects on subsequent PCR reactions. This effect is known (Sellner L N et al., Nucleic Acids Res. 1992, 20, 1487-90) and is usually avoided by diluting the RT product before performing PCR, a procedure that would complicate processing in a cartridge format. Instead of diluting the RT product, we were able to eliminate the effect of RT on the PCR reaction by minimizing the amount of reverse transcriptase in the RT mixture and adding tRNA to the reaction mixture. To test RT interference on DNA amplification, we took a DNA target (FT) and processed it using the full RT and PCR protocol. We tested both a one step RT&PCR protocol (all primers present through RT and PCR steps) and a two step RT&PCR protocol (only reverse PCR primers for RNA targets present during RT step). FIG. 15 shows that addition of tRNA completely reverses the inhibitory effect of RT enzyme on PCR (see Panel B). Panel A shows the amplification of a DNA target (FT) using our 16-plex primer mix and a one step RT and PCR protocol (all primers for DNA and RNA targets present during RT step). Panel B shows the amplification of the same DNA target (FT) using two step RT and PCR protocol (only the reverse primers for the RNA targets were present during the RT step—remaining primers were added after completion of RT step. In both cases we compared different RT enzymes: Superscript II (Lanes 1,2), Superscript III (Lanes 3,4), MMLV (Lanes 5,6) or No RT enzyme (Lanes 7,8). We also compared running the reactions in the presence (Lanes 1, 3, 5 and 7) or absence (Lanes 2, 4, 6 and 8) of 0.2 ug/rxn Yeast tRNA. Each reaction was carried out using 1 pg of FT DNA, a 10 min, 46° C. RT step and 33 cycles of PCR (45 s at 94° C. and 60 s at 63° C.). The results show that i) the presence of tRNA is important to prevent RT from inhibiting amplification of DNA targets; ii) the two-step protocol provides cleaner PCR products than the one-step protocol and iii) there is little difference between the RT enzymes in the two-step protocol, however, SuperScript III showed the lowest levels of amplification artifacts in the one-step protocol.

Incubation time for reverse transcription was also optimized using RNA targets. To determine this we used a fixed amount of VEE, MV, or EV RNA and ran RT at 46° C. for between 30 seconds and 6 min. After the RT reaction, the RT was inactivated at 97° C. (a condition that also activates Taq polymerase) and the DNA RT product was amplified by 33 cycles of PCR. We found that RT times as short as 2 minutes were sufficient to allow for detection of RNA targets (data not shown).

Optimization of PCR Conditions.

Initial work on optimizing PCR amplification conditions for our 16-plex amplification reaction was carried out using a conventional thermocycler to allow for rapid evaluation of many different reaction parameters. To somewhat mimic the thermocycling approach that will be used in the cartridge (movement of fluid between two temperature zones) we chose a commercial thermocycler (the RoboCycler®) that operates by moving reaction tubes between heat blocks held at different temperatures.

To achieve efficient amplification, we investigated several inter-related reaction parameters: i) the effect of PCR cycle time, balancing between the ability to run more cycles in a 15 minute period and the lower amplification efficiency of faster PCR cycles; ii) for a given cycle time, the optimal ratio of time spent in the anneal/extend phase vs. time spent in the denaturation phase; and iii) we optimized anneal/extend and denaturation temperatures for rapid amplification conditions. Detection of the amplified products was conducted in multi-well plates using a multiplexed ECL sandwich hybridization format as described hereinbelow.

FIG. 15(c) shows the results of an experiment using a model 6-plex PCR assay to examine the tradeoff between PCR cycle duration and the number of PCR cycles that can be run in a 15 min amplification reaction. DNA (100 fg of BA, FT or YP DNA) was amplified using a 15 minute 6-plex amplification protocol (2 gene targets per organism). The number of PCR cycles in that 5 min. amplification protocol was varied from 30 to 45 cycles by adjusting the duration of each cycle from 20 to 30 seconds. Products were analyzed in a six-plex ECL sandwich hybridization assay. The graph shows that optimal signal was observed when 40-45 cycles were run. In this experiment, 60% of each cycle was dedicated to the anneal/extend step (at 54° C.) and 40% of each cycle was dedicated to denaturation (at 95° C.).

Figure 16D:
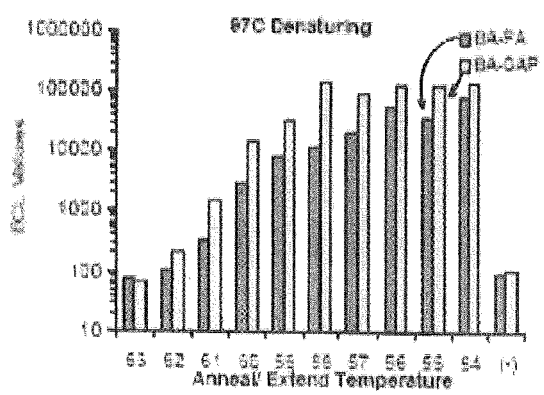
Figure 16E:
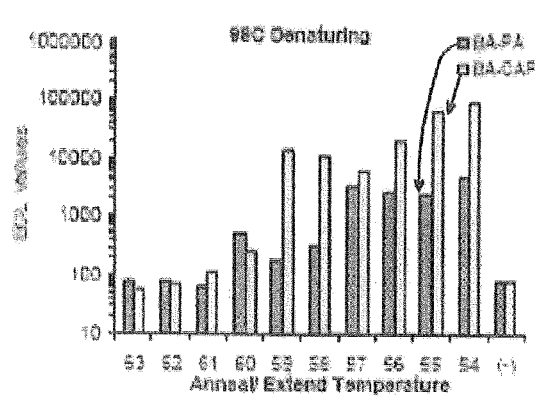

FIG. 16(a) shows that for the BA-PA target, an annealing temperature of 56° C. and a cycle dedicating 60% of cycle time to the anneal/extend step gave optimal amplification when using a fast (20 sec.) overall cycle time. The graph also shows that these values provide good robustness to small changes in temperature or anneal/extend time. In this experiment, BA DNA was amplified under 45 cycles of PCR using a 20 second PCR cycle time and a denaturation temperature of 95° C. The annealing temperature was varied as was the percentage of time in each PCR cycle allocated to the anneal/extend step. The graph shows the amount of BA-PA amplification product as measured using an ECL sandwich hybridization assay. Similar results were observed with other targets. FIGS. 16(b)-(e) show that the optimal denaturation temperature for fast PCR cycles was between 95 to 97° C. BA DNA (100 fg) was amplified in a 15 minute total PCR assay time using 45 cycles (8 sec denature-12 sec anneal/extend). Different combinations of anneal/extend and denaturation temperatures were tested. The BA-PA and BA-CAP amplification products were measured by ECL sandwich hybridization assay. We note that we ran tests with thermocouples in amplification tubes to confirm that the amplification solutions actually reached the set anneal/extend and denaturation temperatures during temperature cycling.

Demonstration of Amplification in PCR Reaction Flow-cell Prototype.

Figure 17:
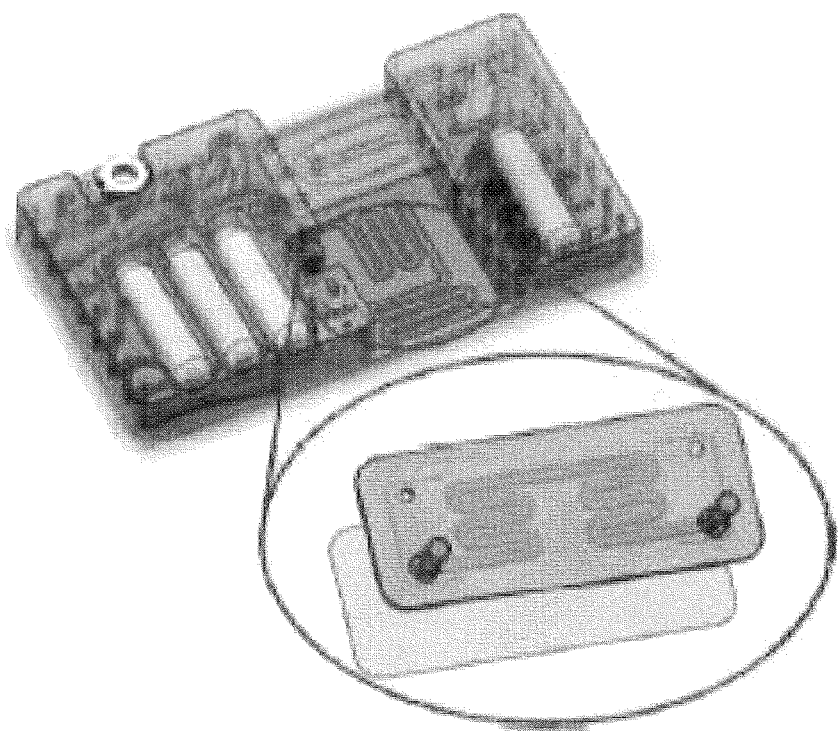
FIG. 17 shows an amplification test bed with heating elements to hold the flow cell and to establish the temperatures zones in the PCR reaction zone of the cartridge.
Figure 19:
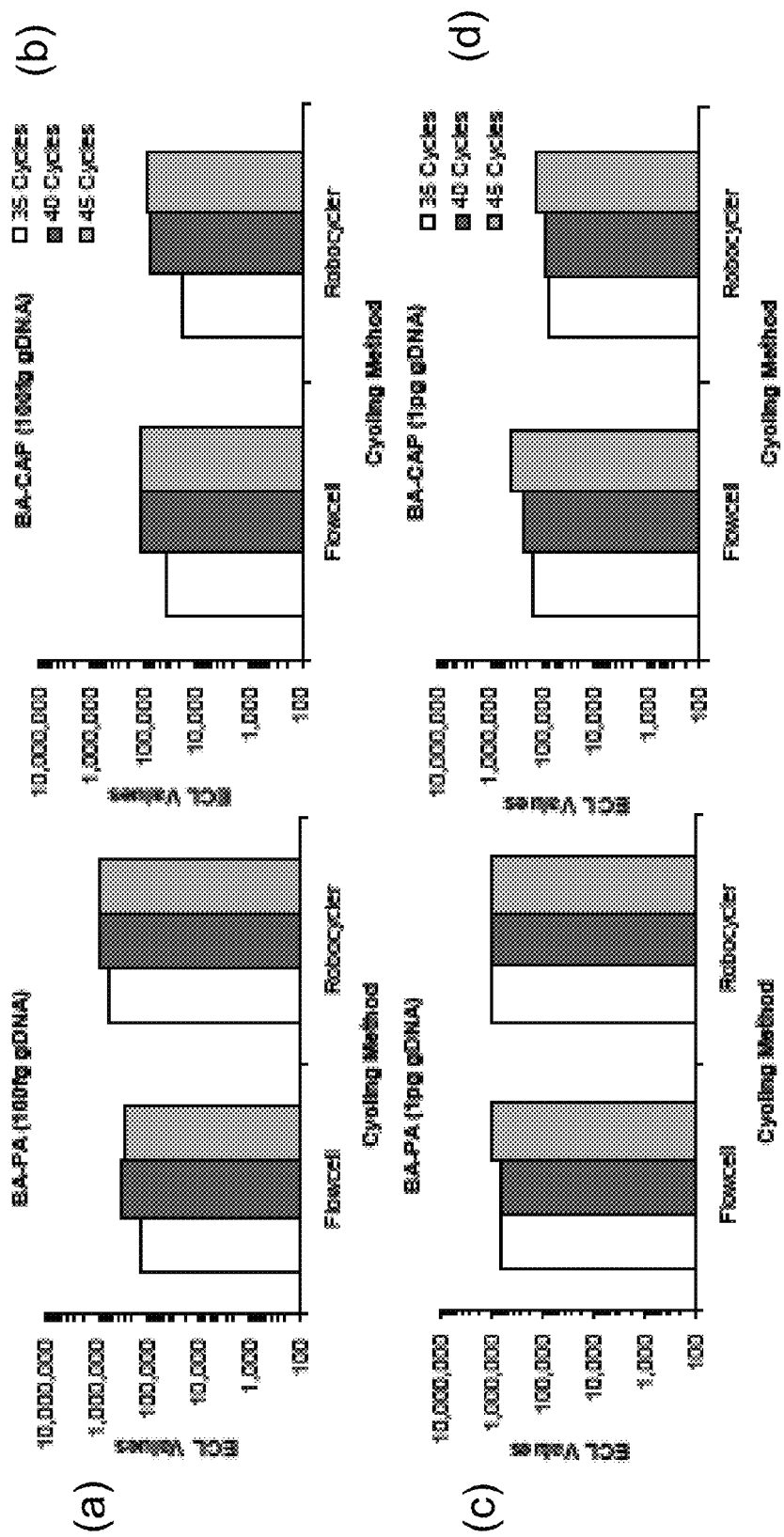
FIG. 19(a-d) show results for amplification of SA genomic DNA.

In the cartridge of the invention, PCR amplification is achieved by moving the reaction mixture between two different temperature zones. We developed injection molded PCR flow cell prototypes to test out the approach in a simplified system. We also developed an amplification test bed with heating elements to hold the flow cell and establish the two temperature zones on the cartridge (FIG. 17). After loading a sample into the flow cell, an air cylinder pump was used to apply air pressure/vacuum to cycle the sample slug between the two temperature zones. Bubble formation can be mitigated by incorporating energy directors on one of the surfaces and using ultrasonic welding to form a smooth interface between the parts. Uniform heating was achieved by providing heating elements on the top and bottom of the flow cell. We used thermocouples in the flow cell to verify that solutions in the flow cell could be cycled between the optimal anneal/extend and denaturing temperatures using our optimal 20 second PCR cycle times, as determined based on experiments using the RoboCycler® thermocycler.

The optimized 16-plex PCR protocol and reagents developed using the RoboCycler® were transferred to the flow cell format. Experiments to determine the optimal amplification efficiency across all assays were used to compare the flow cell prototype and the RoboCycler®. To determine amplification efficiency, a known amount of synthetic material, previously calibrated to give a desired signal in an ECL hybridization assay, was used as the target for amplification. A target level that generated a measurable ECL readout after 10 cycles of amplification but did not saturate either the detection or amplification system was selected. This method of measuring amplification efficiency reduces the potential variability introduced when extensive amplification through 35-45 cycles is used. In an ideal reaction, each PCR cycle will result in a doubling, equal to an amplification factor of 2 per cycle. Given the need for single copy detection, we wanted to achieve a minimum amplification factor of about 1.7 for all assays in the multiplex. Even at a lower amplification factor of 1.6, 45 cycles of amplification should give a total amplification of $>10^9$, which should be more than sufficient for single molecule detection given that the detection limit of our ECL hybridization assays is typically less than $10^7$ copies.

FIG. 18 is a table of amplification efficiencies measured in the flow cell prototype for each of our 16 targets. Most of the assays have amplification factors well above our selected goal. The table also provides amplification efficiencies measured using the RoboCycler® thermocycler; there was no significant difference between amplification in the flow cell/test-bed and amplification using the commercial thermocycler.

We also tested the ability of the PCR amplification flow cell prototype and test-bed to efficiently amplify genomic DNA using our optimized quick cycling PCR amplification protocol (20 second cycle time except for an initial 90 second denaturation step to fully unfold the genomic DNA and to activate the Taq polymerase). Amplified DNA was then removed from the flow cell tested in an ECL sandwich hybridization assay as described in detail hereinbelow, FIG. 19(a)-(d) shows results for amplification of SA genomic DNA. We found that we could detect 100 fg of SA genomic DNA with high signal to background in as few as 35 cycles. For this level of genomic material, there was only minimal improvement in signal by increasing the number of cycles to 45, suggesting that the amplification reaction has already reached saturation at 35 cycles and that effective amplification could be achieved in as little as 12 minutes (35 cycles×20 seconds per cycle=~12 min.).

Example 3. Nucleic Acid Detection

Construction of Nucleic Acid Detection Assay.

Figure 4:
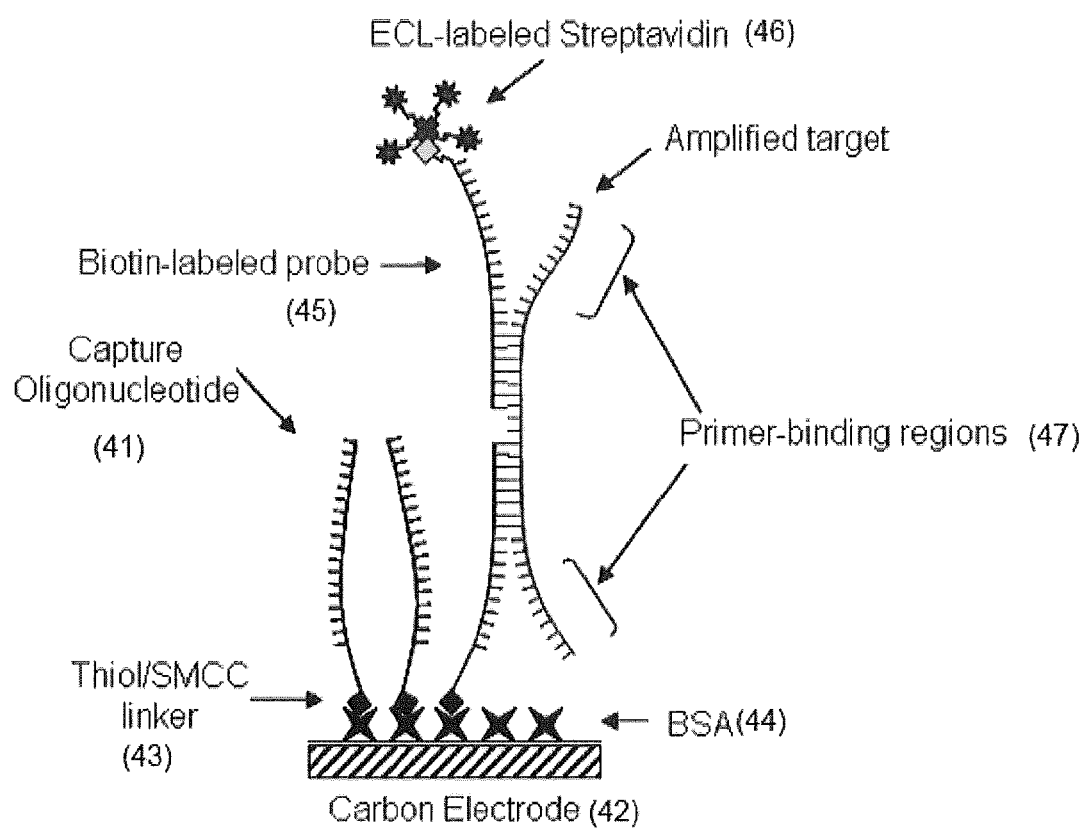
FIG. 4 depicts a method of conducting a nucleic acid detection measurement in a cartridge of the invention.

Detection of target amplicons was performed using a sandwich hybridization format using electrochemiluminescence technology (FIG. 4). To allow for a higher-throughput evaluation of critical parameters, the detection assays were initially developed and optimized in a 96-well plate format using Meso Scale Diagnostics, LLC (MSD, Gaithersburg, Md.) commercial MULTI-ARRAY® plate consumables and SECTOR® Imager plate readers. These plates have integrated carbon ink electrodes in each well that serve as both solid phase supports for binding assays as well as the source of electrical energy for ECL measurements. As shown in FIG. 4, each amplified target was measured by binding it to two oligonucleotide probes: a capture probe that was immobilized on the carbon ink electrode and a detection probe that was linked to an ECL label. Binding of the probes was measured by applying an electrical potential to the electrode and measuring the emission of light from the ECL label. The two probe sequences were selected to bind the target between the primer binding regions, to eliminate potential interference from the primers and to provide an additional level of specificity for the targets. Probe selection software was used to ensure that the probes had roughly the same melting temperatures, were specific for the target organism and would not bind human DNA. The final probe sequences are provided in FIG. 20(a).

The capture probe arrays were immobilized on the electrode by direct adsorption from arrays of drops of solution printed on the electrodes. To enhance direct adsorption, we use 5' thiolated capture probes that are pre-linked to BSA, through SMCC linker chemistry. Previous studies have demonstrated that this method works well to provide reproducible immobilization of the probes while ensuring that they are properly presented so that they bind their target sequences. BSA with various amount of attached capture probes were tested, from 1:1 to 10:1 challenge ratio, and it was found that challenge ratios greater than 5:1 generated the highest ECL signals for the model assays tested.

Arrays of the capture probes were printed in the wells of MULTI-ARRAY plate using custom array printing instruments. The detection probes were labeled with a 3' biotin residue. The detection probes were pre-bound, at a 1.1 ratio, to streptavidin labeled with an ECl label (SULFO-TAG™) so that formation of a sandwich hybridization complex could be detected by ECL. Detection probes are composed of unique oligonucleotides sequences containing a 3' biotin residue.

Optimization of the Sandwich Hybridization Assay Format.

Initial assay optimization was carried out in our multi-well plate format, allowing us to efficiently optimize a number of factors including probe concentrations, buffer formulations, probe sequence selection and development of procedures and reagents for blocking probe arrays to reduce non-specific binding As part of this task we compared running hybridization assays as one-step or two-step reactions. In a one-step assay, the amplified product is mixed with the capture and detection probes simultaneously. In a two-step assay, the product is first bound to the immobilized capture probe and is then-allowed to bind to the detection probe (optionally, after first washing away unbound sample). In either format, the array is washed and an ECL Read Buffer (MSD T Read Buffer, available from Meso Scale Diagnostics, LLC, Gaithersburg, Md.) is added, prior to conducting the ECL measurement. As a last step of our PCR amplification reactions, we add Taq inhibitors and then run a denaturing reaction to dehybridize the double stranded products and make them accessible for binding to the capture and detection probes.

We found that amplification products for some targets gave lower than expected signals in our hybridization assays. For example the full length amplicons generated from VEE 5'UTR and NSP4 provided much lower ECL signals than short synthetic targets containing only the capture and detector probe binding regions. We speculated that this difference is most likely due to the formation of internal loops or folds in the target amplicons that block binding of the capture or detector probes. We found two approaches that could be used to recover the signal to expected levels. The first approach involves adding short pieces of blocking DNA to the hybridization reaction. The blocking DNA sequences are selected to be complementary to regions in the target sequence that are involved in formation of secondary structure (so as to block formation of the secondary structure) but are also selected such that they do not overlap with the probe binding sequences. The second approach involves redesigning the PCR primers: we shift the position of one of the primers on the target sequence to shorten the length of the amplicon and remove nucleotides involved in secondary structure formation (FIG. 20(b) and Table 1 below).

TABLE 1

VEE-5'UTR Current Primer/Probe Set:
GAGCTTCCCGCAGTTTGAGGTAGAAGCCAAGCAGGTCACTGATAATGA
CCATGCTAATGCCAGAGCGTTTTCGCATCTGGCTTCAAAACTGA
TCGAAACGGAGGTGGACCC
(SEQ ID NO: 1)

| | |
|---|---|
| Primer | GAGCTTCCCGCAGTTTGA AAACGGAGGTGGACCC (SEQ ID NO: 2) |
| Detector | GCCAAGCAGGTCACT (SEQ ID NO: 3) |
| Capture | GACCATGCTAATGCCA (SEQ ID NO: 4) |
| Blocking Pieces | GAGCTTCCCGCAGTTTGAGGTAGAAGAGCGTT TTCGCATCTGGCTTCAAAACTGAT CGAAACGGAGGTGGACCC (SEQ ID NO: 5) |

VEE-5'UTR New Primer/Probe Set:
GAGCTTCCCGCAGTTTGAGGTAGAAGCCAAGCAGGTCACTGATAATG
ACCATGCTAATGCCAGAGCGTTTTCGCATCTGGCTTCA
(SEQ ID NO: 6)

| | |
|---|---|
| Primer | GAGCTTCCCGCAGTTTGA CGTTTTCGCATCTGGCTTCA (SEQ ID NO: 7) |
| Detector | GTAGAAGCCAAGCAGG (SEQ ID NO: 8) |
| Capture | GATAATGACCATGCTAATG (SEQ ID NO: 9) |
| Blocking Pieces | — |

VEE-NSP4 Current Primer/Probe Set:
CTTGGCAAACCTCTGGCAGCAGACGATGAACATGATGATGACAGGAG
AAGGGCATTGCATGAAGAGTCAACACGCTGGAACCGAGTGGGTAT
(SEQ ID NO: 10)

| | |
|---|---|
| Primer | CTTGGCAAACCTCTGGCAGC CGCTGGAACCGAGTGGGTAT (SEQ ID NO: 11) |
| Detector | GATGAACATGATGATGAC (SEQ ID NO: 12) |
| Capture | GGGCATTGCATGAAG (SEQ ID NO: 13) |
| Blocking Pieces | CTTGGCAAACCTCTGGCAGCAGAC GTCAACACGCTGGAACCGAGTGGGTAT (SEQ ID NO: 14) |

TABLE 1-continued

VEE-NSP4 New Primer/Probe Set:
GGCAGCAGACGATGAACATGATGATGACAGGAGAAGGGCATTGCATG
AAGAGTCAACACGCTGGAACCGAGTGGGTAT
(SEQ ID NO: 15)

| | |
|---|---|
| Primer | GGCAGCAGACGATGAACATGATGAT CGCTGGAACCGAGTGGGTAT (SEQ ID NO: 16) |
| Detector | GACAGGAGAAGGGCATTGCA (SEQ ID NO: 17) |
| Capture | TTGCATGAAGAGTCAACA (SEQ ID NO: 18) |
| Blocking Pieces | — |

FIG. 21(a)-(b) shows the effects of these strategies on signals for the VEE 5'UTR and NSP4 targets. The figures show that the use of blocking sequences to block secondary structure formation was effective and could produce an assay signal increase of 2 to 5 fold. The second approach of shortening the amplicon produced a 100 fold increase in assay signal. We implemented the amplicon shortening approach for the VEE assay.

Performance of 16-Plex ECL Hybridization Assay in Multi-Well Plate Format.

FIG. 22(a-b) demonstrates the performance of our optimized 16-plex ECL sandwich hybridization assays in the multi-well plate format. To be able to correlate results to the number of target sequence copies, these results were generated using samples containing synthetic versions of our 16 gene targets. Detection limits were generally in the range of roughly $10^6$ to $10^7$ copies (assay volumes were about 100 uL). These detection limits are significantly lower than the amount of amplified product that should be generated from a single copy based on our 15 minute, 45 cycle PCR protocol. Based on our calculated per cycle amplification efficiency (about 1.7 or greater), a single copy should generate $\sim 1.7^{45} = 2 \times 10^{10}$ copies of amplified product. FIG. 22 (a-b) also shows the observed levels of cross-reactivity of each target for the different capture probes. In general, the levels of cross-reactivity were below detectable levels. There were five instances where we detected low levels of cross-reactivity (on the order of 1%) of a target for a non-specific capture probe and some additional optimization can be required.

Performance of Multiplexed ECL Hybridization Assay in Cartridge Format.

FIG. 23(a)-(b) shows ECL signals for measuring amplicons from a model 6-plex panel (our 6 genetic targets for BA, FT and YP). We amplified 1 pg of genomic DNA from BA, FT or YP using 33 cycles of amplification on a RoboCycler® thermocycler, followed by quenching of the Taq enzyme with EDTA and denaturation of double stranded product at 95° C. The denatured product was combined with detection probes for the six target sequences and loaded onto an immunoassay cartridge holding an array of capture probes for the same targets. The remaining process steps (incubation with the capture probe array, washing of the array with an ECL read buffer and measurement of ECL) were carried out automatically using an immunoassay reader. To test reaction kinetics, we programmed the reader to vary incubation times from 1 to 15 minutes. We also ran serial dilutions of the samples using a 10 minute incubation to characterize the dilution linearity for the measurement. The graph in FIG. 23(a) shows that by 5 minutes of incubation, assays signals were orders of magnitude above the background measured on a negative control (BSA) assay spot. Discrimination of signal from background was possible even with incubation times as short as 1 min. The table in FIG. 23(b) shows that (for the 10 minute incubation time) the amplification products could be diluted as much as 100-fold and still produce signals significantly above background. In general, the assays signals dropped linearly with dilution, although the signals for some of the assays were saturated for the neat sample. The ability to get signals orders of magnitude above background in a cartridge flow cell using a 5 minute incubation suggest little risk in porting the final 16-plex assays to cartridge electrodes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. An assay cartridge for conducting a PCR analysis of a sample, said cartridge comprising a fluidic network including
   (a) a plurality of air vent ports arranged as one or two rows of apertures on the cartridge,
   (b) a primary flow path comprising, from a proximal to a distal end, an inlet, a purification zone, a PCR reaction zone, and a detection zone, wherein said primary flow path further comprises one or more of said air vent ports,
   (c) one or more chambers connected to an additional one of said air vent port, and
   (d) one or more fluidic conduits each intersecting said primary flow path and fluidically connected to said chamber, wherein a fluidic conduit of said one or more fluidic conduits comprises a multi-conduit fluidic junction including (i) a first conduit connecting said primary flow path and said chamber, and (ii) a second conduit connecting said chamber to said additional air vent port, wherein said fluidic conduit is configured to be in communication with an optical fluid sensor at a position distal from said fluidic junction and a metered volume of fluid is defined by the distance between said fluidic junction and said distal position,
   wherein said PCR reaction zone comprises a first temperature controlled zone and a second temperature controlled zone, and a restriction zone positioned between said first and second temperature controlled zones, and said fluidic network is configured to shuttle a metered volume of fluid between said first and second temperature controlled zones during a PCR reaction conducted in said PCR reaction zone.

2. The assay cartridge of claim 1 wherein said assay cartridge further comprises a plurality of chambers selected from a sample chamber, a reagent chamber, a PCR reagent chamber, a reconstitution chamber, a waste chamber, and a mixing chamber.

3. The assay cartridge of claim 2 wherein said assay cartridge further comprises a sample chamber, a plurality of reagent chambers, a plurality of PCR reagent chambers, a plurality of reconstitution chambers, a waste chamber, and a mixing chamber.

4. The assay cartridge of claim 3 wherein said primary flow path is intersected by a sample chamber multi-conduit fluidic junction including (i) a first sample chamber conduit connecting said primary flow path and said sample chamber; and (ii) a second sample chamber conduit connecting said sample chamber to a sample chamber air vent port, wherein said sample chamber fluidic junction is in communication with a sample chamber optical fluid sensor at a position distal from said sample chamber fluidic junction and said metered volume of fluid is defined by the distance between said sample chamber fluidic junction and said distal position.

5. The assay cartridge of claim 4 wherein said primary flow path is intersected by a mixing chamber multi-conduit fluidic junction including (i) a first mixing chamber conduit connecting said primary flow path and said mixing chamber; and (ii) a second mixing chamber conduit connecting said mixing chamber to a mixing chamber air vent port, wherein said mixing chamber fluidic junction is in communication with a mixing chamber optical fluid sensor at a position distal from said mixing chamber fluidic junction and said metered volume of fluid is defined by the distance between said mixing chamber fluidic junction and said distal position.

6. The assay cartridge of claim 5 wherein said primary flow path further comprises a series of Z-transitions at a position distal from said mixing chamber fluidic junction.

7. The assay cartridge of claim 1 wherein said purification zone is fluidically connected to a first waste chamber and a purification reagent chamber.

8. The assay cartridge of claim 7 wherein said purification zone comprises, from a proximal to a distal end,
   (i) a purification multi-conduit fluidic junction including
      (a) a first purification reagent chamber conduit connecting said primary flow path and said purification reagent chamber; and
      (b) a second purification reagent chamber conduit connecting said purification reagent chamber and a purification reagent chamber air vent port;
   (ii) an integrated purification membrane positioned in said primary flow path of said purification zone; and
   (iii) a waste multi-conduit fluidic junction including
      (a) a first waste chamber conduit connecting said primary flow path and said waste chamber; and
      (b) a second waste chamber conduit connecting said waste chamber and a waste chamber air vent port.

9. The assay cartridge of claim 8 wherein said purification zone comprises an integrated purification membrane positioned on a support frit.

10. The assay cartridge of claim 8 wherein said integrated purification membrane is compressed prior to cartridge assembly.

11. The assay cartridge of claim 8 wherein said integrated purification membrane comprises a glass fiber membrane.

12. The assay cartridge of claim 8 wherein said membrane has a retention volume of less than 10 uL.

13. The assay cartridge of claim 8 wherein said membrane has a retention volume of less than 5 uL.

14. The assay cartridge of claim 8 wherein said membrane has a retention volume of less than 2 uL.

15. The assay cartridge of claim 8 wherein said purification zone further comprises a pre-heating zone preceding said integrated purification membrane.

16. The assay cartridge of claim 8 wherein said purification zone comprises an additional temperature controlled zone.

17. The assay cartridge of claim 1 wherein said primary flow path is intersected at said reaction zone by one or more reagent multi-conduit junctions connecting (i) said primary flow path and one or more reaction reagent chambers; and (ii) said one or more reagent chambers and one or more reagent chamber air vent ports.

18. The assay cartridge of claim 17 wherein said assay cartridge further comprises one or more reconstitution chambers and said one or more reagent multi-conduit junctions further connect (iii) said primary flow path and said one or more reconstitution chambers at said reaction zone.

19. The assay cartridge of claim 17 wherein said reaction zone comprises a reaction zone inlet and a reaction zone outlet, and said one or more multi-conduit junctions intersect said reaction zone at said reaction zone inlet and/or outlet.

20. The assay cartridge of claim 1 wherein said primary flow path is intersected at said detection zone by a detection reagent multi-conduit junction connecting (i) said primary flow path and one or more detection reagent chambers; and (ii) said one or more detection reagent chambers and one or more detection reagent air vent ports.

21. The assay cartridge of claim 20 wherein said detection zone comprises a set of immobilized reagents distributed in said detection zone along said primary flow path.

22. The assay cartridge of claim 21 wherein said detection zone further comprises an exposed working electrode on which said reagents are immobilized.

23. The assay cartridge of claim 20 wherein said detection zone is configured to maintain uniform fluid flow throughout said detection zone.

24. The assay cartridge of claim 20 wherein said detection zone comprises a square geometry.

25. The assay cartridge of claim 20 wherein said primary flow path is U-shaped within said detection zone.

26. The assay cartridge of claim 1 wherein said detection zone further comprises a detection temperature controlled zone.

27. The assay cartridge of claim 1 wherein said cartridge comprises one or more of chambers wherein at least one of the one or more chambers comprises a liquid reagent.

28. The assay cartridge of claim 1 wherein said cartridge comprises one or more of chambers wherein at least one of the one or more chambers comprises a dried reagent that can be rehydrated by said metered volume of fluid.

29. The assay cartridge of claim 1 wherein the surface of said primary flow path within said reaction zone is substantially adhesive free.

30. The assay cartridge of claim 1 wherein the surface of said primary flow path within said reaction zone is substantially free of seams.

31. The assay cartridge of claim 2 wherein said mixing chamber is configured to perform cell lysis.

32. The assay cartridge of claim 31 wherein said mixing chamber is in fluidic communication with said sample chamber and said reagent chamber, and said reagent chamber comprises a lysis reagent.

33. The assay cartridge of claim 32 wherein said mixing chamber further comprises an antifoam reagent.

34. The assay cartridge of claim 1 wherein said purification zone is configured to extract and purify nucleic acids in said sample.

35. The assay cartridge of claim 34 wherein said purification zone is in fluidic communication with a plurality of reagent chambers, wherein said plurality of reagent chambers include a first reagent chamber comprising a lysis buffer, a second reagent chamber comprising a wash buffer, and a third reagent chamber comprising an elution buffer.

36. The assay cartridge of claim 3 wherein each of said reconstitution chambers comprise lyophilized PCR reagents.

37. The assay cartridge of claim 36 wherein said PCR reagents comprise reverse transcriptase, dNTPs, and combinations thereof.

38. The assay cartridge of claim 37 wherein said PCR reagents are housed within a first reconstitution chamber.

39. The assay cartridge of claim 36 wherein said PCR reagents are selected from dNTPs, primers, polymerase, and combinations thereof.

40. The assay cartridge of claim 39 wherein said PCR reagents are housed within a second reconstitution chamber.

41. The assay cartridge of claim 39 wherein said PCR reagents further comprise additional primers.

42. The assay cartridge of claim 41 wherein said PCR reagents are housed within a third reconstitution chamber.

43. The assay cartridge of claim 36 wherein said PCR reagents are selected from EDTA, salt, and combinations thereof.

44. The assay cartridge of claim 43 wherein said PCR reagents are housed within a fourth reconstitution chamber.

45. The assay cartridge of claim 36 wherein said PCR reagents comprise detection probes.

46. The assay cartridge of claim 45 wherein said PCR reagents are housed within a fifth reconstitution chamber.

47. A method of conducting a PCR analysis of a sample in an assay cartridge, said cartridge comprising a fluidic network and a plurality of chambers, wherein said fluidic network comprises:
(a) a plurality of air vent ports arranged as one or two rows of apertures on the cartridge,
(b) a primary flow path comprising, from a proximal to a distal end, an inlet, a purification zone, a PCR reaction zone, and a detection zone, wherein said primary flow path further comprises one or more of said air vent ports,
(c) one or more chambers connected to an additional one of said air vent port, and
(d) one or more fluidic conduits each intersecting said primary flow path and fluidically connected to said chamber, wherein a fluidic conduit of said one or more fluidic conduits comprises a multi-conduit fluidic junction including (i) a first conduit connecting said primary flow path and said chamber, and (ii) a second conduit connecting said chamber to said additional air vent port, wherein said fluidic conduit is configured to be in communication with an optical fluid sensor at a position distal from said fluidic junction and a metered volume of fluid is defined by the distance between said fluidic junction and said distal position,
wherein said PCR reaction zone comprises a first temperature controlled zone and a second temperature controlled zone, and a restriction zone positioned between said first and second temperature controlled zones, and said fluidic network is configured to shuttle a metered volume of fluid between said first and second temperature controlled zones during a PCR reaction conducted in said PCR reaction zone, wherein said one or more chambers include: a sample chamber, a lysis reagent chamber, a lysis chamber, a purification reagent chamber, a plurality of PCR reagent chambers, and one or more waste chambers;

said method comprising the steps of:
(i) metering a volume of sample from said sample chamber to said lysis chamber;
(ii) metering a volume of lysis buffer from said lysis reagent chamber to said lysis chamber;
(iii) lysing said volume of sample;
(iv) moving said lysate from said lysis chamber to said purification zone;
(v) extracting nucleic acid from said lysate;
(vi) purifying said nucleic acid;
(vii) moving said a purified nucleic acid mixture to said PCR reaction zone;
(viii) contacting said purified nucleic acid mixture with one or more PCR reagents;
(ix) shuttling said mixture formed in step (viii) between said first and second temperature controlled zones;
(ix) repeating steps (viii) and (ix) to form an amplified product mixture;
(x) contacting said amplified product mixture with a detection reagent;
(xi) moving said mixture formed in step (x) to said detection zone; and
(xii) measuring a signal from said detection zone.

48. The method of claim 47, wherein said purification zone comprises, from a proximal to a distal end,
(i) a purification multi-conduit fluidic junction including
  (a) a first purification reagent chamber conduit connecting said primary flow path and said purification reagent chamber; and
  (b) a second purification reagent chamber conduit connecting said purification reagent chamber and a purification reagent chamber air vent port;
(ii) an integrated purification membrane positioned in said primary flow path of said purification zone; and
(iii) a waste multi-conduit fluidic junction including
  (a) a first waste chamber conduit connecting said primary flow path and said waste chamber; and
  (b) a second waste chamber conduit connecting said waste chamber and a waste chamber air vent port;

and said extracting step (v) comprises
(xx) capturing lysate on said membrane;
(yy) removing eluent to said first waste chamber; and
(zz) washing said membrane with one or more purification reagents.

49. The method of claim 38 wherein said purifying step (vi) comprises
(xx) drying said membrane;
(yy) washing said membrane with purification reagent; and
(zz) eluting nucleic acid from said membrane.

50. The method of claim 47 wherein said cartridge further comprises a plurality of reconstitution chambers each comprising lyophilized PCR reagents and contacting step (viii) further comprises reconstituting one or more of said lyophilized PCR reagents.

51. The method of claim 50 wherein said cartridge further comprises a first reconstitution chamber comprising a first set of PCR reagents selected from reverse transcriptase and dNTPs, and said method further comprises reconstituting said first set of PCR reagents in said contacting step (viii) and shuttling said mixture formed in said contacting step between said first and second temperature controlled zone.

52. The method of claim 51 wherein said cartridge further comprises a second reconstitution chamber comprising a second set of PCR reagents selected from dNTPs, primers, and polymerase, and said method further comprises reconstituting said second set of PCR reagents in said contacting step (viii) and shuttling said mixture formed in said contacting step between said first and second temperature controlled zone.

53. The method of claim 52 wherein said cartridge further comprises a third reconstitution chamber comprising a third set of PCR reagents comprising additional primers, and said method further comprises reconstituting said third set of PCR reagents in said contacting step (viii) and shuttling said mixture formed in said contacting step between said first and second reaction temperature controlled zone.

54. The method of claim 53 wherein said cartridge further comprises a fourth reconstitution chamber comprising a fourth set of PCR reagents selected from EDTA, and salt, and said method further comprises reconstituting said fourth set of PCR reagents in said contacting step (viii) and shuttling said mixture formed in said contacting step between said first and second reaction temperature controlled zone.

55. The method of claim 54 wherein said cartridge further comprises a fifth reconstitution chamber comprising detection reagents and said contacting step (x) comprises reconstituting said detection reagents with said amplified product mixture.

* * * * *